(12) United States Patent
Sun et al.

(10) Patent No.: US 12,310,755 B2
(45) Date of Patent: May 27, 2025

(54) METHODS AND SYSTEMS FOR AUTOMATICALLY IDENTIFYING DETECTION PARAMETERS FOR AN IMPLANTABLE MEDICAL DEVICE

(71) Applicant: NeuroPace, Inc., Mountain View, CA (US)

(72) Inventors: Felice Sun, Palo Alto, CA (US); Rosana Esteller, Marietta, GA (US); Adam Lee, Mountain View, CA (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

(21) Appl. No.: 18/480,239

(22) Filed: Oct. 3, 2023

(65) Prior Publication Data

US 2024/0032870 A1 Feb. 1, 2024

Related U.S. Application Data

(63) Continuation of application No. 17/244,897, filed on Apr. 29, 2021, now Pat. No. 11,813,087, which is a continuation of application No. 16/152,152, filed on Oct. 4, 2018, now Pat. No. 11,026,631, which is a continuation of application No. 15/183,325, filed on
(Continued)

(51) Int. Cl.
*A61B 5/00* (2006.01)
*A61B 5/369* (2021.01)
*A61B 5/37* (2021.01)
*A61B 5/374* (2021.01)
*A61N 1/36* (2006.01)

(52) U.S. Cl.
CPC ............ *A61B 5/686* (2013.01); *A61B 5/37* (2021.01); *A61B 5/374* (2021.01); *A61B 5/4094* (2013.01); *A61B 5/7435* (2013.01); *A61B 5/748* (2013.01); *A61N 1/36064* (2013.01); *A61N 1/36135* (2013.01); *A61B 5/4836* (2013.01); *A61B 5/6868* (2013.01); *A61B 5/7278* (2013.01); *A61B 5/7282* (2013.01)

(58) Field of Classification Search
None
See application file for complete search history.

(56) References Cited

U.S. PATENT DOCUMENTS

2003/0073917 A1 4/2003 Echauz et al.
2010/0298676 A1 11/2010 Addison et al.
(Continued)

*Primary Examiner* — Etsub D Berhanu
(74) *Attorney, Agent, or Firm* — LOZA & LOZA, LLP; David S. Sarisky

(57) ABSTRACT

An initial set of parameters for operating one or more detection tools is automatically derived and subsequently adjusted so that each detection tool is more or less sensitive to signal characteristics in a region of interest. Detection tool(s) may be applied to physiological signals sensed from a patient (such as EEG signals) and may be configured to run in an implanted medical device that is programmable with the parameters to look for rhythmic activity, spiking, and power changes in the sensed signals, etc. A detection tool may be selected and parameter values derived in a logical sequence and/or in pairs based on a graphical representation of an activity type which may be selected by a user, for example, by clicking and dragging on the graphic via a GUI. Displayed simulations allow a user to assess what will be detected with a derived parameter set and then to adjust the sensitivity of the set or start over as desired.

19 Claims, 46 Drawing Sheets

Related U.S. Application Data

Jun. 15, 2016, now Pat. No. 10,123,715, which is a continuation of application No. 13/802,456, filed on Mar. 13, 2013, now Pat. No. 9,392,972.

(60) Provisional application No. 61/730,498, filed on Nov. 27, 2012.

(56) References Cited

U.S. PATENT DOCUMENTS

| | | |
|---|---|---|
| 2011/0042580 A1 | 2/2011 | Wilson et al. |
| 2011/0245629 A1 | 10/2011 | Giftakis et al. |
| 2015/0374854 A1 | 12/2015 | Jensen et al. |

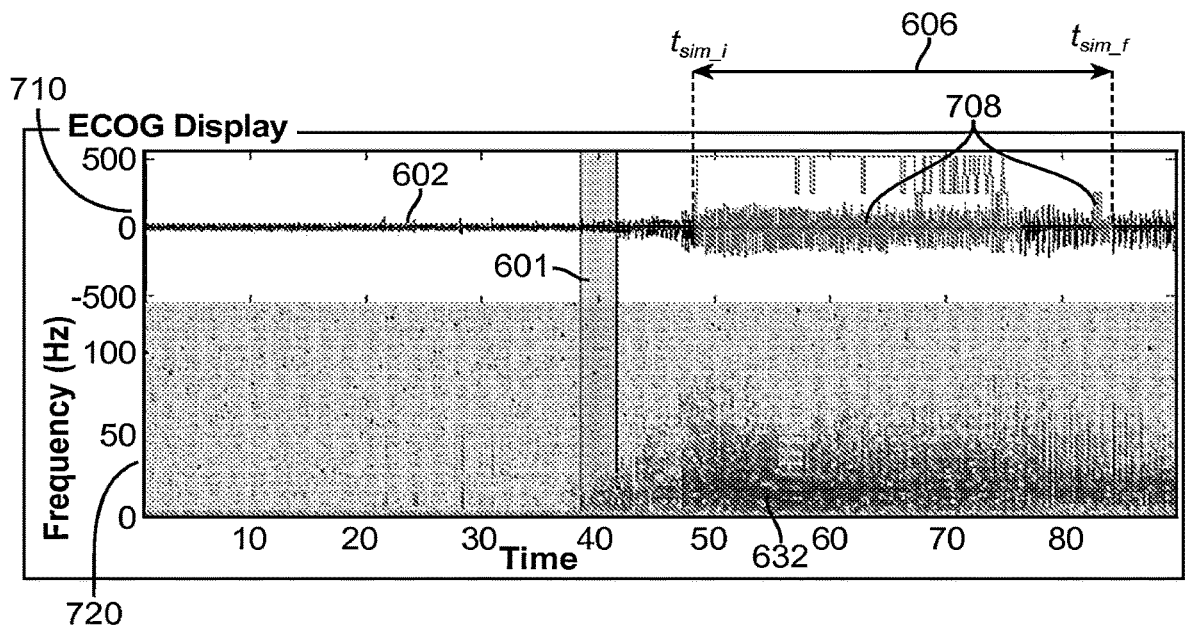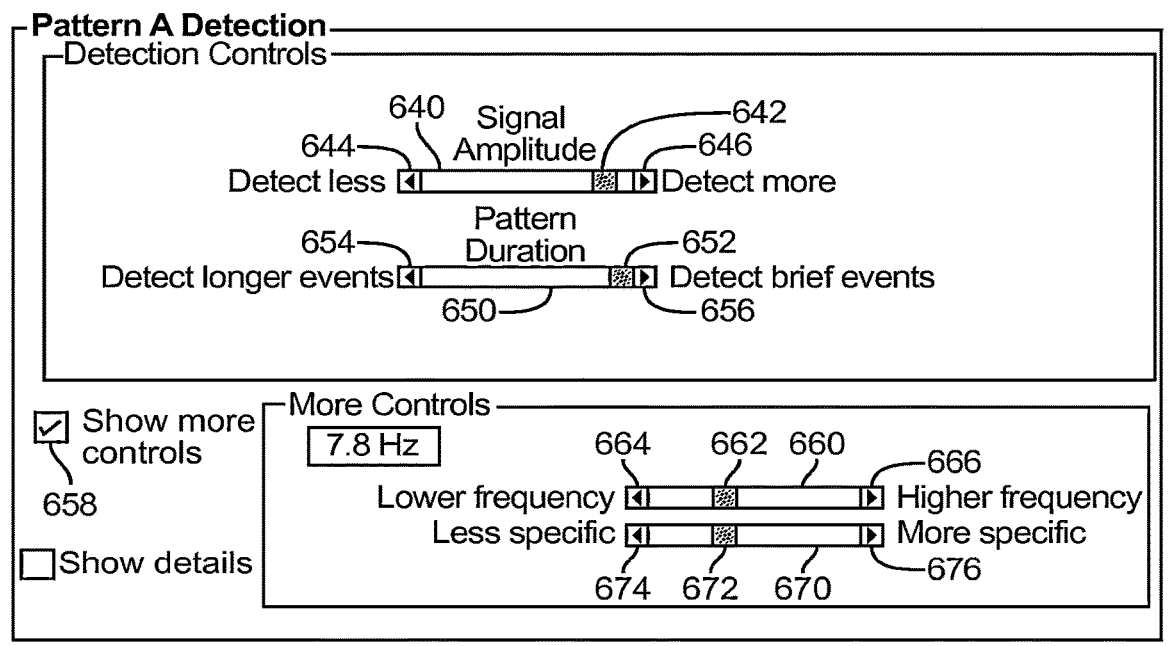
FIG. 7

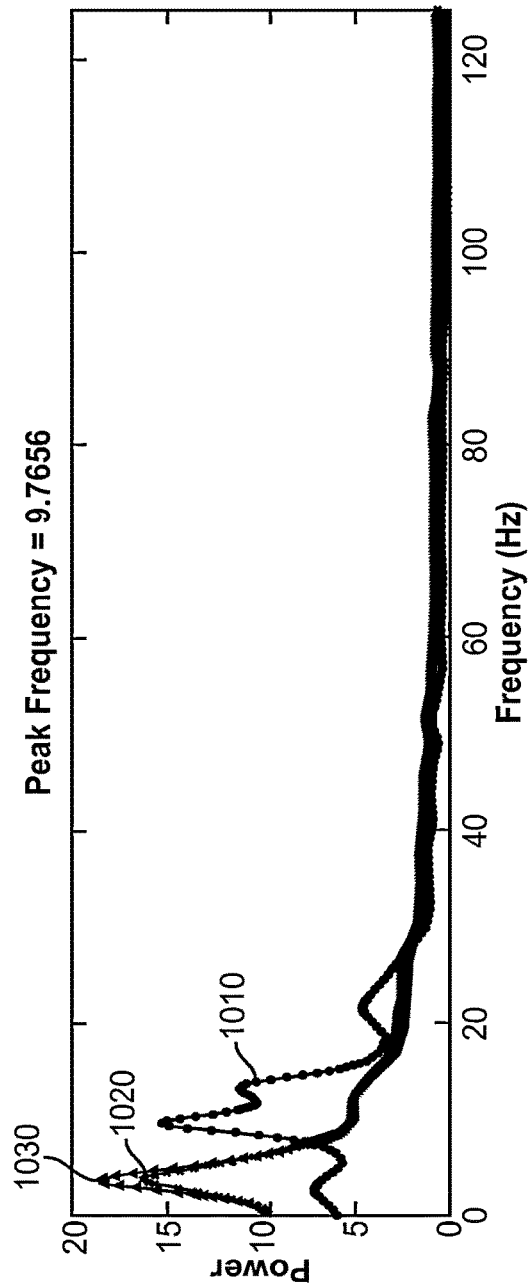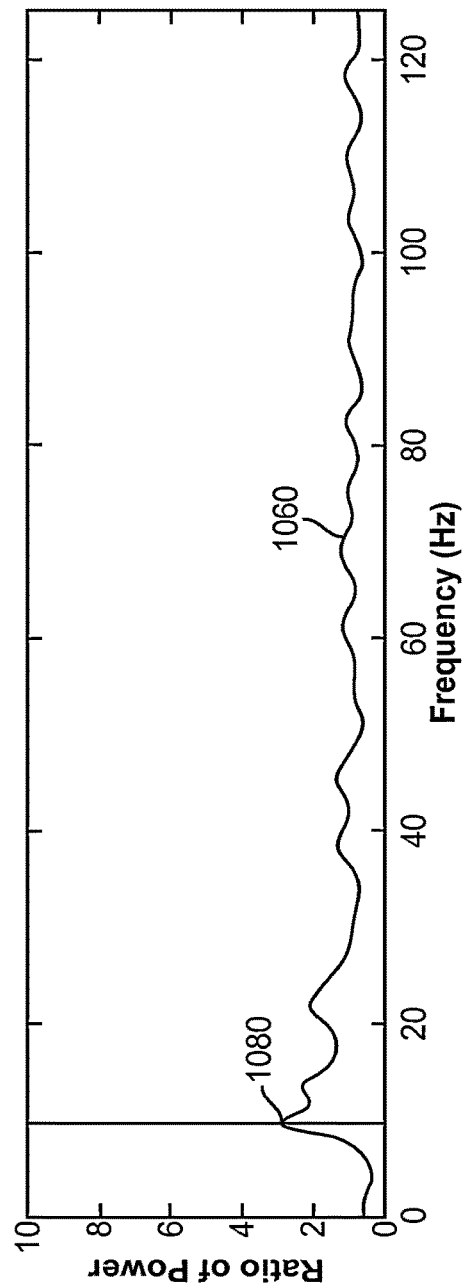
FIG. 10A
FIG. 10B

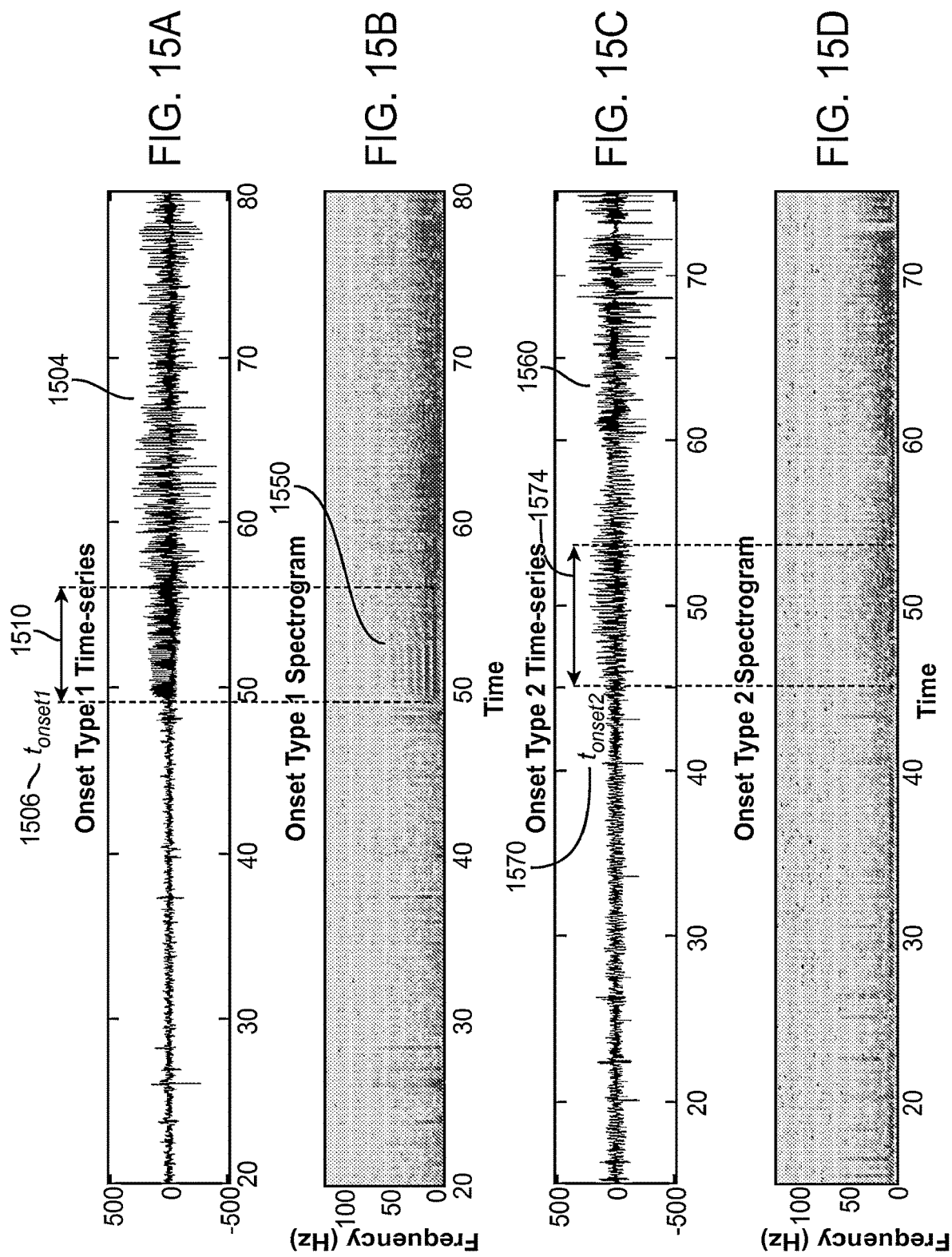

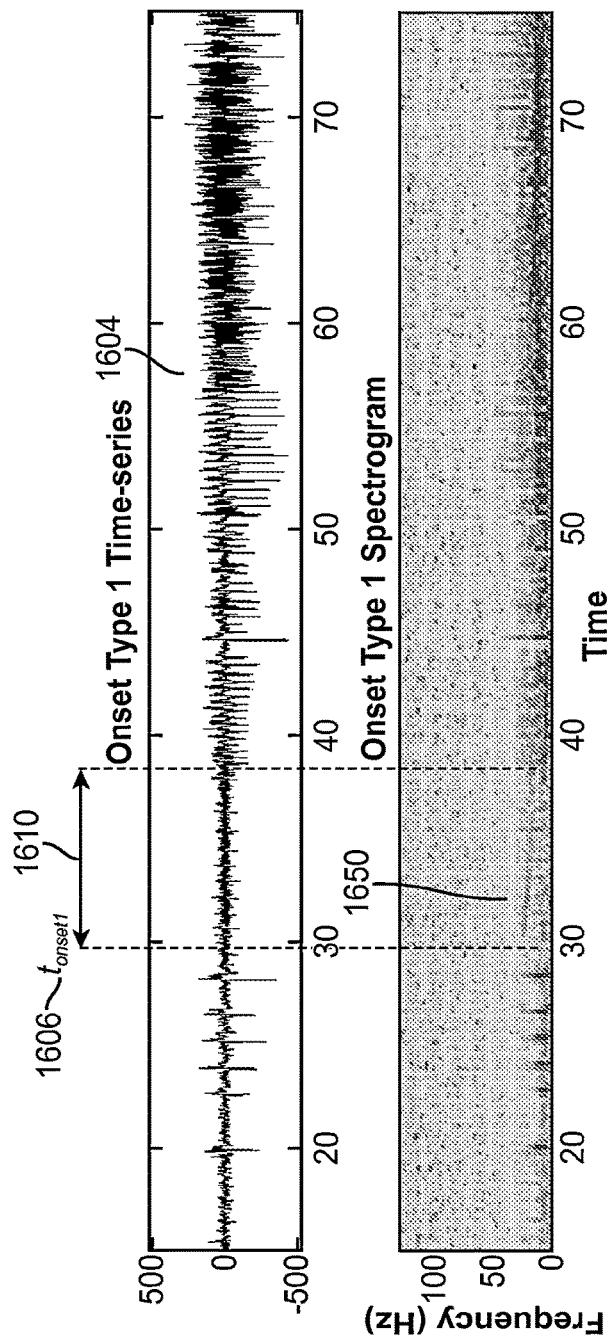

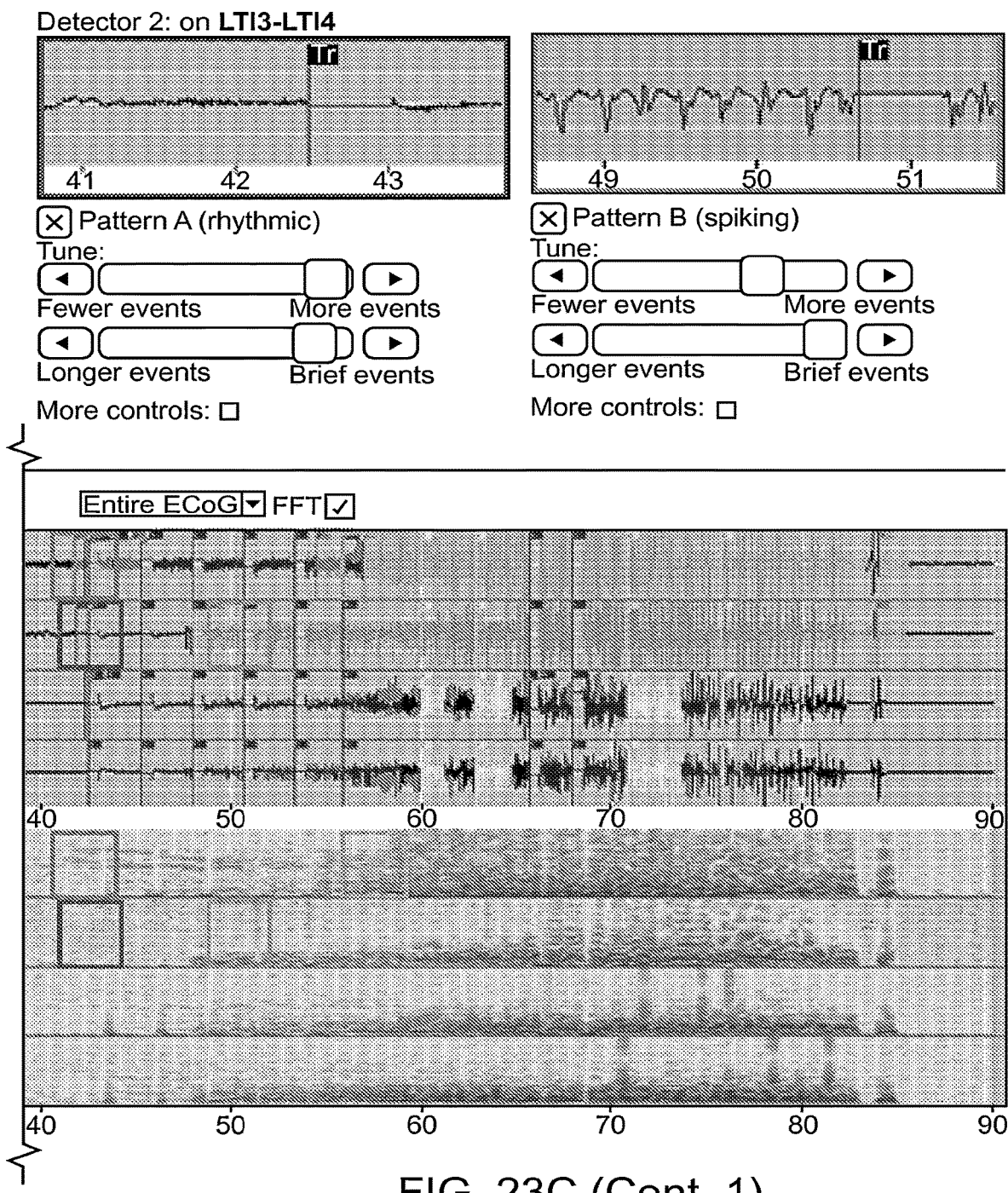
FIG. 23C (Cont. 1)

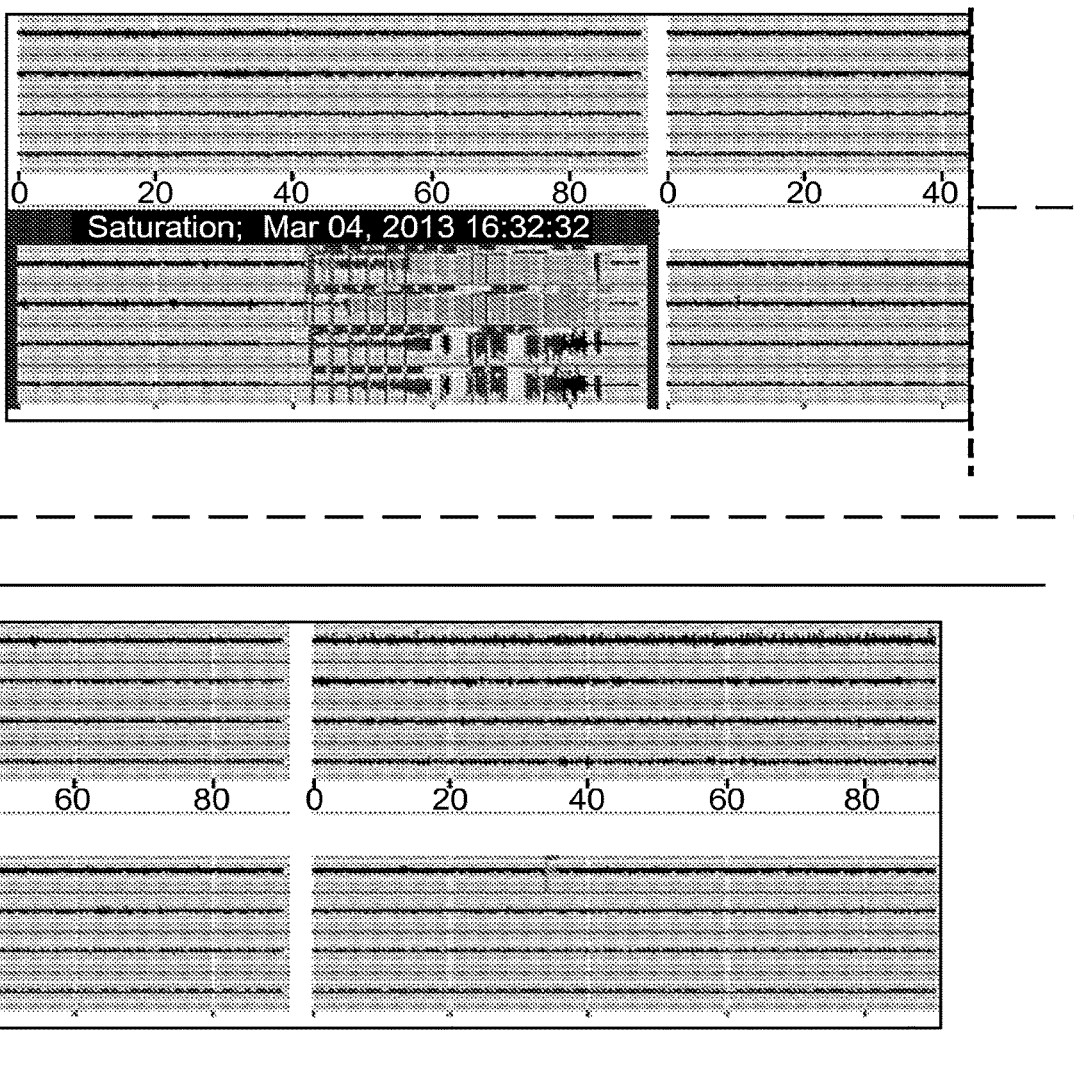
FIG. 23C (Cont. 2)

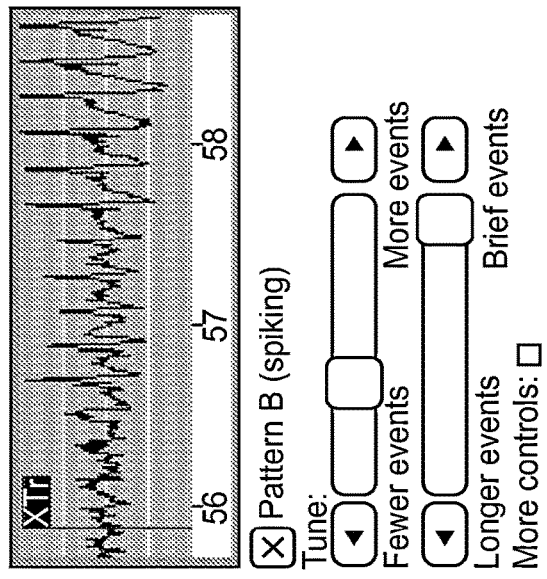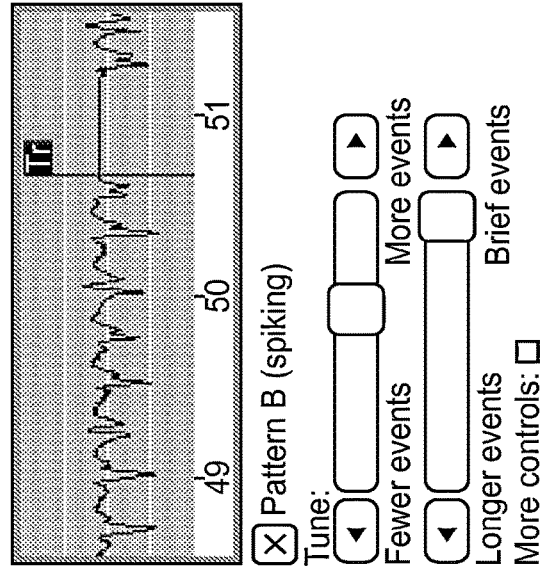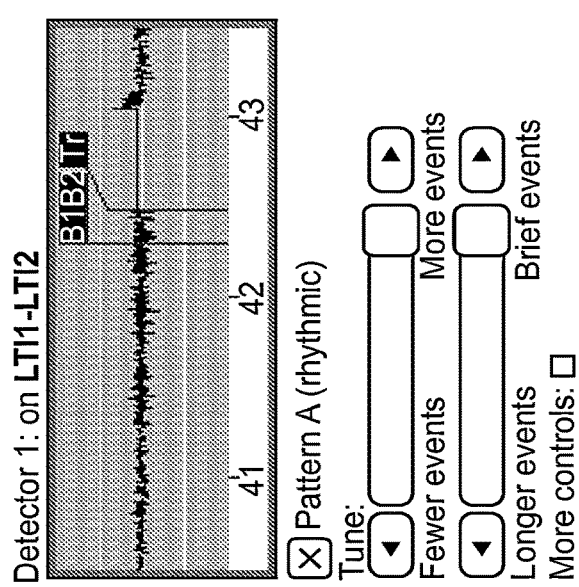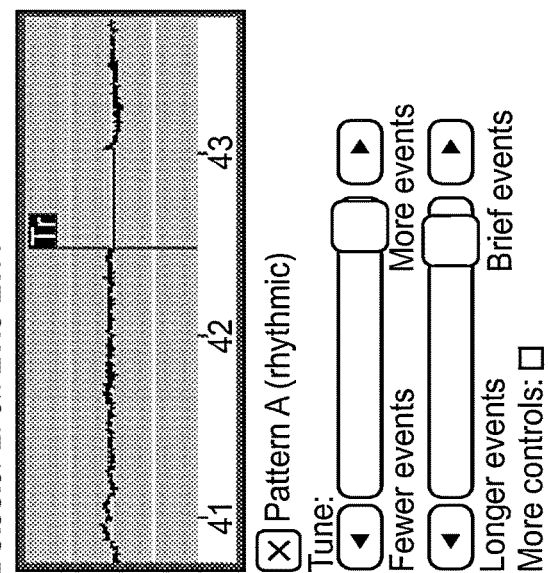
FIG. 23D

METHODS AND SYSTEMS FOR AUTOMATICALLY IDENTIFYING DETECTION PARAMETERS FOR AN IMPLANTABLE MEDICAL DEVICE

CROSS-REFERENCE TO RELATED APPLICATIONS

This application is a continuation of U.S. application Ser. No. 17/244,897, filed Apr. 29, 2021, now U.S. Pat. No. 11,813,087 issued Nov. 14, 2023, entitled "Methods and Systems for Automatically Identifying Detection Parameters for an Implantable Medical Device," which is a continuation of U.S. application Ser. No. 16/152,152, filed Oct. 4, 2018, now U.S. Pat. No. 11,026,631 issued Jun. 8, 2021, entitled "Methods and Systems for Automatically Identifying Detection Parameters for an Implantable Medical Device," which is a continuation of U.S. application Ser. No. 15/183,325, filed Jun. 15, 2016, now U.S. Pat. No. 10,123,715 issued Nov. 13, 2018 entitled "Methods and Systems for Automatically Identifying Detection Parameters for an Implantable Medical Device," which is a continuation of U.S. application Ser. No. 13/802,456, filed Mar. 13, 2013, now U.S. Pat. No. 9,392,972 issued Jul. 19, 2016, entitled "Methods and Systems for Automatically Identifying Detection Parameters for an Implantable Medical Device," which claims priority to and the benefit of U.S. Provisional Patent Application No. 61/730,498 filed Nov. 27, 2012, entitled "Methods and Systems for Automatically Identifying Detection Parameters for an Implantable Medical Device," the entire disclosures of which are incorporated herein by reference.

FIELD OF THE INVENTION

The present technology relates generally to methods and systems for identifying the parameters that will determine what an active implantable medical device detects relative to physiological data being monitored by the implantable medical device, especially identifying detection parameters relative to electrographic activity.

BACKGROUND

Systems and methods that include algorithms for identifying when physiological data sensed from a patient exhibit certain features or correspond to certain physiological states are desirable in diagnosing, monitoring and treating patients. Specifying the parameters necessary for the algorithms to operate as expected and to generate the desired outcome is generally not an intuitive process for the patient's physician. It would be beneficial to make these systems and methods easier for a physician to use with regard to a particular patient or set of patients.

BRIEF DESCRIPTION OF THE DRAWINGS

FIG. 10A is a plot comparing the frequency content of a region of interest in an electrographic signal to the frequency content of two regions of baseline activity according to embodiments.

FIG. 10B is a plot representing a ratio of the frequency content of a region of interest to the frequency content of one or more regions of baseline activity according to embodiments, revealing a salient frequency at about 10 Hz.

FIG. 15A, FIG. 15B, FIG. 15C, and FIG. 15D are graphical representations, namely, a time-series representation of an electrographic signal and a spectrogram of the same signal, of each of two dissimilar regions of interest associated with a similar condition (e.g., onset of seizure activity).

FIG. 16A, FIG. 16B, FIG. 16C, and FIG. 16D are graphical representations, namely, time-series representations, of an electrographic signal and a spectrogram of the same signal, of each of two similar regions of interest associated with a similar condition (e.g., onset of seizure activity).

FIG. 23A, FIG. 23B, FIG. 23C, FIG. 23D and FIG. 23E each is a screen shot of a graphical user interface as may be used according to embodiments.

Figure 1A:
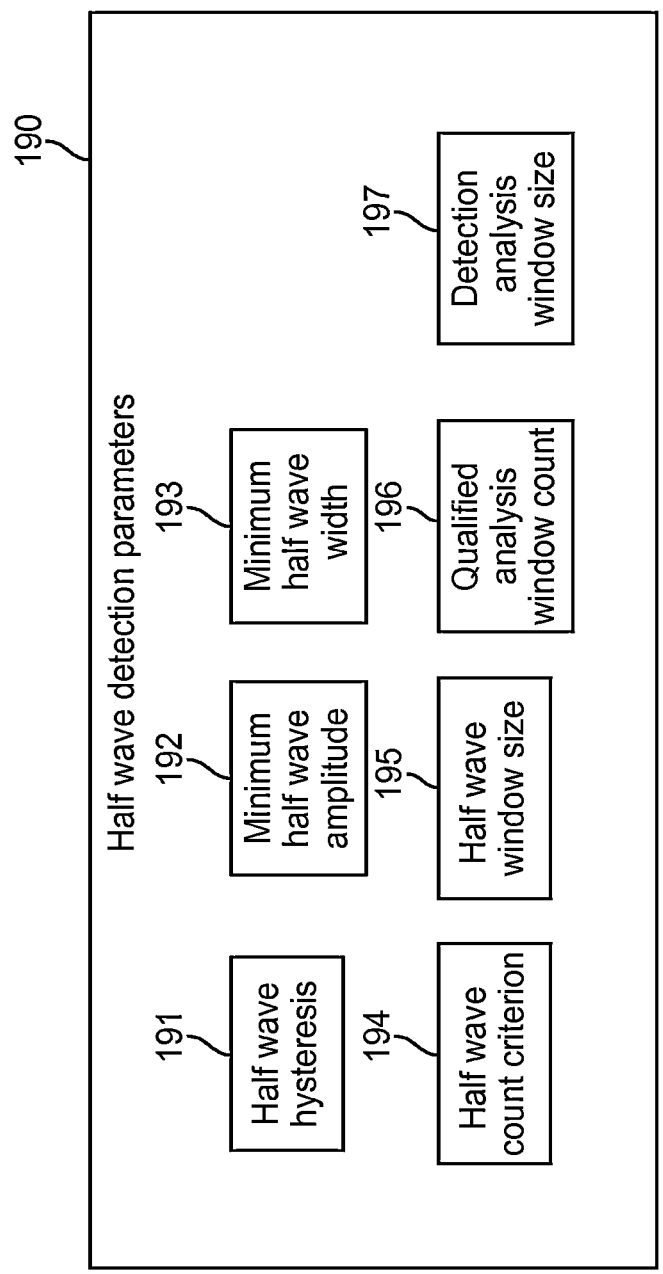
FIG. 1A is a schematic illustration of a set of adjustable detection parameters that, among others, may be associated with a half wave detector.

The drawings referred to in this description should not be understood as being drawn to scale unless specifically noted.

DETAILED DESCRIPTION

Implantable medical systems are under investigation that use sensors to monitor electrographic signals obtained from a patient and then record portions of the monitored signals (or some type of digital representation thereof) whenever the signals exhibit certain characteristics (e.g., when certain conditions are satisfied and/or when certain thresholds are exceeded or not met). One implantable component of these medical systems may be configured to determine when the certain characteristics are exhibited in the monitored signals. An implantable component also may be configured to determine whether and when the monitored signals correspond to a particular physiological state based on a condition of the implantable medical device itself (e.g., when an amplifier or amplifiers go into saturation or how often an amplifier or amplifiers go into saturation). Conditions of the implantable medical device itself, as distinguished from the physiological signals the implantable medical device may be configurable to monitor, are often referred to as "diagnostics" or "device diagnostics". Sometimes, one or more device diagnostics may be used as a proxy for a physiological state of the patient. For example, when certain amplifiers in the implanted medical device are saturated and remain saturated for a predetermined period of time, the patient may be deemed to be experiencing an electrographic event (e.g., seizure).

Generally, an implantable component of an implantable medical device system that is configurable to process signals and to run one or more algorithms on data may be referred to herein as an "active implantable medical device" to distinguish it, for example, from a passive implantable component such as a catheter.

One or more algorithms implemented in whole or in part by the implantable component may be relied upon to decide when the characteristics are exhibited in the monitored signals or when one or more of the device diagnostics should be detected as a condition that should be recorded or otherwise noted or acted upon. Each algorithm may operate on one or more channels of data acquired from the patient or on one or more of the diagnostics. An algorithm may be referred to as a "detection tool", a "detector", or an "event detector".

For data acquired from the patient, a given set of sensing channels of the implant and associated algorithms executable by the implant may define a "detection channel." A given detection channel may be associated with one or more event detectors. Different event detectors may be configured for a given patient to use signals that arise from different areas of the patient's brain or signals that are separated by time (e.g., one signal type followed by the same or a different signal type).

When an algorithm is intended to be implemented primarily by an implantable component using an implanted power supply (e.g., a primary cell battery or a rechargeable battery), it will be appreciated that the power allocated for running the algorithm is an important design consideration. Accordingly, algorithms are often developed and/or selected based on the amount of power that is likely to be consumed in running them as well as other considerations (e.g., how frequently an algorithm is likely to be run).

NeuroPace, Inc. is investigating a responsive neurostimulation system manufactured under the trademark "RNS SYSTEM" which includes an implantable component comprising a neurostimulator. (As may be appreciated by the implantable component's name, the RNS SYSTEM neurostimulator is capable of delivering electrical current stimulation to the patient, but this particular neurostimulator is also capable of processing signals received from the patient and device diagnostics which data then may be used by the implant to determine whether one of several actions should be taken, e.g., recording or storing data or delivering stimulation).

The RNS SYSTEM neurostimulator may be implanted in a hole cut out from a patient's cranial bone (sometimes referred to as a "defect" formed in the cranium). Alternatively, the neurostimulator component of an implantable responsive neurostimulation system may be implanted elsewhere in the patient, such as between the cranium and the scalp or in the pectoral region. The neurostimulator may be connected via one or more leads to a plurality of electrodes implanted in or on the patient's brain (e.g., the neurostimulator can be connected to one or two leads, and each lead may have four electrodes on a distal end thereof).

The neurostimulator is configurable to sense electrographic signals obtained from the patient at a predetermined sampling rate and to receive the signals on one or more channels. The neurostimulator or other component of the neurostimulation system may filter or otherwise condition (e.g., amplify and/or digitize) the signals. The signals received on each channel may be operated on by one or more algorithms, tools or detectors to identify characteristics in the data (e.g., characteristics that are believed to correspond to the electrographic onset of an epileptic seizure). Because in the RNS SYSTEM neurostimulator (and other neurostimulators) the power source for the neurostimulator is a battery contained in the implant (e.g., a primary cell battery or a rechargeable battery), the algorithms, or tools or detectors the neurostimulator uses to operate on the data desirably are selected to consume as little power as possible to achieve their objectives and therefore may be categorized generally as low computational complexity or "LCC" algorithms.

In the RNS SYSTEM, the algorithms or tools include a half wave detector, a line length detector and an area detector. The half wave detector generally may be characterized as a waveform morphology analysis tool and the line length and area detectors generally may be characterized as data reduction tools or as "power change" detectors.

An objective of a half wave detector may be to generate an output whenever the power of a portion of a signal falls within a particular frequency range. The particulars of how a half wave detector may be configured to operate in the context of a responsive neurostimulation system (or other diagnostic implantable medical device system) are described in more detail below with reference to example(s). Here it is noted generally that, even though a half wave detector is concerned with the frequency content of a signal, the tool operates in the time domain rather than in the frequency domain. For at least this reason, the half wave detector is considered to be an LCC algorithm relative to one that involves transformations into the frequency domain, such as fast Fourier transforms (or FFTs).

An objective of the line length detector may be to generate an output that corresponds to how much the frequency and/or amplitude of a portion of a signal within a particular time window is varying relative to, for example, a long term line length trend for that signal. The line length detector is sometimes referred to as a simplification of the fractal dimension of a waveform. The result of the line length detector is meant to correspond to an approximation of the overall power of the signal relative to a trend. For example, the line length detector is meant to "detect" when a portion of a signal in a given time window departs from the trend and exhibits a change in frequency or amplitude swings or both; a change in amplitude or frequency suggests something different is happening in the patient: for example, when the power increases, the line length detector may detect the onset of or a precursor to an electrographic seizure.

An objective of the area detector is to generate an output that corresponds to how much the integral (or area under a curve) of a signal within a particular time window is varying relative to, for example, a long term area trend for that signal. The area detector is sometimes referred to as a representation of the energy of a waveform. As with the line length detector, the area detector is meant to identify conditions when the signal departs significantly from the long term trend suggesting something undesirable or abnormal is occurring in the patient.

Each of the line length detector and the area detector is considered to comprise an LCC algorithm, since each requires little power to run relative to other, more complex algorithms that would provide a measure of how much a waveform is varying in terms of amplitude or energy.

Even though the half wave detector, the line length detector and area detector are each deemed to be algorithms of relatively low complexity, there nonetheless may be a significant number and kind of parameters that need to be specified in order for the running of each algorithm to have an optimal result.

A given system may be configured so that all or some of the parameters that control how an algorithm will operate (e.g., what sensed physiological data the algorithm will 'detect') are programmable by a user. In most circumstances, the "user" will be a physician diagnosing or otherwise treating the patient in whom the active implantable medical device is implanted. A system further may be configured so that one or more of the programmable parameters are set to "default" or other initial values at the time the system is manufactured or at the time the system is initially set up for a patient (e.g., in the operating room or during an initial post-op visit with a clinician).

The number and kind of parameters for a given tool may be relatively easy to understand and specify for an engineer or practicing scientist or for someone who otherwise is interested in how the algorithms operate at a detailed level. However, the typical user (e.g., a busy neurologist or a neurosurgeon with many patients) who is tasked with programming (or reprogramming, as the case may be) the tools may not have the time or inclination to develop a comprehensive understanding of what the various parameters are and how each relates to the condition or state of the patient the user wants the implant to monitor and/or treat. These users may be better served by system that allows a user to select what to detect graphically (e.g., on a display of a user interface with the implant and/or a database) and then automatically derives the parameters for the various tools based on what the user has selected.

The complexity of selecting parameters and parameter values for a tool may be illustrated with reference to the half wave tool (or half wave detector). A half wave tool may require a minimum of seven parameters to be specified, and may be associated with still other parameters that ought to be specified for optimum performance or which may be optional and best indicated for some circumstances and not others. In an example of a half wave detector discussed in detail here there are at least seven parameters that may be specified: (1) half wave hysteresis; (2) minimum half wave amplitude; (3) minimum half wave width; (4) half wave count criterion; (5) half wave window size; (6) qualified analysis window count; and (7) detection analysis window size. Each of these seven parameters may be associated with 1 to over 1000 discrete values.

It will be appreciated that, rather than learning what the "qualified analysis window count" parameter signifies and how to choose an appropriate value for it, a user may find it far easier to perceive a feature or pattern in a waveform in the graphical content of a signal sensed from a patient and then select it as something the user wants a tool to look for. A system with such a "graphical detection" feature would allow a user to configure the system to detect something (e.g., a pattern occurring in an electrographic signal) without needing to have a comprehensive understanding of how each parameter and associated parameter value will affect the operation or outcome of a given detection tool. For example, a user may be able to look at a display of a recorded EEG signal and conclude that the graphical content of the signal includes regions of highly rhythmic activity, and that he or she wants to configure one or more detection tools to detect that same pattern whenever it occurs in the patient. The user may want to accomplish this without having to understand what the detection parameters are and how each relates to the pattern the user wants to detect.

In some neurostimulation systems, the neurostimulator may be provided with at least three detection tools or algorithms that are available to and configurable by a user, namely, a half wave detector, a line length detector, and an area detector. Each of these algorithms is associated with a set of possible operating parameters.

The neurostimulator also can be configured to record signals sensed from the patient (or digital or other representations of the signals) and to record device diagnostics (i.e., information about the condition of the neurostimulator at certain times (e.g., whether an amplifier or amplifiers go into or out of saturation upon receiving an input signal from the patient)). As noted above, one or a combination of device diagnostics may serve as a proxy for something that is happening with the patient (such as a seizure).

The neurostimulator can communicate wirelessly with one or more devices external to the patient such as via telemetry. One of these external devices is in the control of the patient and may be referred to as a "patient remote monitor" or sometimes as a "patient initiating device." Another of these external devices is in the control of the user (e.g., a physician) and may be referred to as a "programmer." A wand may be necessary to establish an inductive telemetry link between the neurostimulator, on the one hand, and either the patient remote monitor or the programmer, on the other hand. In other cases, a link between the implanted component and one or more of the external components may be established by some other means that eliminates the requirement for a wand, such as by long range telemetry or some other wireless method of communication.

An external component such as a programmer may include a computer or central processing unit implemented in a wide variety of ways, such as a laptop computer, a tablet computer, a notebook computer, or a smartphone. Similarly, an external component that comprises a patent remote monitor may be implemented in the same way as a programmer (laptop, tablet, smartphone, etc.) or, since it may be required to have far less functions than a programmer, something simpler with a smaller form factor, such as a wrist watch or key fob or handheld device.

Using the inductive telemetry or other communications link, both the patient remote monitor and the programmer may be used to receive data that has been stored by the neurostimulator (e.g., recorded portions of electrographic signals or a device diagnostic reflecting information about a condition of the neurostimulator at the time an "event" was detected by an event detector). Once the data is on the patient remote monitor or the programmer, it may be stored locally on these devices. Alternatively, or additionally, data stored on the patient remote monitor or the programmer may be transferred elsewhere, such as to a central database.

A patient may have one-way access to such a central database, for example, by selectively connecting the patient remote monitor to the central database via a secure communications link such as a broadband connection (or a telephone "dial up" link) to transfer data from the implanted neurostimulator to the database. A user (e.g., a physician) may have bidirectional access to such a central database, for example, by selectively connecting the programmer to the central database to upload data from the neurostimulator (or from the neurostimulators of a physician's other patients) and to download data from the central database that the user can then beneficially use locally on the programmer in some fashion. For example, changes to the software the neurostimulator uses may be communicated from the central database to the programmers and then from the programmers to the implanted neurostimulators. In addition, a secure website may afford authorized users controlled access to parts of the central database or certain categories of data in the database.

The programmer also may be used to receive data in real time from the neurostimulator (for so long as the inductive telemetry link is established) and to selectively store the data received in real time for later review and other uses. In addition, and as the name of the component implies, the programmer can be used to program the neurostimulator, including but not limited to programming which parameters are used when a given algorithm is run and what values each parameter used in an algorithm will have.

The user generally will decide what type or types of physiological data (e.g., electrographic activity) he or she wants the neurostimulator to detect by reviewing records of electrographic activity for the patient. For example, the user may review electrographic activity previously recorded by the neurostimulator in order to select the nature and kind of activity that the user wishes the neurostimulator to detect in the future. Alternatively, or additionally, the user may review electrographic activity from the patient in real time to make decisions about what to detect. The user may also review electrographic activity recorded from the same patient or from different patients (e.g., with similar demographics) that are accessible from the central database.

A programmer may have features that allow a user to specify, among other things, parameters and parameter values for a particular detection tool, and then run the algorithms on previously-acquired records of electrographic activity. These simulations are intended to give the user examples of the nature and type of electrographic activity a given set of detection parameters and parameter values will detect.

In embodiments described here, systems and methods are provided with features that allow a user to review, on a display associated with one or more external components, physiological data acquired from a patient (either previously or in real time by one or more implantable components), and to select one or more regions of interest in the physiological data based on the graphical content on the region(s) of interest. These features collectively may be referred to herein as enabling "graphical detection."

Using the selected region(s) of interest as an input, the systems and methods are configured to automatically derive a set of parameters and values for the same that will be used by one or more detection algorithms. The intention is that, if the implantable component (e.g., the neurostimulator in the case of an RNS SYSTEM) is programmed with the automatically-derived parameter set, then when the relevant detection algorithm operates on physiological data acquired from the patient in the future, the algorithm will detect activity of the same nature and type as that which characterizes the user-specified region(s) of interest, if that nature and type of activity occurs while the algorithm is being run. The systems and methods therefore will assist the user in specifying the detection tool and a set of operating parameters for a given detection tool based on graphical content selected by the user. Thus the user will be relieved of some of the burden of having to first understand and then choose the detection tool and the values for the parameters associated with the detection tool (e.g., a value for a "detection analysis window size" parameter or a "hysteresis parameter" in a half wave detection tool). Indeed, in some embodiments, the user need not even characterize the type of activity that appears in the user-selected region(s), rather, the systems and methods will determine an activity type or pattern automatically.

In some embodiments, one or more "baselines" may be used by the system together with the region(s) of interest in automatically deriving the parameter values. These baselines may be selected automatically or by the user or some combination of the two.

After a user has selected region(s) of interest and/or baseline(s), the user can ask the system to automatically derive a set of parameters for, e.g., a detection tool, based on the selections. Then the user can run a simulation using, for example, the programmer or a website interface with a central database, in an effort to assess whether the detection tool with the automatically-derived set of parameters is likely to detect the patterns or other features that characterize the region(s) of interest that the user wants the detection tool to detect.

There are many possible sources for the signals used in such simulations. For example, the user may be able to select signals that were previously recorded and stored on the user's programmer or in a central database for the particular patient whose device the user is currently programming. These previously-recorded and stored signals may have been downloaded from the patient's active implantable medical device or may have been acquired while the patient's physiological activity was being monitored during some sort of diagnostic procedure before the implantable medical device was implanted (e.g., an in-hospital intracranial EEG monitoring procedure).

Alternatively, or additionally, a user may be able to access signals for running simulations from other patients the user is treating or from other patients other users are treating who have something in common with the user's patient. For example, signals for simulations may be drawn from a database of signals for patients with a common demographic as the user's patient, such as women having a particular neurological condition and who are between 18 and 25 years of age. Similarly, and for example in epilepsy, signals for simulations may be selected from a set of signals acquired from patients with the same seizure focus (e.g., a seizure focus in the temporal lobe, a seizure focus in a hippocampus). Signals used for simulations that are associated with other patients may be retrievable from the user's programmer or from a central database. They may be anonymized or "de-identified" to protect patient privacy, or the signals may be averaged for a given population or otherwise adjusted or filtered for use in simulations of the type contemplated herein.

In still other instances, a user may be able to run a simulation of a detection tool using an automatically-derived set of parameters on signals being acquired in real time from the patient's active implantable medical device. For example, during a patient's visit to the doctor's office, the doctor may establish a communications link between the doctor's programmer and the patient's active implant, select a region or region(s) of interest, ask the system to automatically derive a set of parameters for the relevant detection tool, and then run a simulation on the programmer of the detection tool with the automatically-derived parameters on signals being acquired in real time from the patient's active implant to assess what patterns and features likely will be detected if the doctor reprograms the patient's active implant with the automatically-derived parameter set.

Based on the foregoing, it will be appreciated that a user can use simulations to gauge whether a given automatically-derived parameter set is likely to result in detection of what the user wants the implantable component to detect. If the user is not satisfied with the simulation, the user can reject the automatically-derived set and start over, for example, by changing the region(s) of interest or by selecting a different region of interest or regions of interest and/or a different baseline or baselines. If the user is satisfied with the simulation, then the user can accept the automatically-derived set and subsequently program the implantable component with the set (e.g., use an RNS SYSTEM programmer to program the implanted neurostimulator with the set via the wand and an inductive telemetry link).

Alternatively, in some embodiments, when the user is less than completely satisfied with the results of a simulation (and thus with an automatically-derived set of parameters), the user may be provided with the option of adjusting one or more parameter values (for example to detect a particular pattern earlier or later (e.g. within the first second of activity or after the first second) or to detect more or less of a particular feature (e.g. detect higher amplitude signals or lower amplitude signals) and then instructing the system to generate another set reflecting the adjustment. For example, the system may allow the user to adjust a "pattern duration" characteristic so that the automatically-derived parameters will be biased toward detecting activity that lasts longer than (or shorter than) the duration with which a region of interest is characterized. Similarly, the system may allow the user to adjust a "signal amplitude" characteristic so that the automatically-derived parameters will be biased towards detecting more (or less) activity that is characterized by the same type of activity with which a region of interest is characterized but with a with lower or higher amplitude threshold. The sensitivity adjustments may be offered to the user based on what the systems and methods infer that the user is likely to see in the region of interest that the user wants the detection tool to detect (e.g., rhythmic activity, spiking activity, a change in power of the signal, etc.).

Particular configurations of a system may offer a user the opportunity to make different or additional sensitivity adjustments, such as to fine-tune the frequency range a given detection tool will detect in a signal. Instructions on how to use a particular sensitivity adjustment and/or the likely effect of moving in one direction or the other (i.e., more or less sensitive), may be described for the user in the context of the simulation itself (e.g., on the programmer) and/or in a user's manual. A system may be configured to play on a programmer or over a website a demonstration of how a user might select region(s) of interest, baselines, signals on which to run simulations, and then how a user might use the available sensitivity adjustments to refine a set of automatically-derived parameters to best satisfy the user's intentions regarding detection and his or her patient.

Embodiments in which systems or methods automatically derive a set of parameters values and/or automatically select which parameters to use, for a half wave detector will now be described with reference to FIGS. 1-24.

A half wave detector (sometimes referred to as a type of "waveform morphology analyzer"), looks for and counts "half waves" when they occur in a predetermined window of time in an electrographic signal (e.g., a signal corresponding to a time-varying field potential difference between two electrodes, at least one of which is implanted in or on a patient's brain). What constitutes a half wave that should be counted is defined so that the counts that result from running the algorithm roughly correlate to the power of the signal at a particular dominant frequency (or in a particular frequency band). A half wave detector is useful, for example, in applications of an implantable medical device system to detect electrographic activity corresponding to epileptiform activity or the onset of a seizure. It should be appreciated that a half wave detector may be used in analyzing waveforms corresponding to physiological data sensed from a patient for different types of activity or different features in the sensed data. For example, when the patient has epilepsy, some instances of a waveform analyzer implemented as a half wave detector may be configured to detect rhythmic activity when it occurs in electrographic signals monitored from the patient and other instances of a waveform analyzer implanted as a half wave detector may be configured to detect spike complexes when these occur in the electrographic signals. Thus, the parameters and the values for the parameters may vary for different iterations of the same detection tool, depending upon the nature and type of activity each iteration of the tool is intended to detect.

With reference to FIG. 1A, in one embodiment of a half wave detector 190, there may be seven programmable parameters to define the half wave detection: namely, a half wave hysteresis parameter 191, a minimum half wave amplitude parameter 192, a minimum half wave width parameter 193, a half wave count criterion parameter 194, a half wave window size parameter 195, a qualified analysis window count parameter 196, and a detection analysis window size parameter 197. These seven parameters may be thought of as being part of the "parameter space" for a tool to detect half waves in a signal.

"Half waves" generally, as well as half wave hysteresis, will now be described with reference to FIGS. 1B and 2. A waveform 100 corresponds to an electrographic signal after the electrographic signal has been pre-processed and quantized (i.e., subjected to pre-processing and conditioning such as filtering to remove low and high frequency energy and sampling by an analog-to-digital converter). The y-axis corresponds to units of amplitude (which may ultimately be correlated to voltage or current), and the x-axis corresponds to units of time, more particular, fractions of a second.

Figure 1B:
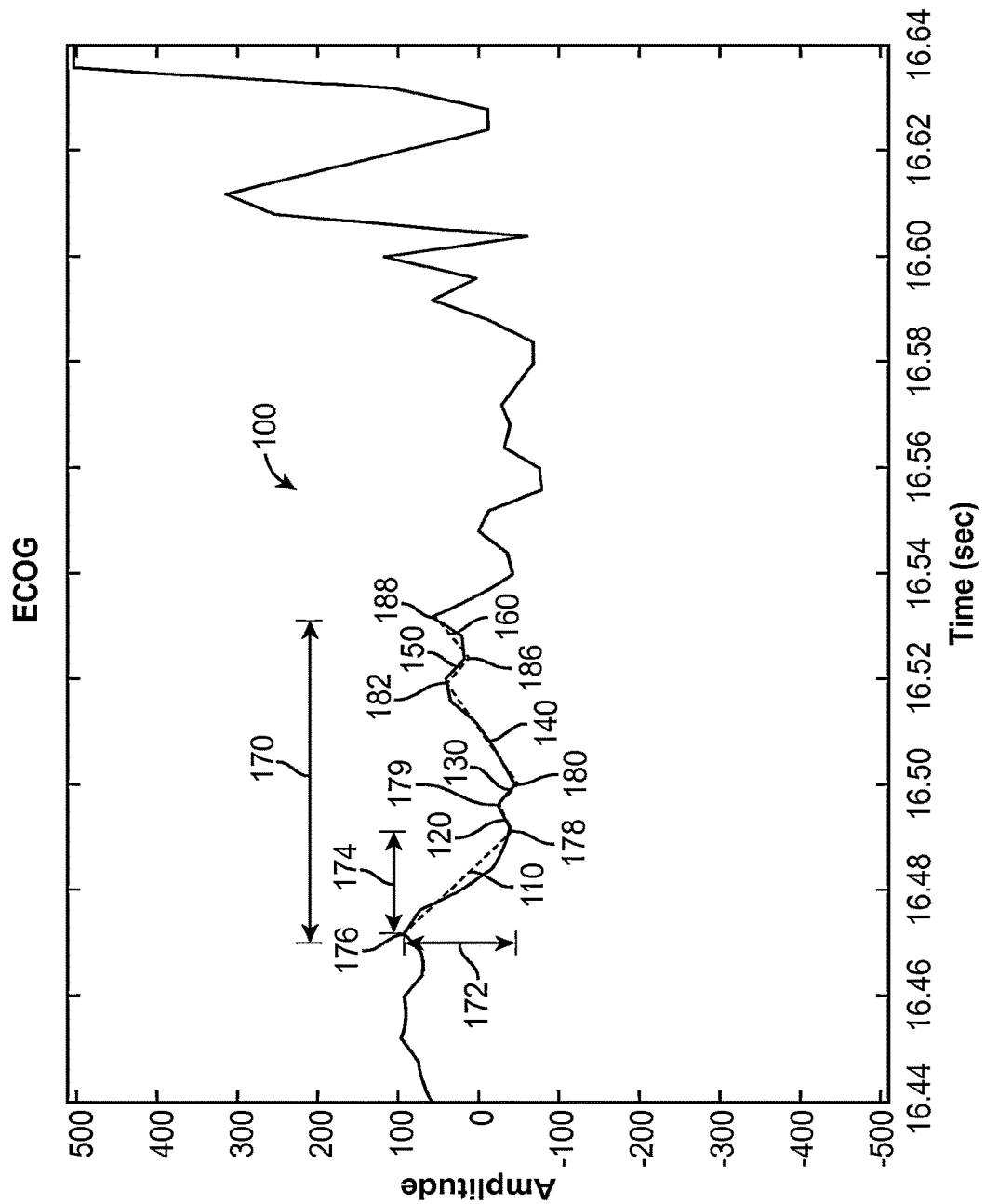
FIG. 1B is a graph of a time-series representation of an electrographic signal exhibiting a plurality of transitions in the direction of the signal.

If a half wave of the waveform is defined generally as the excursion of the signal over time from a local minimum to a next local maximum or, alternatively, from a local maximum to a next local minimum, it will be appreciated that in FIG. 1B there are six half waves 110, 120, 130, 140, 150, and 160 (associated with the dashed lines) in the waveform segment 170 that extends over about a 60 ms interval between about 16.47 and 16.53 s.

A given half wave may be characterized by an amplitude and a width, such that a half wave amplitude is the difference between the local maximum and minimum amplitudes, and the half wave width is the period of time from the beginning of a half wave to the end of the half wave. A half wave further may be characterized by a direction based on whether the slope of the half wave is positive or negative (determined from the positions of the starting point and ending point of a given half wave on the horizontal axis as compared to the vertical axis). In FIG. 1B, for example, the half wave 110 has an amplitude 172 of about 130 units (from about +100 units to about −30 units), a width 174 of about 20 ms (from about 16.47 s to about 16.49 s), and a negative slope. Accordingly, in FIG. 1B, a half wave #1 110 may be represented by a vector corresponding to the dashed line from the local maximum at the starting point 176 to the next local minimum at the ending point 178. At the point 178, the waveform changes direction, with a positive slope towards point 179 that marks the end of the half wave #2 120 and the beginning of the half wave #3 130. The points 180, 182, 186, and 188 define the end of the half wave #3 130 and the beginning and end of the half wave #4 140, the half wave #5 150, and the half wave #6 160, respectively.

It may be desirable to configure a given half wave algorithm to ignore some half waves that are deemed to be insignificant variations (or small perturbations) in the waveform so that these will not, in fact, be recognized by the detection tool as half waves. In a half wave detector, this may be accomplished by defining a value for a hysteresis parameter 191 in the half wave detection algorithm. In FIG. 1B, features of the waveform that are deemed to constitute insignificant variations in the electrographic signal might correspond to the half wave #2 120, the half wave #3 130, the half wave #5 150, and the half wave #6 160. These half waves might be, for example, deemed to be inconsistent with the overall movement of the electrographic signal, and/or attributed to perturbations in the signal that result from quantizing of noise or other low-amplitude signal components of the sensed physiological signal.

Thus, a hysteresis setting may correspond to allowing some half waves in the direction of movement of the waveform to be disregarded and thus not treated as a reversal of direction that warrants identifying the reversal of direction point as the starting (or ending) point of a half wave. A hysteresis allowance in a detection algorithm can be used, for example, to avoid having to subject the physiological signals being sensed from the patient to more rigorous processing and conditioning before the signals are introduced to the algorithm.

Figure 2:
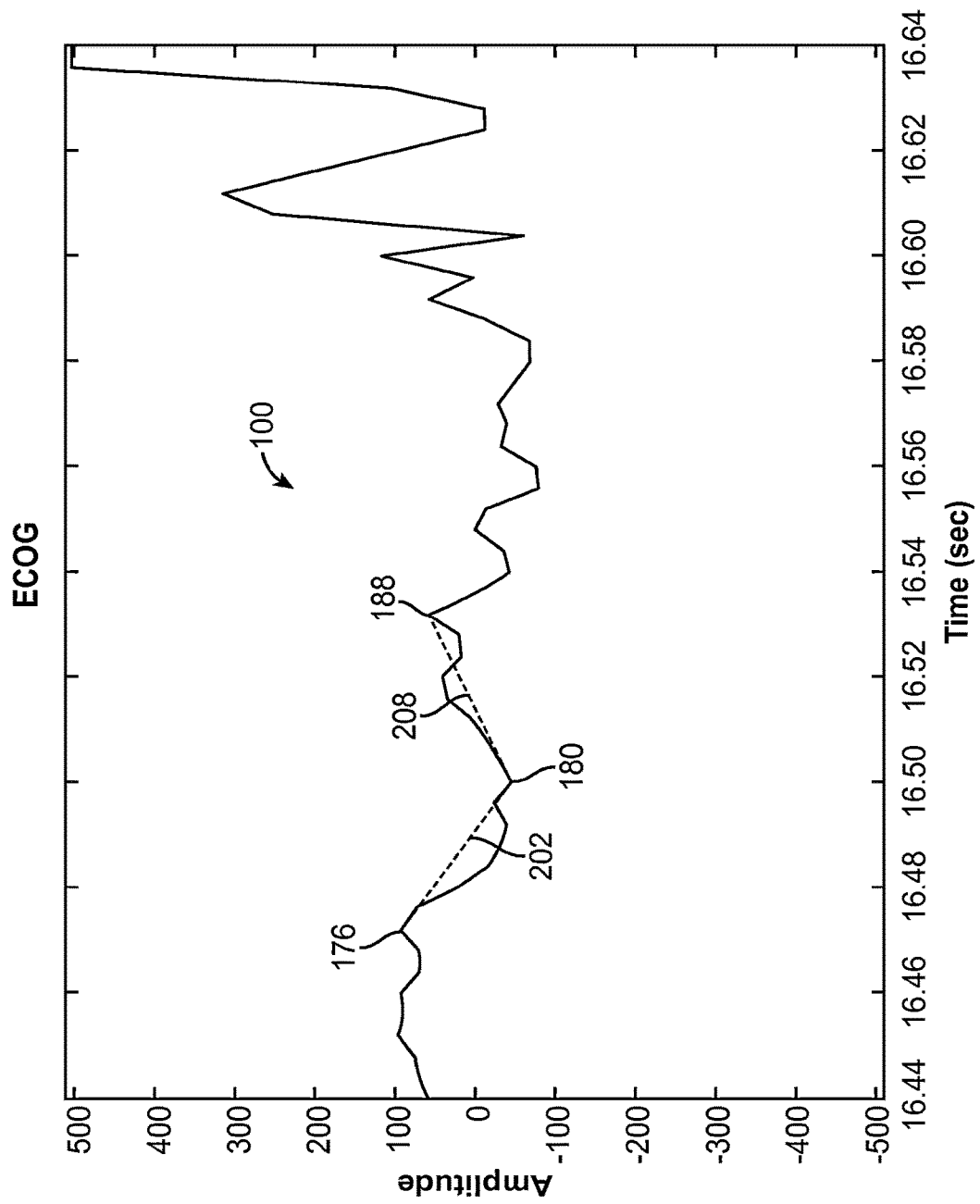
FIG. 2 is the graph of FIG. 1B in which two half waves are identified.

The effect of specifying a value for a hysteresis parameter may be appreciated with reference to FIG. 2. FIG. 2 represents the same waveform 100 of FIG. 1B, but now there are only two dashed lines representing vectors corresponding to two half waves in the waveform segment 170. More particularly, one half wave 202 (hereinafter referred to as second half wave 202 in FIG. 3) extends from a starting point 176 to an ending point 180, and another half wave 208 (hereinafter referred to as third half wave 202 in FIG. 3) extends from the point 180 to another half wave ending point 188. In this example, the half wave hysteresis parameter 191 has been set to specify a minimum amplitude that the waveform has to exceed when it transitions from one direction to the other (e.g., positive to negative slope) before the half wave will be considered to represent the start or end of a half wave. More specifically, in the example of FIG. 2, the half wave hysteresis parameter 191 has been set to a value of 50 amplitude units such that, if after the signal comprising the waveform changes slope, the amplitude of the half wave never exceeds 50 amplitude units before it changes slope again, no half wave will be deemed to have ended or begun. Since the half wave #2 120, the half wave #3 130, the half wave #5 150 and the half wave #6 160 shown in FIG. 1B each are characterized by an amplitude of less than 50 units, when the half wave hysteresis parameter has been set to a value of 50 amplitude units, each of these half waves will be ignored in determining which and how many half waves are present in the waveform segment 170. Thus, the half wave 202 (the second half wave 202 in FIG. 3) has an amplitude of about 150 units (from about +100 units to about −50 units on the vertical y-axis) and a half wave width of about 30 ms (from about 16.47 s to about 16.50 s), and a negative slope. The half wave 208 (the third half wave 208 in FIG. 3) has an amplitude of about 100 units (from about −50 units to about +50 units) and a half wave width of about 30 ms (from about 16.50 to about 16.53 s) and a positive slope.

In addition to using parameters and values for the same to decide when a half wave will be deemed to begin and end, parameters are used to determine which half waves occurring in a given processing window are to be considered "qualified half waves," such that they will be treated in a particular way by the algorithm. A processing window may be defined as being that which is appropriate for the circumstance, given the specifications of the relevant hardware and software. By way of example, a processing window specified for a half wave detector may correspond to a 128 ms window, which may in turn represent 32 samples of the physiological data (e.g., of an electrographic signal sensed from the patient) at a 250 Hz sampling rate.

Figure 3:
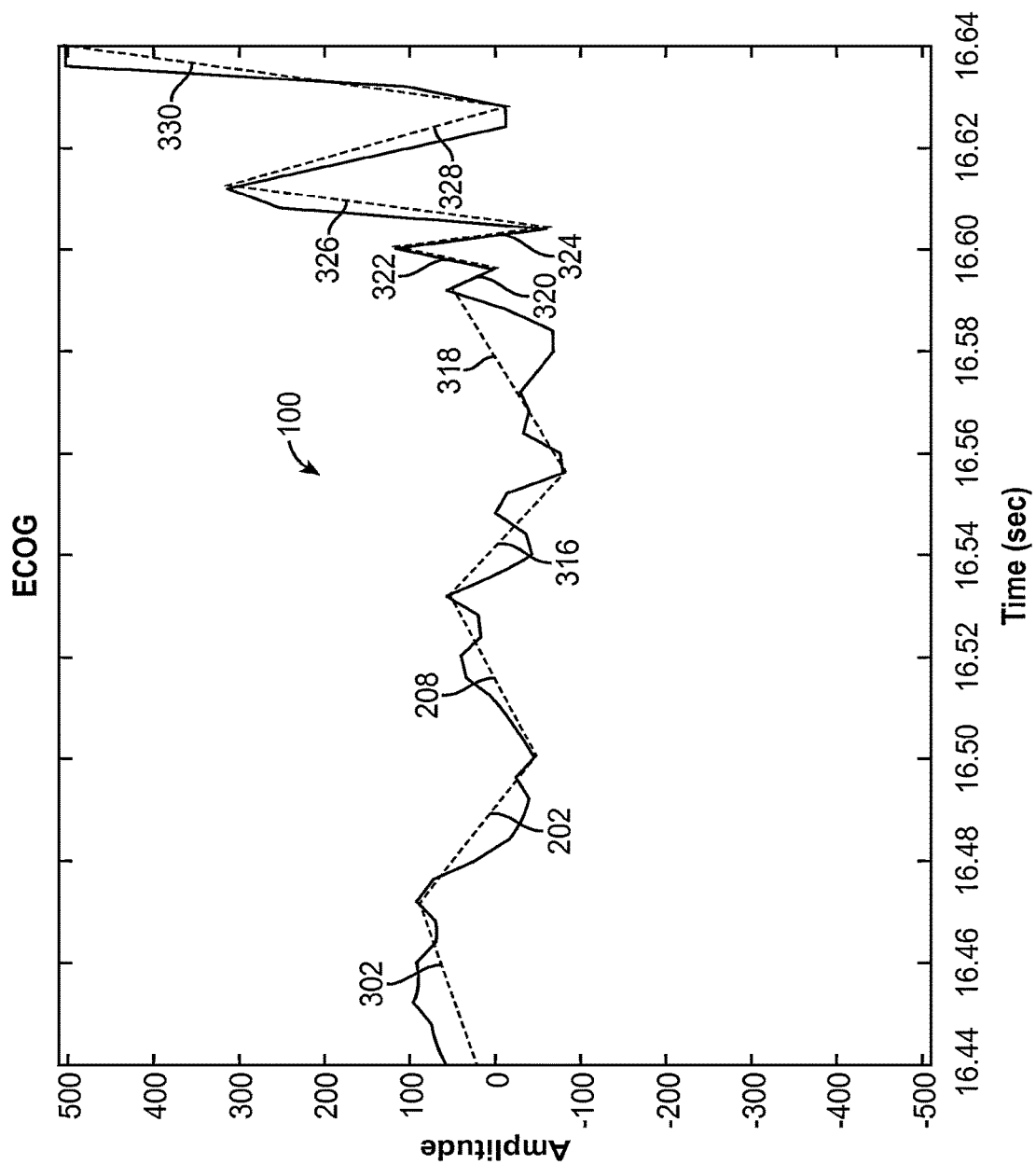
FIG. 3 is the graph of FIG. 1B in which a set of eleven half waves are identified.

Generally, a half wave will be considered a "qualified half wave" if its amplitude exceeds the value selected for a minimum half wave amplitude parameter 192 and a minimum half wave width parameter 193. The range of values from which a value for the minimum half wave amplitude parameter 192 may be selected normally will be consistent with the range of possible amplitudes for the waveform corresponding to the sensed physiological data. In the example of FIG. 3, and with reference to the y-axis of FIG. 3, the range of possible amplitudes is +/−512 units of amplitude.

The minimum half wave width parameter 193 is the parameter that determines what maximum frequency represented in the waveform will be detected by the half wave detector. The range of values from which a value for the minimum half wave width may be selected normally will be between 0 ms (corresponding to 125 Hz for a sampling rate of 250 Hz) and 400 ms (corresponding to approximately 1 Hz for a sampling rate of 250 Hz). Selection of a value for the minimum half wave width parameter 193 will be driven, at least in part, by the rate at which the data is sampled by the system. In an example, if a signal is being sampled at 250 Hz, then each sample will be 4 ms apart. If the value of the minimum half wave width is set at 4 ms, then each half wave would have to last longer than 4 ms in order to be considered a qualified half wave. Since each sample is 4 ms, then a qualified half wave would have to endure for two samples, which would correspond to an effective minimum half wave duration of 8 ms. If a whole wave is defined as comprising two consecutive qualified half waves characterized by opposite slopes, then a whole wave would have to be represented by four samples of 4 ms each, or 16 ms total.

For an electrographic signal sensed from a patient and quantized by a neurostimulator such as the RNS SYSTEM, the frequency of the signal may be approximated as the inverse of the duration of a whole wave. In an example, if a whole wave takes four 4 ms samples to be represented, and since $1/16$ ms is 62.5 Hz, a half wave detector with the value of the minimum half wave width parameter set at 4 ms will not be configured to detect the activity in an electrographic signal that is characterized by a frequency of greater than 62.5 Hz.

Referring now to FIG. 3, the waveform 100 is shown extending from about 16.44 s to about 16.64 s (or for about 200 ms). The half wave hysteresis parameter 191 is set at 50 units, such that a transition in the waveform that corresponds to an increase or decrease in amplitude of less than 50 units will not be identified as a discrete half wave but rather will be included as part of a greater amplitude half wave. There are eleven half waves in the waveform 100, namely, a first half wave 302, the second half wave 202 (first shown in FIG. 2), the third half wave 208 (first shown in FIG. 2), a fourth half wave 316, a fifth half wave 318, a sixth half wave 320, a seventh half wave 322, an eighth half wave 324, a ninth half wave 326, a tenth half wave 328, and an eleventh half wave 330.

If the minimum half wave amplitude parameter 192 is set at a value of 100 units and the minimum half wave width parameter 193 is set at a value of 4 ms, then with reference to Table 1 below, only seven of the eleven half waves in the waveform segment 300 will constitute "qualified half waves," namely, the second half wave 202, the third half wave 208, the fourth half wave 316, the fifth half wave 318, the ninth half wave 326, the tenth half wave 328, and the eleventh half wave 330. That is, only seven of the eleven half waves meet or exceed the thresholds of both the minimum half wave amplitude parameter 192 and the minimum half wave width 193.

TABLE 1

|  | First Half Wave 302 | Second Half Wave 202 | Third Half Wave 208 | Fourth Half Wave 316 | Fifth Half Wave 318 | Sixth Half Wave 320 | Seventh Half Wave 322 | Eight Half Wave 324 | Ninth Half Wave 326 | Tenth Half Wave 328 | Eleventh Half Wave 330 |
|---|---|---|---|---|---|---|---|---|---|---|---|
| Minimum Half Wave Amplitude (100 counts)? | No | Yes | Yes | Yes | Yes | No | Yes | Yes | Yes | Yes | Yes |
| Minimum Half Wave Width (4 ms)? | Yes | Yes | Yes | Yes | Yes | No | No | No | Yes | Yes | Yes |
| Qualified Half Wave? | No | Yes | Yes | Yes | Yes | No | No | No | Yes | Yes | Yes |

For example, while the first half wave 302 exceeds the 4 ms threshold value for the minimum half wave width parameter 193, it does not also exceed the 100 count threshold value for the minimum half wave amplitude parameter 192, so the first half wave 310 is not identified as a qualified half wave. Similarly, the sixth half wave 320 exceeds the 100 count threshold value for the minimum half wave amplitude parameter 192, but it does not exceed the 4 ms threshold value for the minimum half wave width parameter 193, so the sixth half wave is not identified as a qualified half wave. Each of the second half wave 202, the third half wave 208, the fourth half wave 316, the fifth half wave 318, the ninth half wave 326, the tenth half wave 328, and the eleventh half wave 330 satisfy both the minimum half wave amplitude parameter 192 and minimum half wave width 193 thresholds, so each of these seven half waves is identified as a qualified half wave.

Two other parameters that may be specified for a half wave detector relate to the how much of a given frequency has to occur, at a minimum, in a particular time period in order for the algorithm to determine whether to register something as having been 'detected' (e.g., the onset of epileptiform activity in the patient). These two parameters will be described with reference to FIG. 4 and include a half wave count criterion parameter 194 and a half wave window size parameter 195. The half wave count criterion parameter 194 and the half wave window size parameter 195 allow a half wave detector to identify a "qualified analysis window". Generally, the number of qualified half waves has to exceed the value selected for the half wave count criterion parameter 194 during the time window defined by the value selected for the half wave window size parameter 195, in order for the algorithm to consider the circumstance a detection-worthy circumstance. When, in a given half wave window with a duration specified by the half wave window size parameter 195, the number of qualified half waves exceeds the value for the half wave count criterion parameter 194, then that analysis window which contains the end of the half wave window is considered a "qualified analysis window".

In one example, a value of 9 might be set for the half wave count criterion parameter 194 and a value of 1 s (1000 ms) may be set for the half wave window size parameter 195. In the algorithm, these values would mean that at least 10 qualified half waves have to occur in 1 s (or at least five whole waves in 1 s) in order for the minimum frequency criteria for detection to be considered to have been met (five whole waves in one second corresponds to a frequency of 5 Hz).

Figure 4:
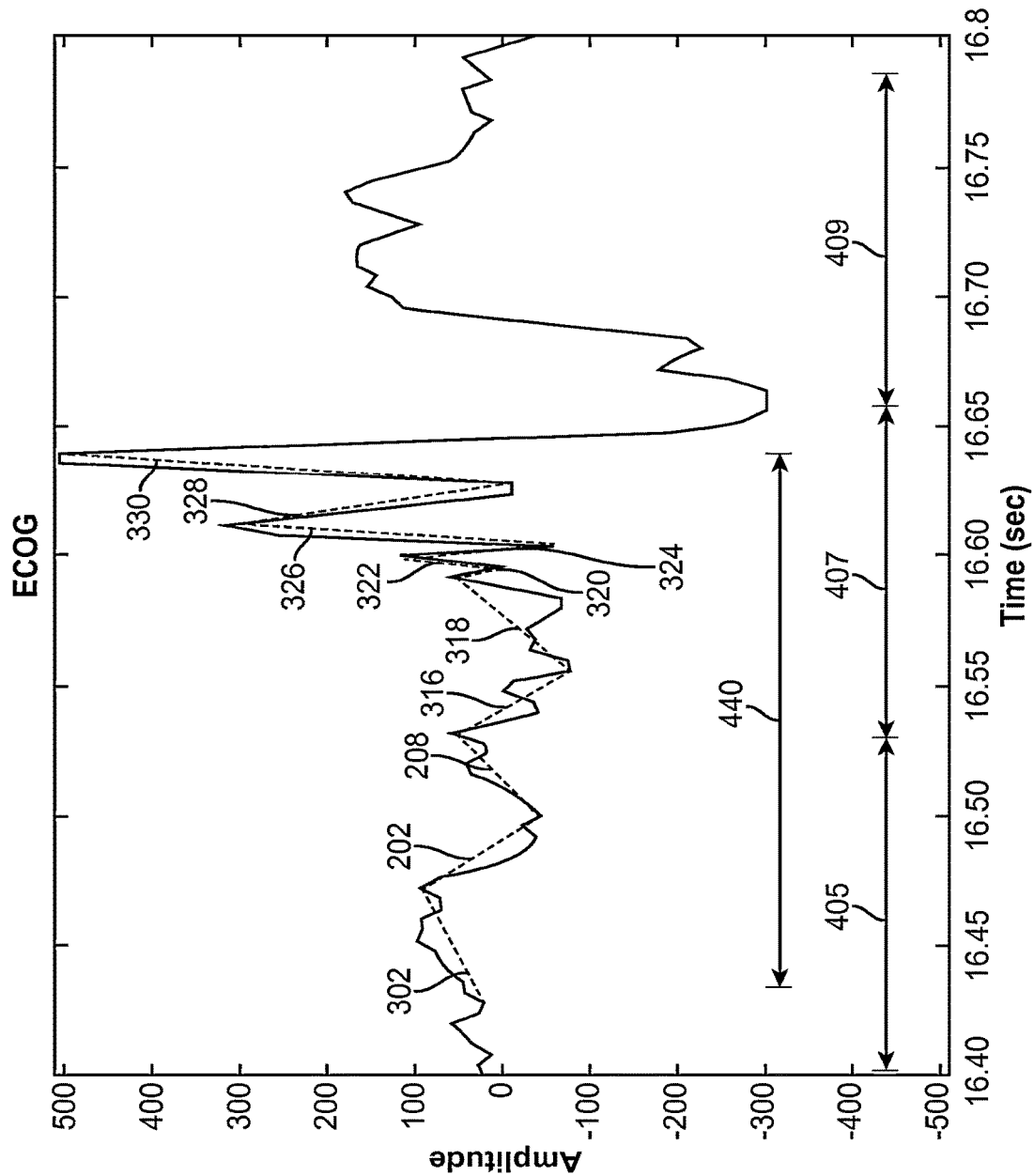
FIG. 4 is the graph of FIG. 3 in which parameters of a method for identifying a minimum frequency are illustrated.

In another example, a value of 6 might be set for the half wave count criterion 194 and a value of 200 ms might be set for the half wave window size 195. Referring now to FIG. 4, at the base of the graph along the x-axis (time in seconds), three sets of double-headed arrows indicate three consecutive processing or analysis windows of 128 ms each, namely, analysis window #1 405, analysis window #2 407, and analysis window #3 409. Analysis window #1 405 begins at about 16.40 s and ends at about 16.53 s, analysis window #2 407 runs from about 16.53 s to about 16.66 s, and analysis window #3 409 runs from about 16.66 s to about 16.79 s.

Based on a half wave hysteresis parameter 191 set at 50 units of amplitude, minimum half wave amplitude parameter 192 set at 100 counts, and a minimum half wave width parameter 193 set at 4 ms, the algorithm identifies and counts qualified half waves within a 200 ms half wave window 440 that ends at about 16.64 s. Since there are seven qualified half waves in the 200 ms half wave window 440 (see also FIG. 3 and Table 1 and the descriptions thereof), then the minimum frequency for detection has been met (more than 6 qualified half waves counted in a half wave window of 200 s). When the seventh qualified half wave occurred, the system was in the second 128 ms analysis window shown in FIG. 4, or analysis window #2 407. Thus, analysis window #2 407 is a "qualified analysis window".

In some embodiments, a half wave detector may allow values for two additional parameters to be specified which are used in an effort to make the algorithm detect only those patterns occurring in a waveform that exhibit a certain consistency and duration. These parameters are the qualified analysis window count (X) 196 and the detection analysis window size (Y) 197. The values for these parameters are selected so that the half wave detector will only deem a detection-worthy circumstance to exist if a sufficient number (X) of qualified analysis windows have appeared in Y of the most recent analysis windows.

This type of analysis generally may be referred to as an "X of Y" criterion. Such an "X of Y" criterion may be used in the half wave detector described here to avoid having the detector trigger on circumstances that are considered too spurious to warrant detection. In an example, a value for the qualified analysis window count 196 parameter may be 2 and a value for the detection analysis window size 197 may be 1024 ms (where the detection analysis window size represents a number of consecutive analysis windows of equal size (for example, eight consecutive analysis windows of 128 ms would correspond to a detection analysis window size of 1024 ms).) With these values, applying an "X of Y criterion" would mean that the minimum frequency for detection (minimum number of qualified half waves occurring in the half wave window size) would have occurred in at least two of the eight most recent 128 ms-analysis windows in order for the algorithm to deem a circumstance to exist that is worthy of detection.

A half wave detector is just one of several possible algorithms or tools that may be applied to physiological data (e.g., electrographic signals sensed from electrodes placed in or on a patient's brain) in order to determine whether a condition of interest (e.g., a certain pattern of activity) occurs in the data. Multiple algorithms may be used in combination to analyze the same data, or additional algorithms may involve comparing or contrasting the results of analyzing data with one tool with the results of analyzing different data (e.g., data occurring later in time or data sensed from a different channel or from a different type of sensor (and/or using a different sensing modality, such as voltammetry rather than field potential measurements)). The output of one or more algorithms such as a half wave detector output may be used as one or more inputs to a finite, time-dependent state machine for determining whether a pattern or patterns occur in a particular sequence or sequences.

It will be appreciated that, even in a simple case, where only a half wave detector is used to analyze an electrographic signal sensed from the patient, it is a non-trivial task to accurately specify the values for the seven parameters used by the algorithm (namely, the half wave hysteresis parameter 191; the minimum half wave amplitude parameter 192 and the minimum half wave width parameter 193 (for identifying qualified half waves and establishing the maximum frequency for detection), the half wave count criterion parameter 194 and the half wave window size parameter 195 (for establishing a minimum frequency for detection); and the qualified analysis window count parameter 196 and the detection analysis window size parameter 197 (for establishing an "X of Y criterion" for detection).

It is not an intuitive exercise for a user to look at an existing time-series electrocorticographic signal (or a spectrogram of such a signal) and to decide what values to assign to each of these seven parameters in order to tune a half wave detector so that it will detect in future signals a particular type of activity that is represented in the existing signal. It is true that systems like the RNS SYSTEM allow a user to "test run" algorithms with a given set of parameter values using a simulator and display provided in an external component (i.e., a "programmer") before the parameter values are actually programmed into the patient's implanted neurostimulator. Nevertheless, the lack of intuitiveness of the process of matching up the type of activity or pattern the user can see on a display with the appropriate values, for example, for the "half wave count criterion parameter" and the "half wave window size parameter", often requires some trial and error before the user is satisfied that a given set of values will detect what the user wants the implanted neurostimulator to detect when next that activity actually occurs in the patient. Thus, a system would be more user-friendly if the selection of parameter values for a given algorithm used in detection was an automated process or at least a partially automated process.

Figure 5:
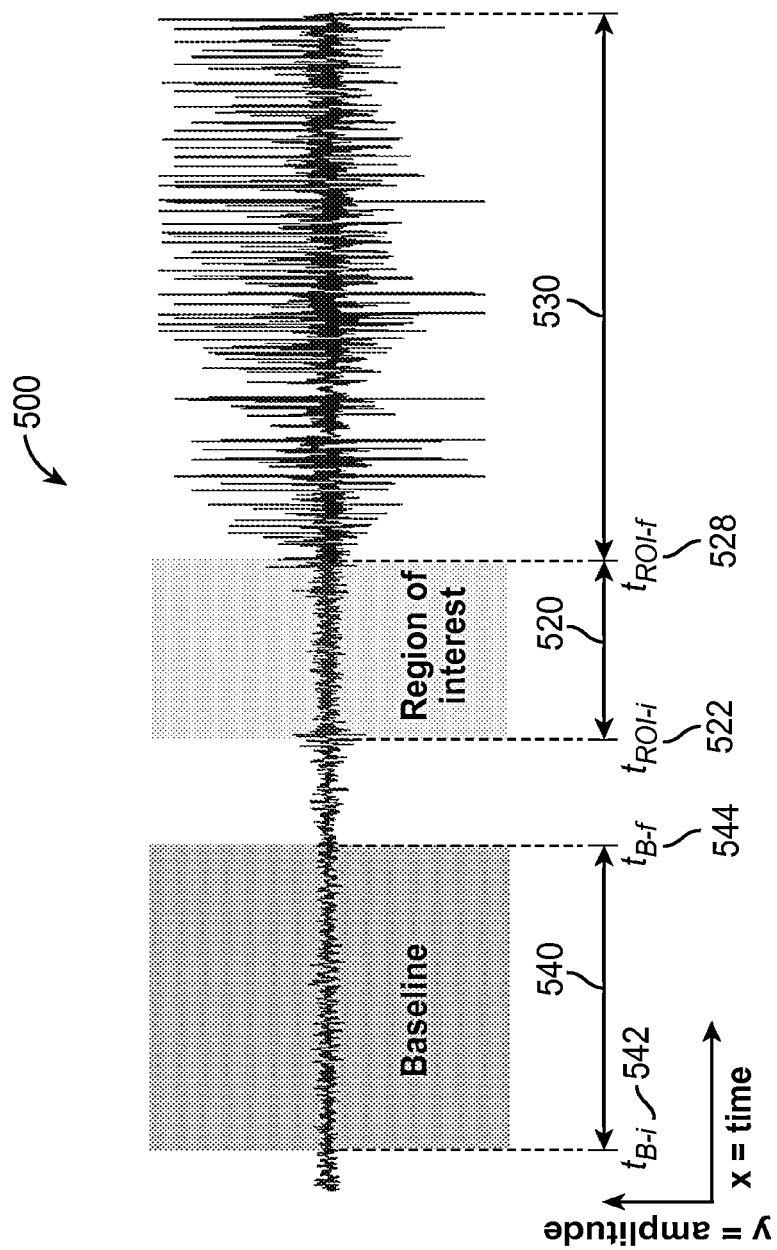
FIG. 5 is a graph of a time-series representation of an electrographic signal exhibiting a plurality of regions, including a region of interest, a region of seizure activity, and a region of baseline activity.

FIG. 5 is an example of an electrographic signal 500 that might be sensed from a patient and processed by an implantable neurostimulator. For instance, a signal such as that shown in FIG. 5 might correspond to a signal acquired such as on an active sensing channel of implantable medical device which is configured to receive a bipolar signal representative of the difference in electrical potential between two selectable electrodes, at least one of which is implanted in or on the patient's brain (the second electrode may also be implanted in or on the patient's brain (e.g., on the same distal portion of a lead as the first electrode) or may be a reference electrode (e.g., the conductive outer housing of the neurostimulator)). A signal of the type shown in FIG. 5 may be retrieved from a memory of the implanted neurostimulator or of the external programmer component or from the central database. Alternatively, the signal shown in FIG. 5 may correspond to that which is captured on a screen while the signal is being monitored in real time by an external component that is in wireless communication with an implanted neurostimulator.

The graph of FIG. 5 is a time-series representation of the electrographic signal, with the x-axis representing time and the y-axis representing the amplitude of the signal. A user familiar with reviewing electrocorticographic data from a patient of this sort may easily be able to identify a region of interest or "ROI" based on the graphical content of the signal, for example, a region of interest demarcated by the double-headed arrow 520 and beginning at a time of about time $t_{ROI-i}$ 522 and lasting until about time $t_{ROI-f}$ 528. In this particular example, a typical user would likely appreciate that the graphical content of the region of interest 520 includes high rhythmic activity as compared to a baseline level of activity and which precedes higher amplitude synchronous activity, which is often typical of seizure activity as recorded using intracranial electrodes. (In some systems, such as the RNS SYSTEM, detection may be used as a trigger for some therapeutic action, such as delivering electrical current stimulation to the patient from the neurostimulator in an effort to interrupt a seizure or to prevent it from fully developing. In these systems, then, and as in the example of FIG. 5, a region of interest 520 may be selected as one that defines the transition between non-seizure activity and seizure activity, in other words, the onset of a seizure. In a situation where detection is undertaken as part of a diagnostic process (as opposed to being used as a trigger for delivering therapy), then a region of interest may be selected by a user that is within the seizure activity region 530.)

In FIG. 5, the region indicated by the double-headed arrow 530 may be deemed to be a region corresponding to seizure activity, and the region indicated by the double-headed arrow 540 may be deemed to be a region corresponding to baseline activity. The baseline activity region 540 may be one that begins at a time of about $t_{B-i}$, and extends until at least a time of about $t_{B-f}$. (In some embodiments, the length of time over which the baseline activity occurs is less relevant than the nature of the activity occurring within that time period, as will be apparent from the description below.)

Figure 22A:
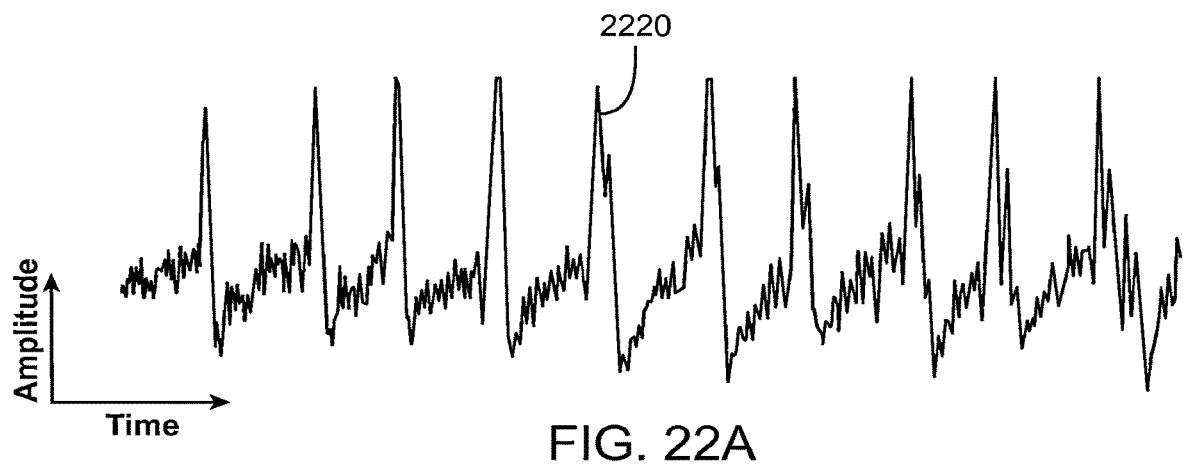
FIG. 22A, FIG. 22B, and FIG. 22C each is a graphical representation of a combination of a rhythmic type of activity and a spiking type of activity as may occur in electrographic signals sensed from a patient.
Figure 22B:
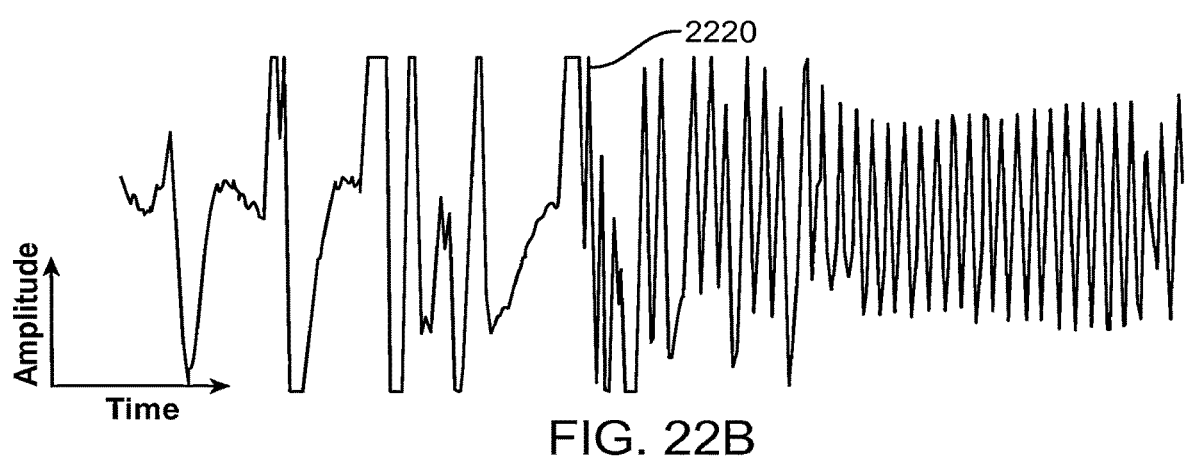
Figure 22C:
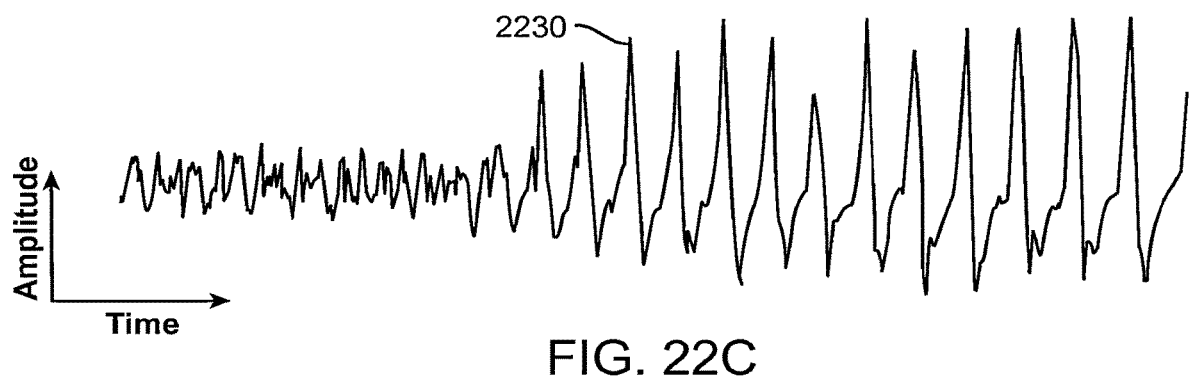

It should be appreciated that FIG. 5 is intended to illustrate generally a region of interest 520 and generally a region of baseline activity 540 in a signal, and that the actual makeup or content of a region of interest 520 and the actual makeup or content of a region of baseline activity 540 may vary widely from application to application, based, for example, on the objectives of the user/physician with respect to his or her patient(s). More particularly, the region of interest 520 in FIG. 5 is meant to represent a region of highly rhythmic activity. In other applications, or in the same application but for other instances of a detection tool, a region of interest may constitute a type of activity other than rhythmic activity or a type of activity that includes both rhythmic activity and another type of activity. For example, described below with reference to FIG. 22C is a circumstance in which a region of interest is selected that exhibits one or more spike complexes, alone or in combination with rhythmic activity. Generally, in systems and methods according to embodiments, a user can select a region of interest based on its graphical content, without regard to the set of operating parameters for a detection tool that might be used to detect that graphical content. Put another way, a user can use graphical detection to program the implant as to what it ought to detect, without an in depth understanding of the parameters a detection tool needs to actually accomplish such detection.

In some embodiments, a user may be able to select a region of interest in a given electrographic signal by clicking and dragging a mouse over the display of the electrographic signal on an external component such as the programmer or on a web page of a website. Other methods of selecting a region of interest will be apparent (such as using fingers or a stylus to make a selection on display of a "touch screen", or by using key strokes on a keyboard, etc.).

In some embodiments, the user may also be able to select one or more regions of baseline activity 540 by clicking or dragging or otherwise. Alternatively, or additionally, a region of baseline activity 540 may be automatically selected by the system or set to some default value or range of values by the system. If the system selects a region of baseline activity 540, then the system ultimately may or may not use the baseline activity region selected in automatically deriving a parameter set. For example, if the system initially selects a region of baseline activity 540 that turns out to be not that much different than the content of a region of interest 520 in one or more respects, then the system ultimately may not base the derivation of any parameter in the parameter set on what is contained in a baseline activity region 540.

Figure 6:
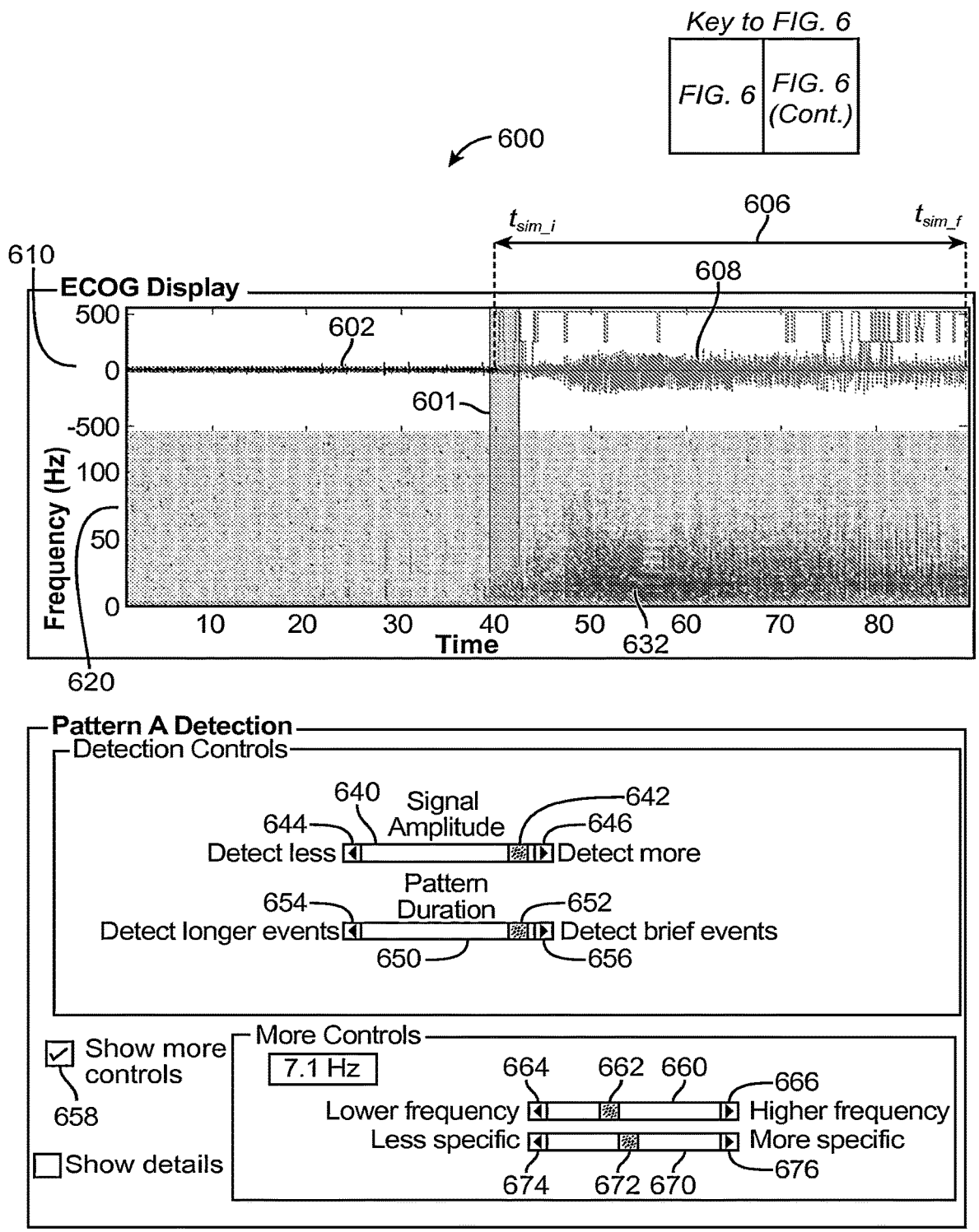
FIG. 6 is a representation of a display according to some embodiments corresponding to a simulation in which a half wave detector is run on selected electrocorticographic (ECOG) data.
Figure 6:
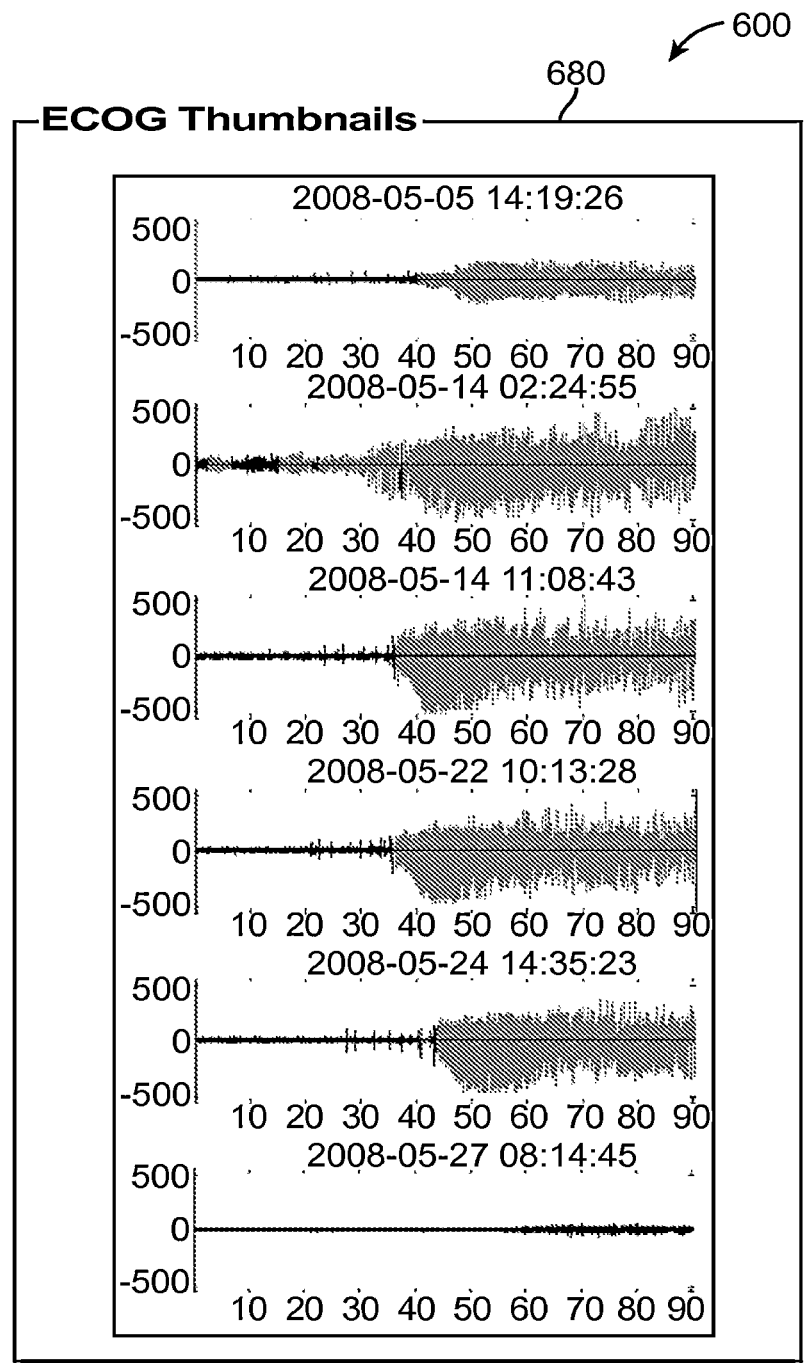

FIG. 6 illustrates an example of a screen 600 that might be displayed to a user (e.g., on the display of an external component such as a programmer or on a web page viewed via a website) when the user has selected one or more regions of interest 520, the method for automatically deriving a parameter set has been accomplished for the selected region(s) of interest, and the type of activity the detection tool would 'detect' with the automatically derived parameter set, based on the selected region(s) of interest, is displayed to the user.

In the specific example of FIG. 6, a portion 601 of a screen is labeled "ECOG Display" and depicts a single user-selected region of interest 603 extending from between about 40 s and about 43 s. (While it will be appreciated that an ECOG display such as the screen portion 601 may also display any regions of baseline activity selected by a user or by the system, no regions of baseline activity are depicted in the example shown in FIG. 6: An automatic-parameter-value-deriving-algorithm may not require any region of baseline activity in order to identify a set of parameters for a given detection tool).

As soon as the user selects region(s) of interest, a method for automatically deriving a parameter set for a detection tool automatically derives values for relevant parameters of a relevant detection tool and updates or overlays the ECOG Display with a simulation that reflects what the automatically derived parameter values used with the relevant detector would detect based on the features or patterns that are present in the user-selected region(s) of interest.

In the example of FIG. 6, after the user selects the region of interest 603, the ECOG Display 601, the simulation is shown to the right of the region of interest 603 on the graphs 610 (a time-series plot) and 620 (a spectrogram). Thus, the user is provided with visual feedback (by way of the simulation) almost immediately after the computer makes choices for the values of the parameters for the relevant detection tool. The visual feedback shows the user the nature and type of activity that would be detected if those parameter values were programmed into the neurostimulator. If the relevant detection tool happens to be a half wave detector configured to look for rhythmic activity, the user need not have an appreciation for what value the method has identified, for example, for the qualified analysis window count. Rather, the user can simply view the simulation, compare it to the graphical content of the region(s) of interest selected, and decide whether the automatically-derived values are close enough to the mark.

The top graph 610 of the two graphs 610, 620 in the display 600 is a time-series representation of an electrographic signal 602, similar to the time-series representation of the electrographic signal 500 in FIG. 5 from which the user selected the region(s) of interest. The shaded portion 608 of the top graph 610 demarcated by the double-headed arrow 606 between a time $t_{sim-l}$ and a time $t_{sim-f}$ represents the nature and type of electrographic activity that would be detected if the half wave detector were to be programmed with the parameter values the system automatically derived.

The bottom graph 620 of FIG. 6 is a spectrogram corresponding to the time-series representation. Here, the spectrogram is another way to visualize how much of the signal is characterized by certain frequencies as the signal varies with time. For example, in the electrographic signal 602 between of about 40 s and about 90 s (demarcated by the double-headed arrow 606), there is a concentration of power in the signal around or below 50 Hz, as represented by the lower, darker region 632 of the bottom graph 620 of FIG. 6 between the same times.

After a set of operating parameters for a detection tool has been automatically derived in accordance with embodiments, the user may be afforded the opportunity to adjust one or more values in the parameter set. Again, the user need not have an appreciation for the relevance of each discrete operating parameter to the function of the relevant detection tool in order to accomplish these adjustments. Rather, the parameters in the set of operating parameters for the detection tool will be ordered for the user in a manner significant to the graphical content of the region of interest, such that if the user adjusts the parameters, the adjustment will predictably result in more or less of the graphical content in the region of interest being detected in the subsequent simulation. Specific examples of options for a user to adjust detection tool parameter values are described below.

In the display represented in FIG. 6 there are two sliders 640, 650. The slider 640 is labeled "signal amplitude" and the slider 650 is labeled "pattern duration." Each slider 640, 650 is provided with a rectangular-shaped indicator 642, 652 and a pair of single-headed arrows 644/646, 654/656 (one arrow at each end of the slider) to indicate direction.

The left-facing arrow 644 of the signal amplitude slider 640 is associated with less sensitive detection of the desired signal by requiring the signal to meet a higher half wave amplitude threshold (e.g. increasing the minimum half wave amplitude parameter 192). From the user's point of view, however, moving the rectangular-shaped indicator 642 towards the left-facing arrow 644 will simply result in "detecting less" of the signal corresponding to the graphical content (e.g., the pattern) in the user-selected region of interest. When the simulation is refreshed with the adjusted minimum half wave amplitude parameter 192, the user will see in the simulation between the time $t_{sim-l}$ and the time $t_{sim-f}$ in the graphs 610, 620 of FIG. 6 that the system is rejecting (e.g. not detecting) the parts of the signal with smaller amplitude. The user can expect the behavior of the system to, in this case, detect less of a pattern in a region of interest without having an appreciation that the reason why the detector is detecting less is because the value of the minimum half wave amplitude parameter of the half wave detection tool configured to detect rhythmic activity was changed.

The right-facing arrow 646 of the same "signal amplitude" slider is associated with a more sensitive detection of the desired signal by lowering the value of the minimum half wave amplitude parameter 192. Moving the rectangular-shaped indicator 642 towards the right-facing arrow 646 results in "detecting more" of the signal in the simulation over the $t_{sim-l}$ to $t_{sim-f}$ period by detecting the parts of the signal with smaller amplitude. Again, the user need not understand that when he moves the indicator 642 in the "signal amplitude" slider to the right, the minimum half wave amplitude parameter is changing. Rather, the user will appreciate that when he moves around in the slider to the right, then the detector will reconfigure itself to detect more of the pattern the user saw in the region of interest the user selected.

In an embodiment, a user is able to slide the indicator 642 within the slider 640 (e.g., by clicking and dragging or by selecting the left- or right-facing arrows (644/646)) to adjust the sensitivity of the algorithm to be biased towards detecting higher or lower amplitude activity having characteristics like the signal in the simulation between $t_{sim-l}$ to $t_{sim-f}$. Accordingly, by moving an indicator around within a slider such as the slider 640, the user can test the effect of adjusting one of the operating parameters for a given detection tool without having to understand what that parameter is for (e.g., a "minimum half wave amplitude parameter") and without having to choose a specific value for that parameter (e.g., 50 amplitude units or 100 amplitude units, etc.) and without having to understand which value the system and method has selected for that parameter.

With regard to the pattern duration slider 650 shown in the display 600 of FIG. 6, the left-facing arrow 654 is associated with detecting "longer events" and the right-facing arrow 656 is associated with detecting "brief events". A user is able to slide the indicator 652 within the slider 650 to adjust the sensitivity of the algorithm to be biased towards starting to detect a pattern of activity like the pattern of activity in the simulation between the time $t_{sim-1}$ and the time $t_{sim-f}$ earlier or later (e.g. by adjusting the qualified analysis window count 196 and detection analysis window size 197 parameters).

The user's sliding of one of the signal amplitude indicator 642 or the pattern duration indicator 652 may cause the system to adjust the value of one or more of the parameters that were previously automatically-derived from the user's selected region(s) of interest and simulated in the simulation. Alternatively, or additionally, the user's sliding of one of the indicators 642, 652 may cause the system to introduce one or more additional parameters (and corresponding values therefore) to be used by the algorithm. In some embodiments, whenever a user moves one of the indicators 642, 652, the display will refresh with a new simulation to indicate to the user what effect the sensitivity adjustment will have on the nature and type of activity the adjusted algorithm will detect.

It should be appreciated that other "sensitivity" adjustments may be implemented using sliders such as sliders 640, 650. For example, if the detection tool is a line length detector, then a slider may refer to a percentage threshold, such that moving the indicator around in the slider results in changing a percentage threshold requirement, which may increase or decrease the sensitivity of detection. More particularly, a user may understand that when an indicator in a "percentage threshold" slider is moved in the direction of a left-facing arrow then the parameters of the detection tool will automatically be adjusted so that the detection tool will increase the threshold to detect only larger changes. Correspondingly, if the slider is moved in the direction of a right-facing arrow in a "percentage threshold" sensitivity adjustment, then the parameters of the detection tool will automatically be adjusted so that the detection tool will decrease the threshold to detect smaller changes in addition to larger changes.

Moreover, in some embodiments, one or more additional detection controls can be made available to the user, for example, when a user checks a box such as the box 658 on the display screen 600. These additional controls may allow the user to adjust the values of other parameters used by a given detection tool without the user having to have an algorithm-level appreciation for what each parameter is called or the effect it has on detection.

For example, the detection frequency may be controlled by another "lower/higher frequency" slider 660, which is shown in the example display 600 of FIG. 6 below the "signal amplitude" slider 640 and the "pattern duration" slider 650. A rectangular-shaped indicator 662 in the "lower/higher frequency" slider 660 may be initially set at a location in the slider corresponding to a peak frequency determined by an automatic-parameter-value-deriving algorithm to be within the user-selected region of interest 601. After a simulation has been run to display to the user the nature and type of activity that might be detected with the relevant detection tool with those automatically-derived parameter values, the user may determine that he or she wants to adjust the parameters corresponding to the frequency of what activity will be detected by the detection tool so that activity characterized by a lower or higher frequency will be detected. Rather than having to think about which detection tool parameter has to be adjusted and what value the parameter(s) ought to be changed to, the user may simply move the indicator 662 around in the "lower/higher frequency" slider 660, review the resultant simulations, and use this feedback to determine whether to make further adjustments using the "lower/higher frequency" slider 660, whether to move on to another sensitivity adjustment (i.e., a different one of the available sliders); or whether the detection tool is now configured to detect what the user wants the detection tool to detect when it next occurs in a signal sensed from the patient.

More particularly, by moving the indicator 662 in the "lower/higher frequency" slider 660 towards the right-facing arrow 666, values for parameters of an instance of a half wave detector would be adjusted so that the half wave detector would detect portions of signals that exhibit higher frequencies (and thus the algorithm would become more sensitive to higher frequencies). Correspondingly, if a user moves the indicator 662 in the "lower/higher frequency" slider 660 towards the left-facing arrow 664, values for parameters of the relevant instance of the half wave detector would be adjusted so that the half wave detector would detect portions of signal that exhibit lower frequencies (and thus the algorithm would become more sensitive to lower frequencies).

Similarly, a slider may be used to further refine the detection frequency to be more or less specific. For example, if a method for automatically deriving parameter values for a given instance of a half wave detector has determined that there is a peak frequency of 30 Hz represented in a particular user-selected region of interest, a "less specific/more specific" slider 670 may be used to adjust how specific to that peak frequency the user wants the results of detection by the half wave detector to be. For example, where a peak frequency is 30 Hz, a less specific frequency range may be 20 Hz to 40 Hz, whereas a more specific frequency range may be 25 Hz to 35 Hz. The user may move around in the "less specific/more specific" slider 670 by dragging the indicator 672 towards the left-facing arrow 674 or the right-facing arrow 676. Compared to an initial set of automatically-derived parameter value(s) corresponding to the frequency range identified in a user's selected region of interest, a less specific frequency range may result in a greater number of detections overall (for example, by the relevant half wave detector), and a more specific detection frequency range may yield fewer detections overall. In sum, with the "less specific/more specific" slider 670 shown near the bottom of the sample display 600 shown in FIG. 6, the user may ultimately settle on a set of parameter values for a given instance of a detection tool (e.g., an instance of a half wave detector) that will result in the detection tool being configured to detect different frequency ranges than the initial parameter set in order to detect the type of activity identified in the ROI with more or less specificity.

In certain instances of a half wave detection tool, the specific parameters the values of which are adjusted using a slider (or other feature configured for manipulation by a user) may comprise combinations of parameters, such as a combination of the half wave window size 195 and half wave count criterion 194. In other embodiments, adjustment of one slider may impact the available values of another slider. For example, adjustment of the "lower/higher frequency" slider 660 may change the parameter values in the "less specific/more specific" slider 670. The relevance to the method for automatically deriving parameter values and subsequent user-initiated sensitivity adjustments thereto for combinations of parameters for a detection tool is described in more detail below.

In view of the foregoing, it will be apparent that any of these sensitivity adjustments may be susceptible to use by a user in any number of ways, such as the sliders described above or via some other suitable visual prompt. Indeed, any suitable feature designed to make a system more "user-friendly" may be relied upon in embodiments to allow a user to fine tune the values for any one of the parameters (or the values for some combination of parameters) that are required for a given detection tool or algorithm to operate on physiological data, without the user having to appreciate which parameters of a detection tool are being adjusted or how the values of the same are being changed: the options are not limited to the examples of sliders described herein.

In some embodiments, the user will be able to test run the algorithm with the automatically-derived parameter values on any desired electrographic signals. For example, the user may select one or more files containing electrographic signals that were previously-recorded from the patient, from other of the user's patients, or from a class of patients with similar demographics to the patient.

For example, and referring to a panel 679 designated as "ECOG Thumbnails" on the right-hand side of the display 600 of FIG. 6, several previously-recorded electrocorticograms (or "ECOG"s) 680 may be displayed to a user (there are six previously-recorded ECOGs shown in the "ECOG Thumbnails" of FIG. 6), so that the user may observe the results of running a detection tool simultaneously on the several ECOGs to see what kinds of activity the detection tool would be likely to detect with a given set of parameter values automatically derived based on a region of interest (and based on a user's sensitivity adjustments, if applicable). Since the electrographic signals are never exactly the same, for example, just before a seizure develops, even for the same patient, the user can test a given parameter set on multiple previously-acquired ECOGs to test how consistently the algorithm will detect the nature and type of activity the user wants the algorithm to detect in a variety of situations.

In some embodiments, the ECOGs 680 shown in the "ECOG Thumbnails" panel 679 may be a set of ECOGs that the user previously flagged to be of interest. In other embodiments, the ECOGs shown in panel 680 may be a set of ECOGs that are generated by filtering and or sorting through a set of ECOGs, where the filtering and sorting is accomplished based on certain features. The filtering and sorting may be accomplished "manually" by a user as he or she searches and/or scrolls through possible ECOG candidates accessed on a database. Alternatively, the filtering and sorting may be accomplished automatically by various filtering and sorting algorithms. Some combination of user-initiated filtering and sorting and computer-initiated filtering and sorting is also contemplated.

One feature that might be used to sort ECOGs may be whether or not saturation was present in the ECOG. ("Saturation" in a previously-recorded ECOG may mean that the signal reflected in the recording had so much amplitude or otherwise so much power that it saturated the electronics through which it was processed and acquired for recording, such that the signal, for example, corresponds to a sensing amplifier pegged at a rail.) Another feature that might be used in sorting ECOGs may be the time at which the ECOG was recorded or some other circumstance associated with its recording (for example, whether it was recorded at night, whether it was recorded at the instance of the patient as opposed to because the active implantable medical device automatically recorded it as the result of running the signal sensed from the patient through a detection tool, etc.) In still other embodiments, the ECOGs 680 shown in the panel 679 may be automatically selected by the system for the user based on a selection algorithm that indicates that these ECOGs may be of interest to the user.

Figure 7:
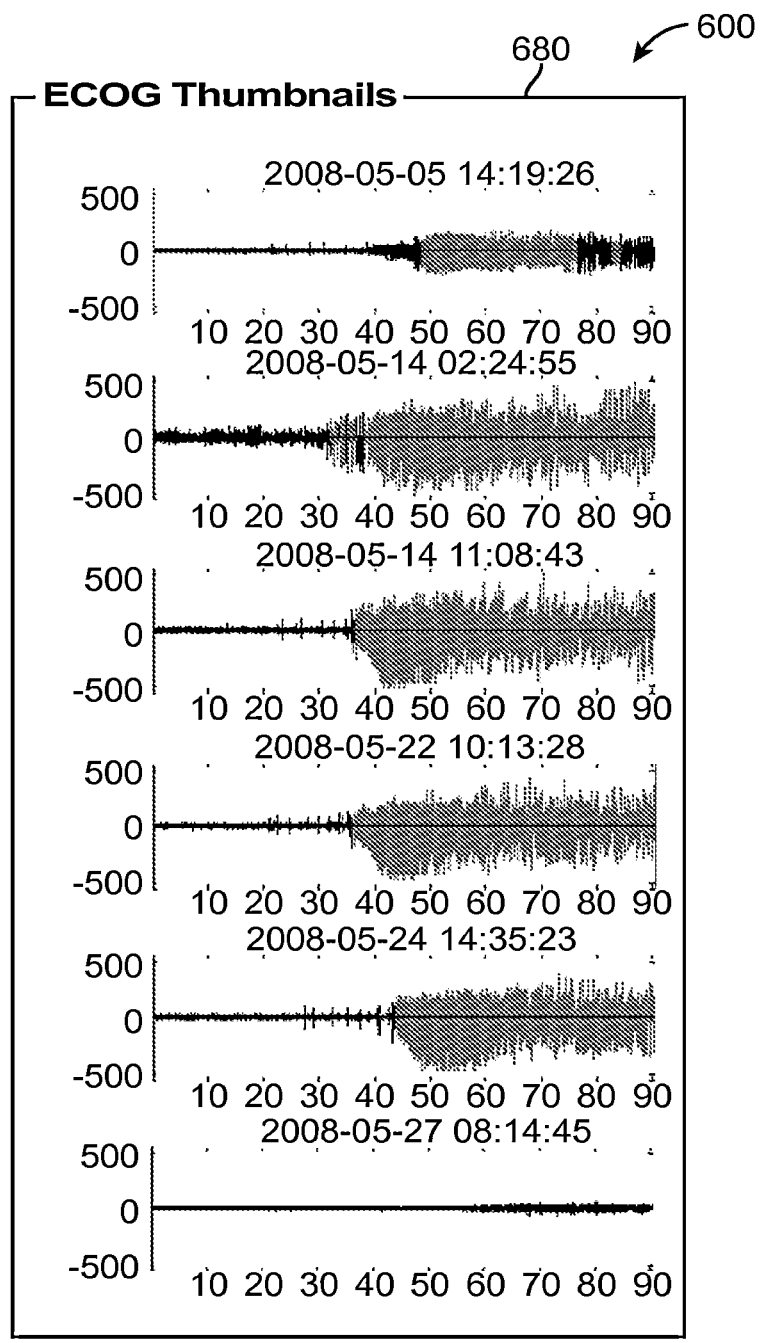
FIG. 7 is a representation of the display of FIG. 6 after a new simulation has been run and the display refreshed with the results of the new simulation.

FIG. 7 is another example of a display 600, representing an iteration of the automatically-derived parameter value set after a user has used the "signal amplitude" slider 640 by moving the indicator 642 further in the direction of the "detect less" (left-facing) arrow 644. When the user asks for the algorithm to be reconfigured to detect less by requiring the sensed signal to have a higher amplitude in order for the system to recognize a "detected event" to have occurred, then the algorithm will automatically adjust one or more parameter values (or add one or more parameters and associated parameter values) in an effort to comply with the user's request. The simulation (to the right of the selected region of interest 603 on the ECOG Display 601 of FIG. 7) is refreshed based on the user's use of the slider. More specifically, the result of the sensitivity adjustment can be appreciated in the time-series representation of the electrographic signal 602 in the top graph 710 of FIG. 7. The shaded portion 708 of the top graph 710 indicates that, after the user asks the algorithm to "detect less" insofar as the amplitude is concerned, the adjusted set of parameter values, if ultimately programmed into the patient's active implanted medical device for a given instance of a half wave detector, likely would detect a noticeable amount less of the signal than would the set of parameter values that resulted in the shaded portion 608 of the top graph 610 of FIG. 6.

Figure 23A:
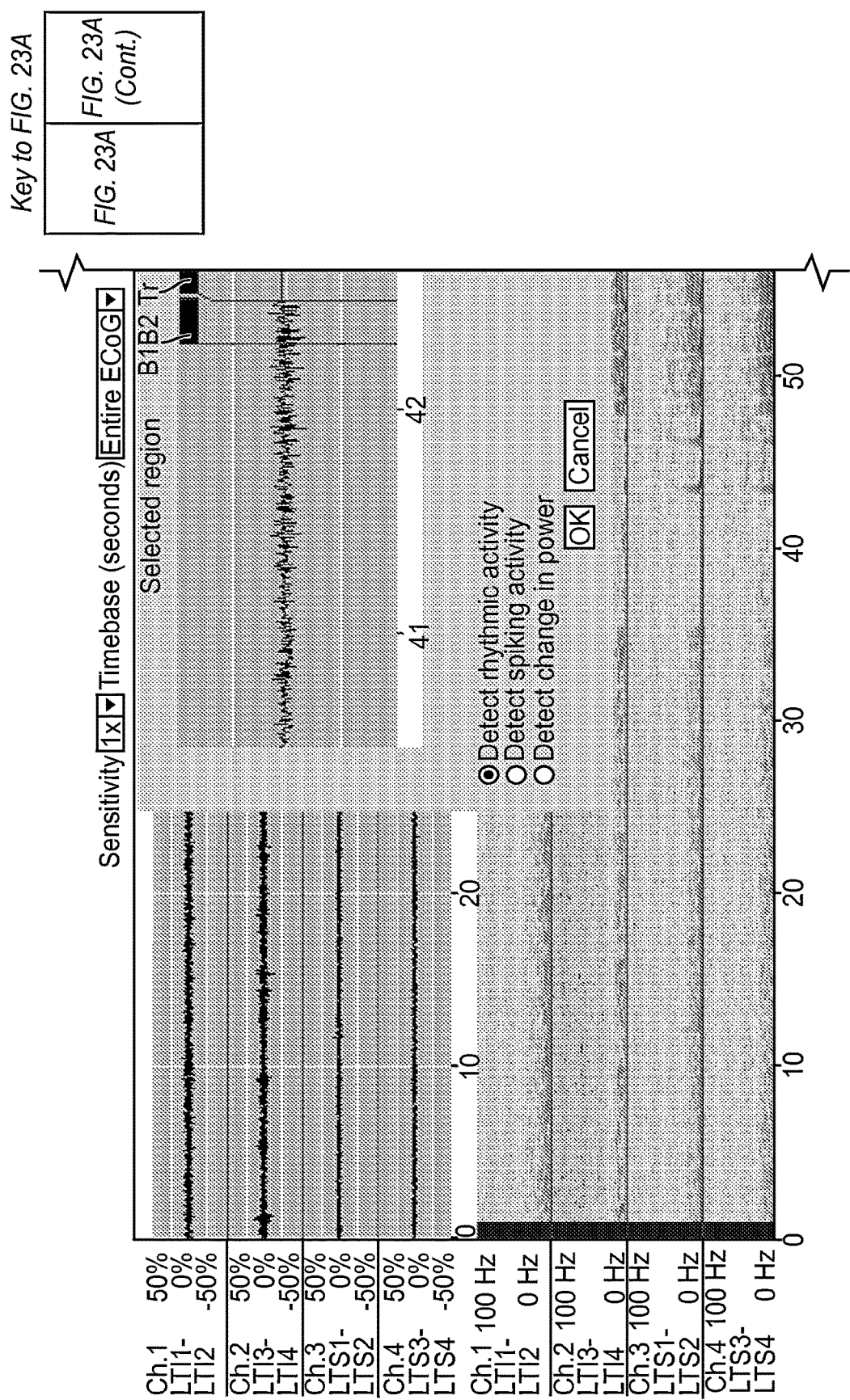
Figure 23A:
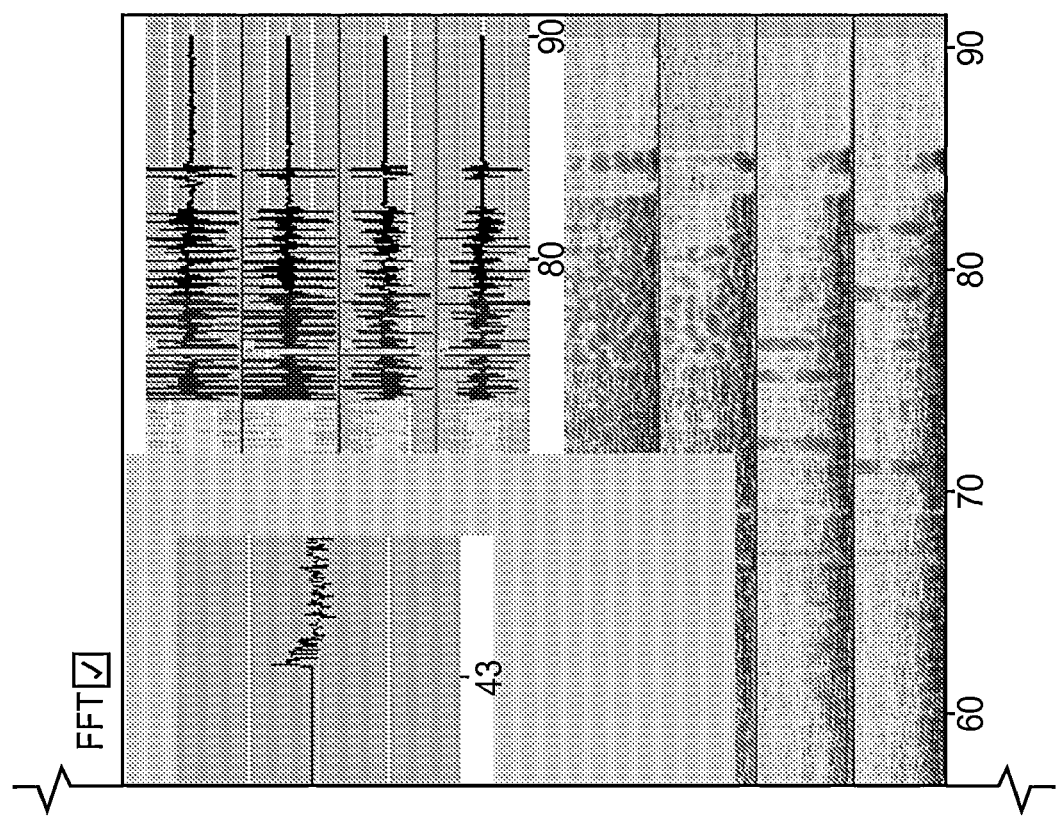

It will be appreciated that there are a great many possibilities for allowing a user to interface with a method for automatically determining and adjusting a parameter set for an activity type and/or a detection tool according to embodiments. Screen shots from a variety of graphical user interfaces are included in FIGS. 23A-23E. More particularly, FIG. 23A is an example of a user interface in which a user has selected a region of interest (ROI) on a previously-stored ECOG signal sample, and an embodiment has determined that the region of interest contains rhythmic activity (i.e., the "detect rhythmic activity" option is shown checked in the screen shot of FIG. 23A). This screen shot shows the system presenting the user an option to confirm or adjust the type of activity the user wishes to detect in the region of interest (e.g., the user may choose "detect spiking activity" or "detect change in power" options instead of the system-selected "detect rhythmic activity" option).

Figure 23B:
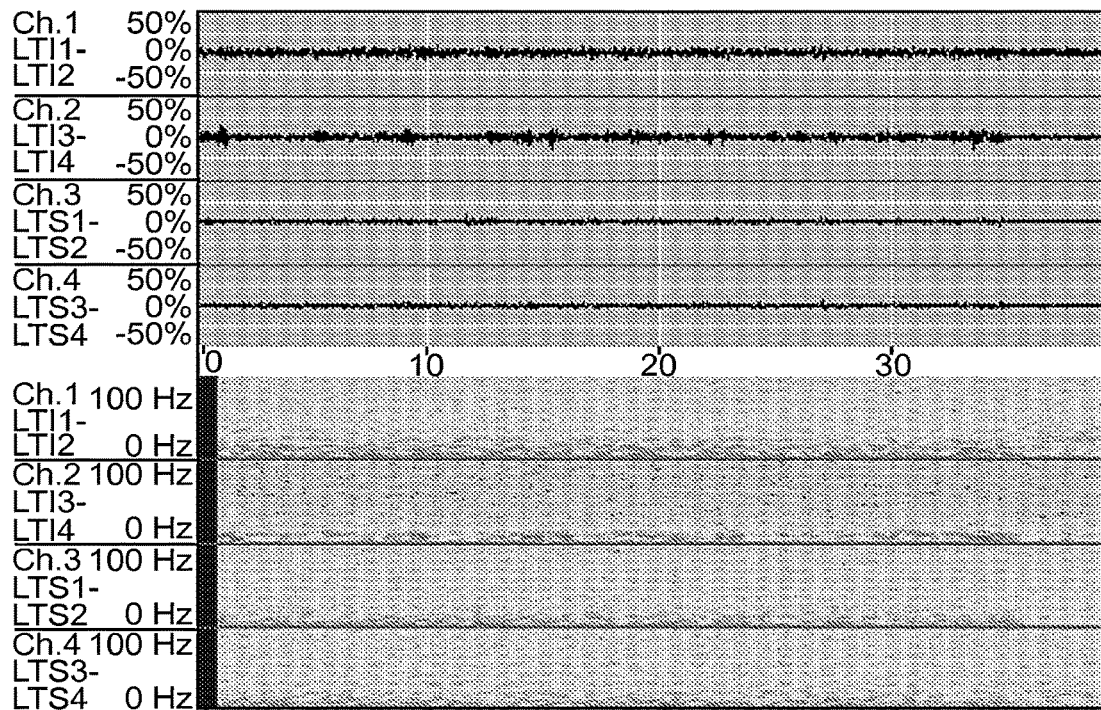
Figure 23B:
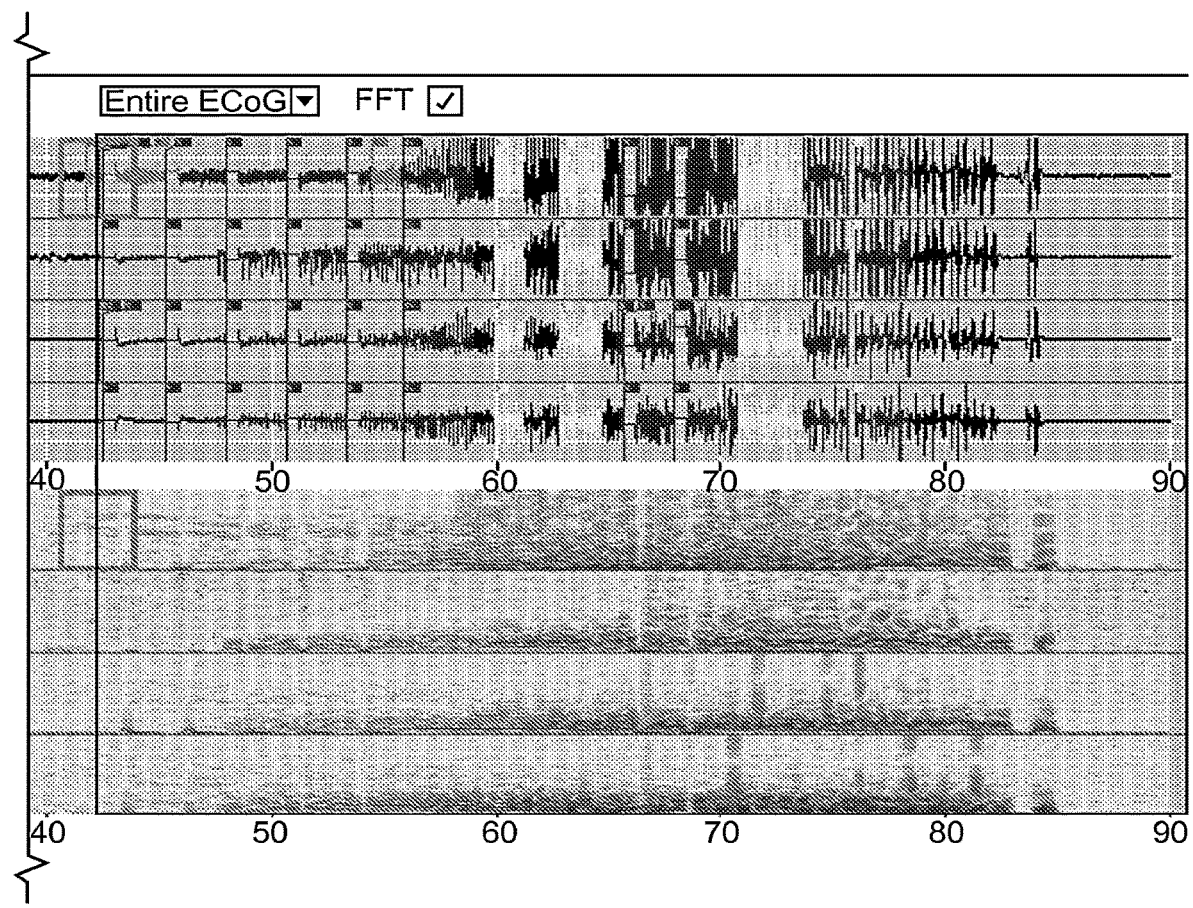

FIG. 23B is an example of a user interface in which a user has selected a region of interest (ROI) in a previously-stored ECOG signal sample and an embodiment has proposed an initial set of parameters for a half wave detection tool. These detection parameters have been loaded into the user interface and a simulation run to show the user what type of activity might be detected in a sensed signal with that parameter set. The user is presented with controls (upper left-hand corner of screen shot of FIG. 23B) with which the user can adjust or tune the detection parameters in the set to change the activity the detection parameter set will detect. For example, the detection parameters can be adjusted to detect "more events" or "fewer events" and/or to detect "longer events" or "brief events."

Figure 23C:
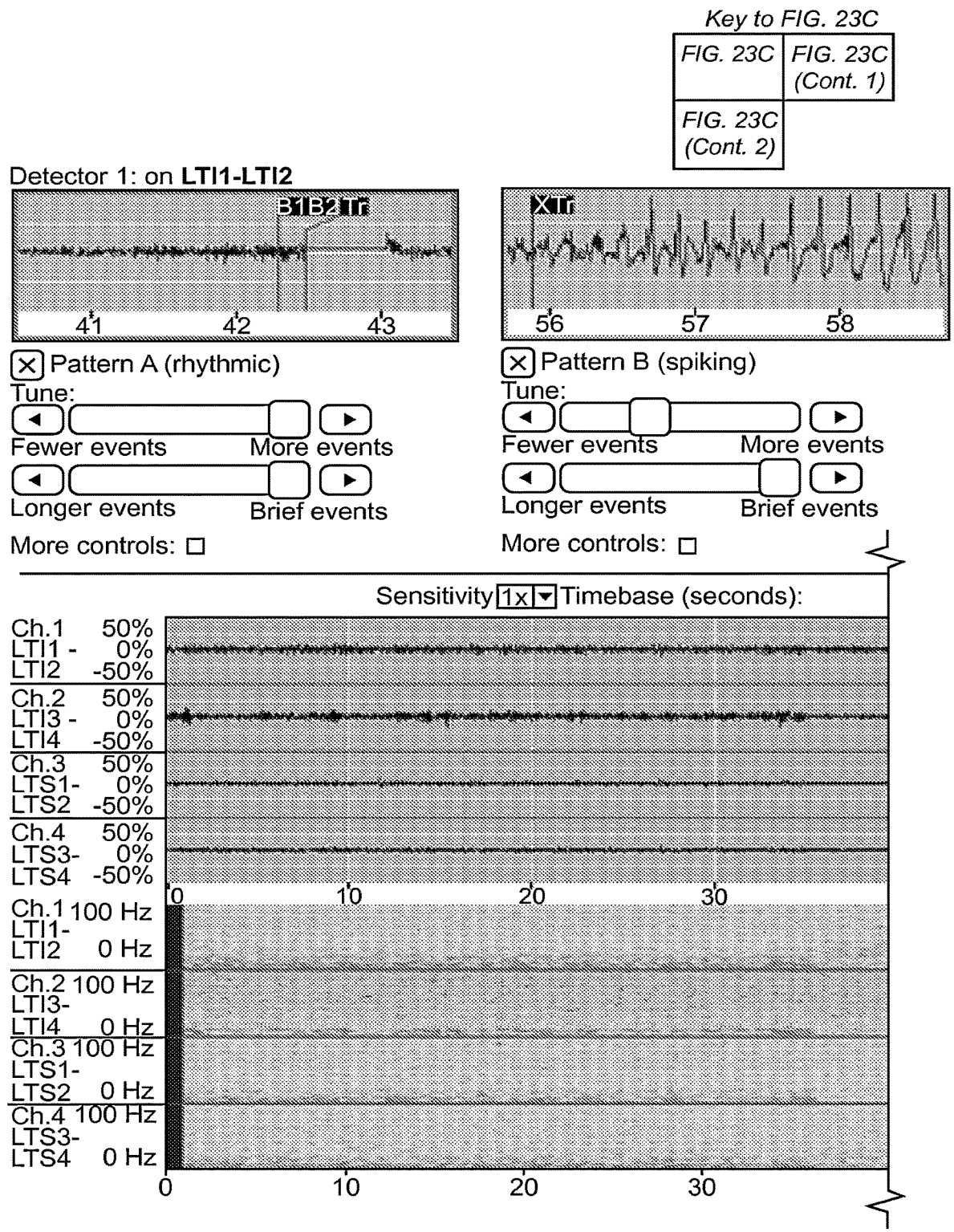

FIG. 23C is an example of a user interface in which a user has selected four distinct regions of interest on a sample of a stored ECOG signal (or on multiple samples). The user interface presents the user with controls for adjusting each of the four ROIs individually. The user interface also displays several thumbnail-sized ECOG signal samples. These allow the user to assess how a given set of detection parameters will perform on several different electrographic signals (i.e., what a detection tool configured with those parameters would detect if a sensed signal had characteristics like those in each of the samples). The user may be able to sort through the ECOG thumbnails for a particular patient by certain criteria. For example, a doctor may be able to look through the ECOG signals that have been stored for that patient (either on the user's programmer or in a central database) in the previous thirty days. In cases where the patient is able to cause the implant to store ECOG signals (for example, by waving a magnet near the implant), the doctor may be able to sort the ECOG signals according to whether the patient or the implant caused them to be stored. In still another example, the implant may have caused an ECOG signal to be stored (initially on the implant and subsequently downloaded to the programmer or uploaded to the central database), based on some triggering event. For instance, the ECOG signals may have been stored when a detection tool in the implant configured with a different set of operating parameters decided that an "event" should be deemed detected and the ECOG signal that triggered the detection stored in the implant's memory. Many other ways of sorting through stored ECOG signals, including those associated with multiple patients (e.g., of the user, or in a certain demographic, or with a certain seizure focus, etc.) are contemplated.

FIG. 23D is an example of a user interface in which a user is afforded the opportunity to manipulate the set of detection parameters for a detection tool associated with each of four regions of interest on a sample of a stored ECOG signal (or on multiple samples of signals) The detection parameters in each set have been loaded into the user interface and a simulation run to show the user what type of activity might be detected in a sensed signal with each parameter set. The user is presented with controls (upper left-hand corner of screen shot of FIG. 23B) with which the user can adjust or tune the detection parameters in each set to change the activity the detection parameter set will detect. For example, each set of detection parameters can be adjusted to detect "more events" or "fewer events" and/or to detect "longer events" or "brief events."

Figure 23E:
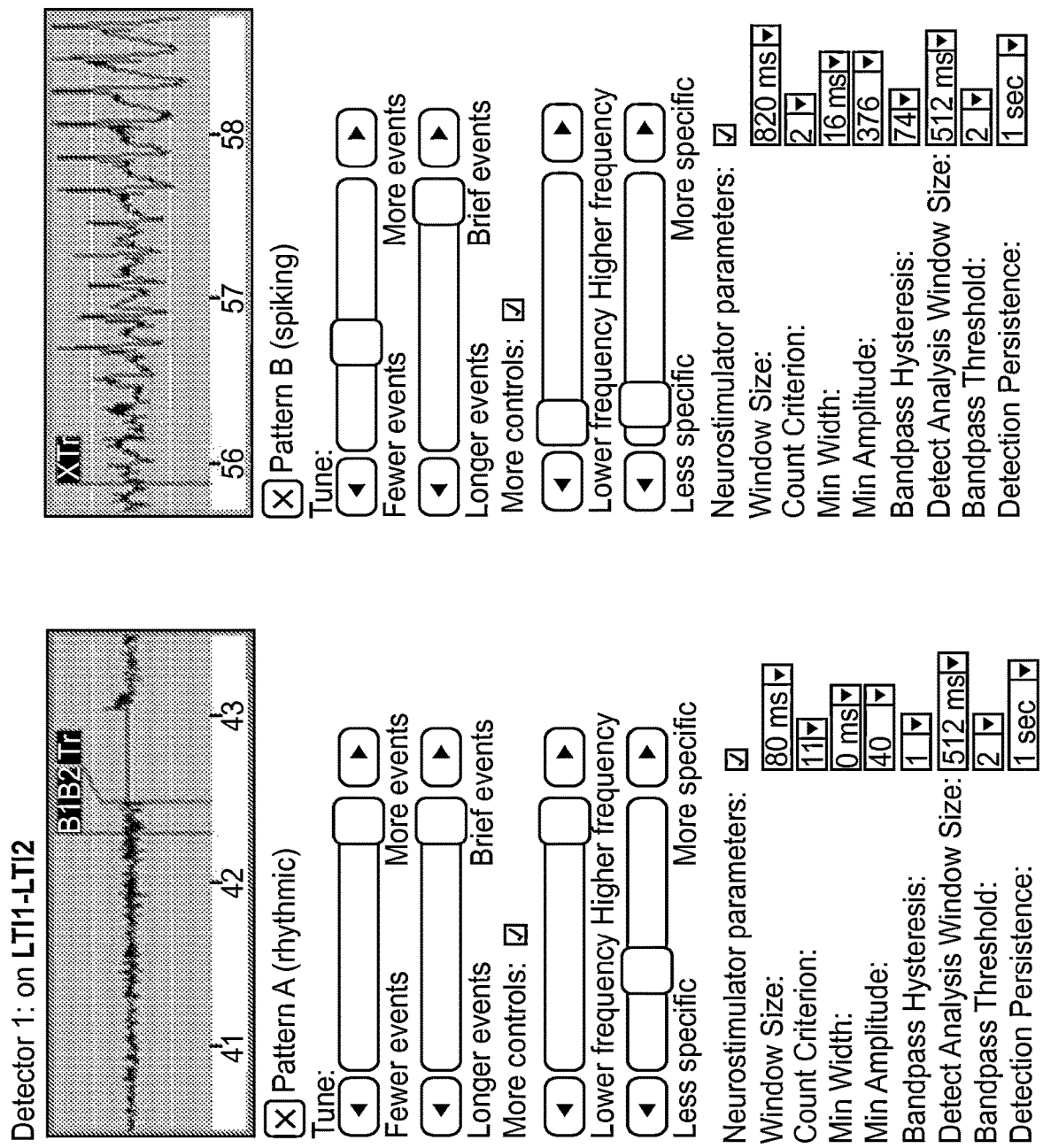
Figure 23E:
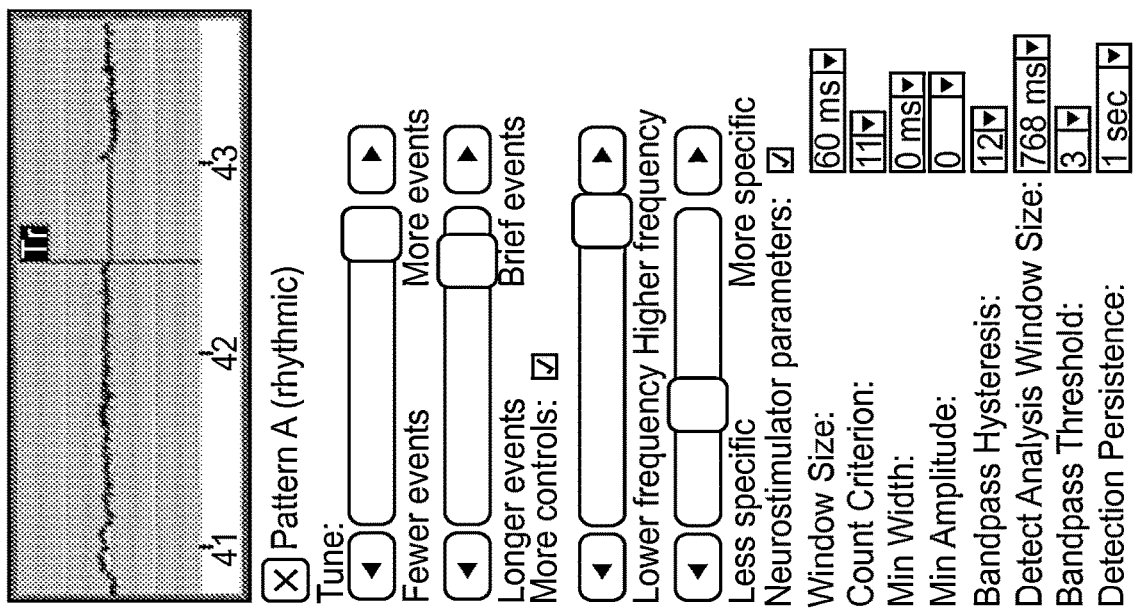

FIG. 23E is an example of a user interface in which a user has selected four distinct regions of interest on a sample of a stored ECOG signal (or on multiple samples). The user interface presents the user with controls for adjusting each of the four ROIs individually. For example, the user is offered controls for tuning the frequency and specificity of what a given set of detection parameters will detect. The user is also offered a view of what are the actual parameters and the parameter values that make up each of the four detection sets (e.g., "count criterion"=12, "bandpass hysteresis"=12, etc.).

Embodiments of a system and method for automatically deriving the parameter values for a half wave detector will now be described with reference to FIGS. 8A-8C as well as with reference to FIGS. 1A, 5, 6 and 7.

Generally, embodiments of the system and method are grounded on criteria for choosing parameter values that are reasonably related to the function the parameters perform in a given algorithm or detection tool, such as detecting portions of signals that are at or above a minimum frequency. For a given algorithm in which the number of parameters to be specified in order to detect something is greater than one, as in the case of a half wave detector like the half wave detector described above (in connection with which seven different parameters were described), it may be useful to describe the parameters as occupying a multidimensional parameter space, wherein relationships among the parameters are such that it makes sense to specify two or more of the parameter values together, as opposed to trying a value for each parameter one parameter at a time to see how close the result of what the algorithm detects with those values comes to what the user chose as something the user wants to detect. The manipulation of the parameters in the relevant parameter space is accomplished without requiring any input from the user beyond the user's selected a region of interest containing some graphical content the user would like a detection tool to be configured to detect.

In a simple example, a user may select a single region of interest or "ROI" in a previously-recorded sample of an electrographic signal sensed from a particular patient. For example, and referring again to FIG. 5, the user may select the portion of the electrographic signal extending from $t_{ROI-i}$ 522 to $t_{ROI-f}$ 528 as a region of interest 520. It will be appreciated that the context most often will dictate a region of interest for a user. For example, a region of interest likely will appear to the user's eye to correspond to a kind of activity the user wants to detect whenever it occurs in the patient. When the user wants to detect electrographic activity in a patient who has seizures for some purpose related to treating the seizures before they can fully develop, the user may select a region of interest 520 that precedes another region of activity that is believed to be associated with a seizure, such as the region 530 in FIG. 5, which is characterized by relatively high amplitude, high frequency activity. In other cases, in an epilepsy application, a user may want to select a region or regions of interest in which spike complexes occur. In still other cases the user may want to tune a half wave tool to detect activity that corresponds to a different condition of the patient, such as to a tremor associated with a movement disorder. And since the physiological response may vary between patients having the same or a similar condition, the region of interest a user may want to have a detection algorithm capture for one patient may be different from the region of interest the user wants to detect for another patient having the same condition. The graphical content of a particular region of interest may be appropriately referred to as a "pattern" in some applications, such as a spiking pattern or a pattern of rhythmic activity. In other applications, the graphical content of a particular region of interest may be characterized as a discrete feature rather than as a pattern.

In more complex situations, a system according to embodiments may offer a user the opportunity to combine more than one region of interest in a preliminary computation before asking a parameter-deriving algorithm to identify a set of parameters and parameter values. For example, in some cases, a user may wish to select two or more regions of interest that seem to exhibit very similar behavior but which are not identical. When these similar regions of interest are combined in a computation preliminary to selecting a set of values for the parameters for a given detector, the algorithm used for such a preliminary computation may be biased to provide a result that emphasizes commonalities in the selected regions of interest and minimizes differences. Such a preliminary computation thus may effectively increase the "signal-to-noise" ratio of the portion of physiological data the user ultimately wants the detector to detect (e.g., a pattern of activity in an electrographic signal that appears to precede an electrographic seizure in the patient).

In other cases, a user may want to use a preliminary computation to relate regions of interest to each other that are visually distinct but nonetheless deemed to be related to a state of the patient (for example, a patient's electrographic signals may exhibit different types of activity in different regions of the waveforms when the patient is about to have a seizure, where each different type of activity is deemed likely to presage a seizure state). Examples of these different types of activity for different types of seizure onsets in the same patient are described more fully with reference to FIG. 15A-15D, below.

Referring again to the case in which a user selects only one region of interest 520, the user or a computer may select a region of baseline activity, such as the region of baseline activity 540 shown extending between time $t_{B-1}$ 542 and $t_{B-f}$ 544 in FIG. 5. One way to think about the regions of baseline activity is that each region of baseline activity represents a type of activity that the user likely does not want the detection tool to identify as something to detect when that type of activity occurs. If a region of interest selected by a user is characterized by both some sort of baseline activity and a pattern that the user wants to detect, then selecting a region of baseline activity region will ultimately result in parameter values being selected that will not cause the detector to detect when only the baseline activity is present (i.e., without the pattern).

If the user does not select one or more regions of baseline activity, the computer may select one or more regions of baseline activity automatically, based on the user's selected regions of interest. For example, the computer may be configured to select a region of activity that precedes the beginning of a user-selected region of interest by a few seconds, based on an assumption that if the user did not include that activity within his or her selection of a region of interest, then this region of activity is something that the user does not want to detect, and therefore should be treated as baseline activity. This assumption may be an appropriate one in some applications and not in others, and the computer may be programmed to determine whether and when to apply the assumption accordingly.

In another example, if the region of interest corresponds to what the user believes is activity that represents the onset of epileptiform activity (e.g., a "seizure onset" or "onset type"), then it may be reasonable to assume that the region of interest corresponds to a transition in an electrographic signal from a region that the user does not want to detect to a region (e.g., a pattern) where the user would like detection. In this situation, then, the computer may select the activity occurring just before the user-selected region of interest as a region of baseline activity In some embodiments, even when the user or the computer selects a region of baseline activity, the baseline activity ultimately may not be used by the system in determining a set of parameter values for the relevant detection tool. Similarly, in some embodiments, a user may not be presented with the option of selecting any region of baseline activity.

In other embodiments, the process the computer undertakes to identity regions of baseline activity may be more varied and complex.

In still other embodiments, a user may select only one region of interest but the user or the computer (or the user and computer combined) may select multiple regions of baseline activity. If multiple regions of baseline activity are selected, then the system can undertake some preliminary computation relative to the several baseline activity regions in an effort to increase their relevance to the process of automatically deriving parameter values based on the region of interest. For example, a preliminary computation may combine information in the signal in the selected baseline activity regions. Such a combination may provide more comprehensive information about the types of activity that should not be detected whenever those types of activity occur in the sensed physiological data, as contrasted to what type(s) of activity should be detected (e.g., a pattern appearing in the activity in a region of interest chosen by a user).

Figure 8A:
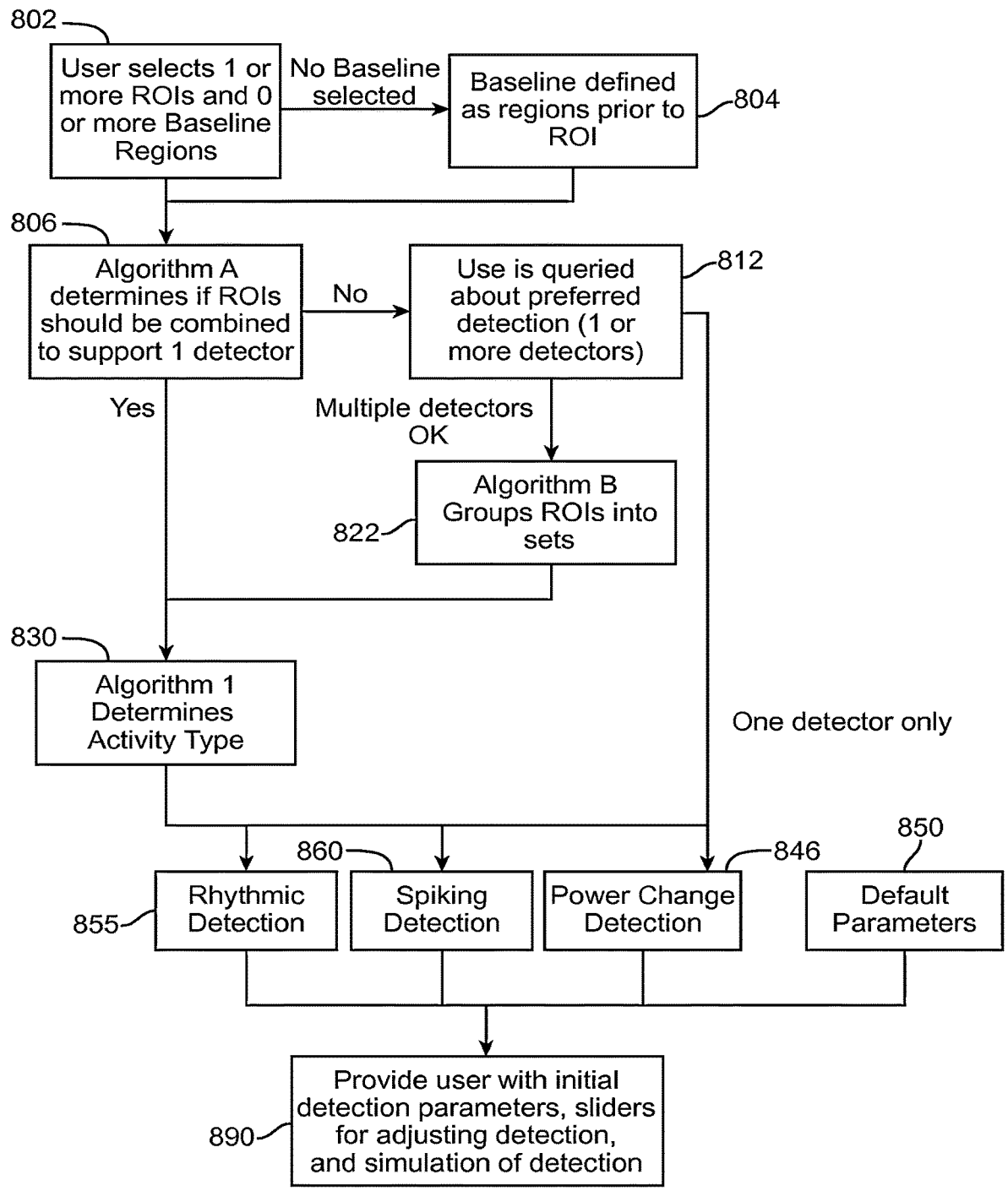
FIG. 8A is a flow diagram of a method of automatically deriving and, optionally, subsequently adjusting, parameter sets for detection tools for different activity types in a user-selected region or regions of interest, according to embodiments.
Figure 8B:
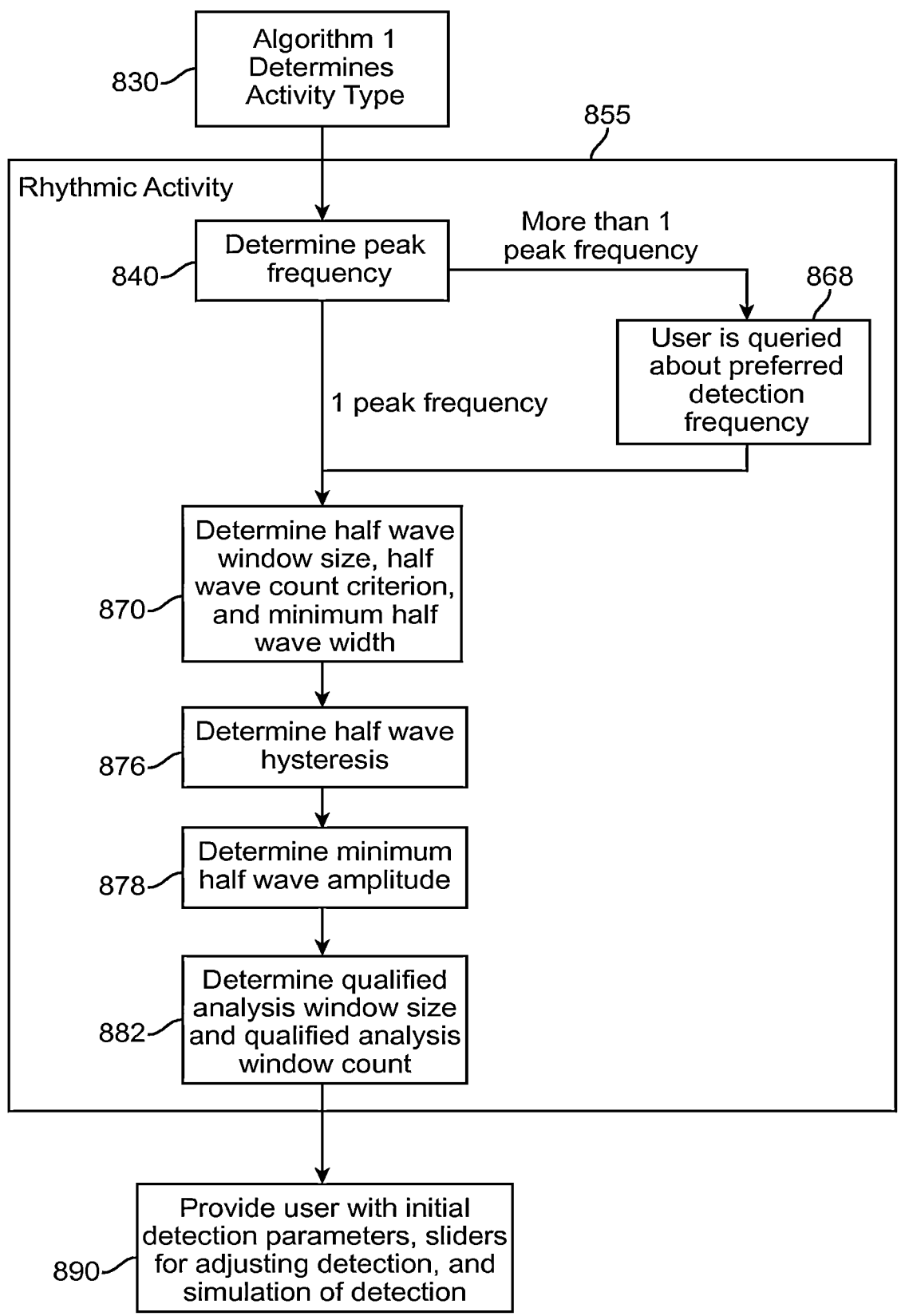
FIG. 8B is a flow diagram of a method of automatically deriving and, optionally, subsequently adjusting, a parameter set for looking for rhythmic activity in an electrocorticographic signal using a detection tool in the form of a half wave detector.
Figure 8C:
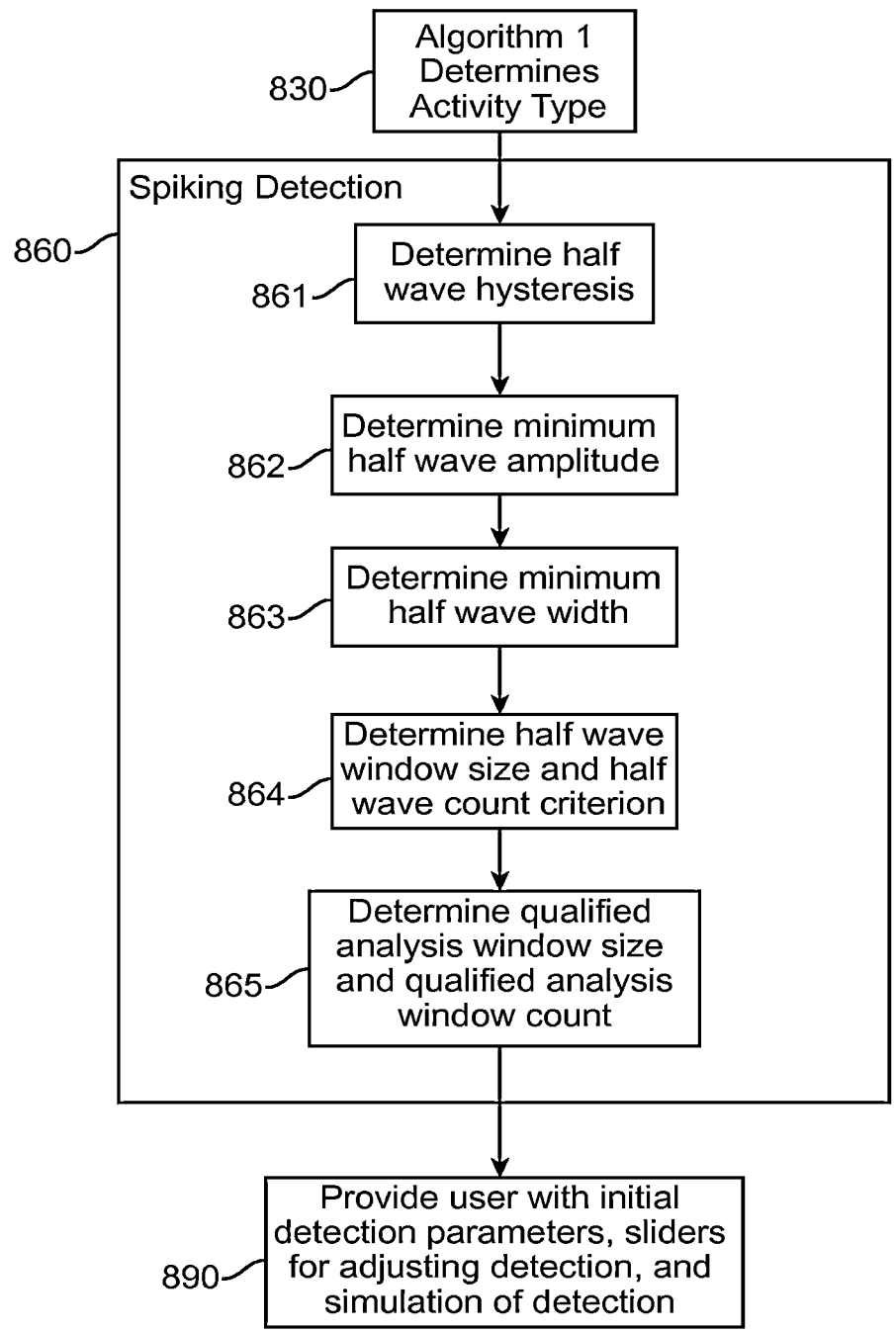
FIG. 8C is a flow diagram of a method of automatically deriving and, optionally, subsequently adjusting, a parameter set for looking for spiking activity in an electrocorticographic signal using a detection tool in the form of a half wave detector.

Referring now to FIGS. 8A-8C, methods for automatically determining the parameters and values for the same to be used by an instance of a detection tool (e.g., a detection tool to be implemented in an active implantable medical device) are described. FIG. 8A corresponds to the overall flow of a method the result of which is to determine an initial set of automatically derived parameter values for a detection tool and to then offer the user an opportunity to adjust the sensitivity of the initial set without having to understand exactly which parameters of the detection tool are being adjusted or how. The sensitivity adjustments may be offered to the user via user-friendly features (e.g., sliders implemented on a graphical user interface).

More particularly, in FIG. 8A, a detection tool will be selected based on the system's assessment of a type of activity the user seems to be interested in detecting based on the composition of the user-selected region or regions of interest. For example, if the type of activity in the user-selected region or regions of interest corresponds to rhythmic activity or spiking activity, a half wave detector may be selected as a detection tool. If the type of activity in the user-selected region or regions of interest corresponds to a change in amplitude and or frequency, a line length detector may be selected as a detection tool.

FIG. 8B is a flow diagram of a method when the system has determined that the activity is rhythmic activity and that the detection tool for looking for the rhythmic activity will be a half wave detector. FIG. 8C is a flow diagram of a method when the system has determined that the activity represented by a region or regions of interest is spiking and that the detection tool for looking for the spiking will be a half wave detector. In each case, the system-selected half wave detector may be configured to monitor electrographic signals (e.g., sensed on one or more channels of an active implantable medical device).

In FIG. 8A, the flow diagram indicates that, at block 802, a user selects a region of interest 520 or regions of interest 520 and, optionally, one or more regions of baseline activity 540. In an embodiment corresponding to FIG. 8A, if the user fails to select one or more regions of baseline activity at block 802, then at block 804, the computer selects one or more regions of baseline activity 540. The computer may or may not ultimately use the baseline region(s) in a system and method for automatically determine a parameter set for a given detection tool. It should be appreciated that, in some embodiments, selection of a region of baseline activity by a user and selection of a region (or regions) of baseline activity automatically by the computer need not be mutually exclusive. A user may select a baseline and the computer may select another region of baseline activity, with or without incorporating the user-selected region of baseline activity into a preliminary computation to establish a baseline for the system and method that automatically derives a parameter set for the detector.

At block 806, and if more than one region of interest 520 has been selected at block 802, the system undertakes a first preliminary computation (denoted as "Algorithm A" in FIG. 8A), to determine whether any or all of the selected regions of interest 520 should be further processed or operated upon before a region of interest 520 is used as the basis for deriving a parameter set for a particular instance of a detection tool.

For example, if a user selects three regions of interest 520, the first preliminary computation may be to determine whether the three regions of interest have some common feature or features that suggest to the system that the user is interested in detecting a particular type of activity (e.g., rhythmic activity). In some embodiments, Algorithm A may determine that signals in the regions of interest are similar, such that combining the data may be advantageous (e.g., Algorithm A may determine that the content of the three user-selected regions of interest should be combined to support a single instance of a detection tool). A combination of regions of interest may be advantageous, for example, to effectively increase the "signal-to-noise" ratio of the portion of physiological data the user ultimately wants the detector to detect (e.g., a pattern of activity in an electrographic signal that appears to precede an electrographic seizure in the patient). Ultimately, signals detected with a detection tool associated with a higher "signal-to-noise" ratio are likely to provide better information about the condition of the patient.

In other cases, however, when a user selects multiple regions of interests, the signals in those regions may be so different (for example different physiological signals may be associated with different types of seizures) that each would be better detected using detectors biased for detecting different types of activity (e.g., a detector biased to detect rhythmic activity versus a detector biased to detect activity representing a significant power change in the signal). When such differences are apparent to the system, in order to detect different types of physiological activity, the system may ask the user to allow it to separate the regions of interest or portions of the signal and to use different detection tools (or different instances of the same kind of detection tool with varying parameters or parameter values) to look for the activity when it occurs in the patient. Alternatively in these circumstances, the system may opt to use a default tool or default parameters or default parameter values as is described further below.

If the first preliminary computation (Algorithm A) result is that the user-selected region(s) of interest 520 should not be further processed or operated upon before being used as the basis for deriving a set of operating parameters for a detection tool, then in the process shown in FIG. 8A, at block 812, the system may query the user before proceeding further. For example, a user may select multiple regions of interest and, at block 806, Algorithm A may not be able to find significant features in common (or enough features in common) among the different regions in order to conclude that they be used in combination to choose a detection tool and then parameter values for that tool. In this case, the system may prompt the user to allow the system to segregate the user-selected regions of interest in ways that make sense to it given the various options for detection tools the system is configured to provide. For example, the system may ask the user if it can break the regions of interest up into one set that makes sense for the rhythmic activity type, and another set that makes sense for the type of activity that represents a power change in the sensed signal. If the user does not assent to the system's proposed grouping of the user-selected regions of interest into such groups, then the system may select a more generic type of detector (e.g. in FIG. 8A, block 846, the power change detector may be defined as the more generic type of detector). When a power change detection tool has been selected, then the method for automatically deriving a parameter set either may automatically derive values for the parameters relevant to the power change detection tool (at block 846) or may populate some or all of the parameters with predetermined default values (at block 850). In other embodiments, different options may be available for any or all of a default activity type, a default detection tool, and default parameter sets for a default activity type or detection tool.

If the first preliminary computation (Algorithm A) result is that the user-selected region(s) of interest 520 should be further processed or operated upon before being used as the basis for deriving parameter values, then after the result of that preliminary computation is obtained, at block 830, an activity type algorithm ("Algorithm 1" in FIG. 8A) is used to select a type of activity represented in the region(s) of interest. In FIG. 8A, three types of activity are contemplated as possible results from an activity type algorithm, namely, rhythmic activity, spiking, and activity that represents a change in the power of the signal in the region(s) of interest. It should be apparent that an activity type algorithm may be configured to identify other patterns and therefore other types of activity when they occur in a region of interest selected by a user.

Activity Type Analysis/Rhythmic-Spiking Power Change

A system and method that will automatically derive a parameter set for a detection tool based on a user-selected region of interest (e.g., a region of interest in an EEG signal marked by a physician) may be configured to first determine a type of activity present in the region of interest. For example, an automatic parameter derivation method may use an activity type algorithm ("Algorithm 1" in FIG. 8A) to determine with high certainty whether the main pattern present in the signal corresponds to a rhythmic activity (as opposed to, for example, spike activity). Such an activity type algorithm will be useful if a region of interest exhibits a distinct dominant pattern or other feature. When a combination of patterns is present in the region of interest, the system may prompt the user to make the decision on the type of pattern to configure the detector(s) to detect.

There are some typical EEG morphologies present at the onset of or within the body of EEG signals that are understood to correspond to seizures. These can be broadly categorized as: (1) rhythmic patterns that can be slow or fast in frequency; and (2) spike trains that lead to a seizure or that can be present within a seizure. Desirably, an active implantable medical device that is configurable to detect patterns associated with seizure activity would have detection algorithms suitable for these two patterns (rhythmic or spike activity) as well as the capability to detect other types of activity that may be associated with a seizure such as a sudden change in amplitude and/or a change in frequency. A generic detection system based on these two traits may be able to capture if not all, most of the previously unseen seizures and could help complement the pattern specific detectors available for rhythmic and spike activity.

Working with a previously-selected ECOG (e.g., selected from the ECOGs 680 displayed in the ECOG Thumbnails 679 of FIG. 6), the user selects a region of interest based on a start and end time. For example, the user may click on the selected ECOG at a time $t_{ROI-i}$ 522 corresponding to the beginning of a region of interest 520 and then drag until the user reaches a desired end for the region of interest at a time $t_{ROI-f}$ 528. A typical user-selected region of interest might span about 3 to 5 seconds on the selected ECOG. Once the user has selected a region of interest, the system analyzes the region of interest to determine whether a dominant activity type or pattern is present in the region of interest. Systems and methods according to embodiments may make this determination base on one or more pre-determined approaches to such a classification problem. These approaches may include, but are not limited to, neural networks, SVMs (Support Vector Machines), clustering techniques, rule-based approaches, and genetic programming. A system may decide which approach to use based on historical data concerning distinctions between classes of activity occurring in ECOG signals.

Figure 20A:
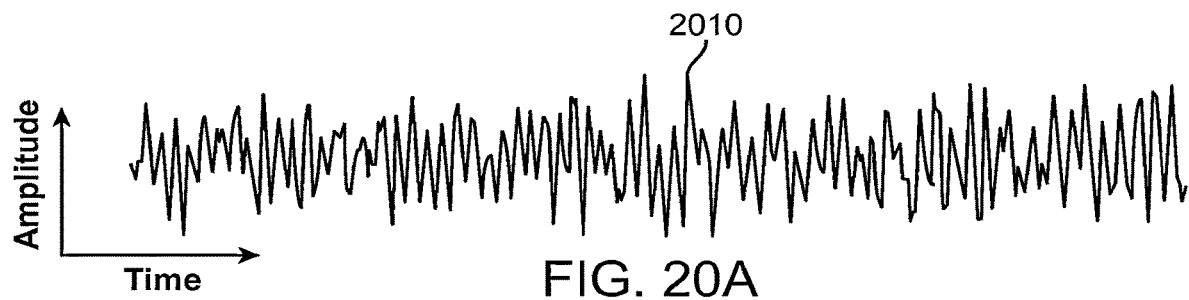
FIG. 20A, FIG. 20B, and FIG. 20C each is a graphical representation of a rhythmic type of activity as may occur in electrographic signals sensed from a patient.
Figure 20B:
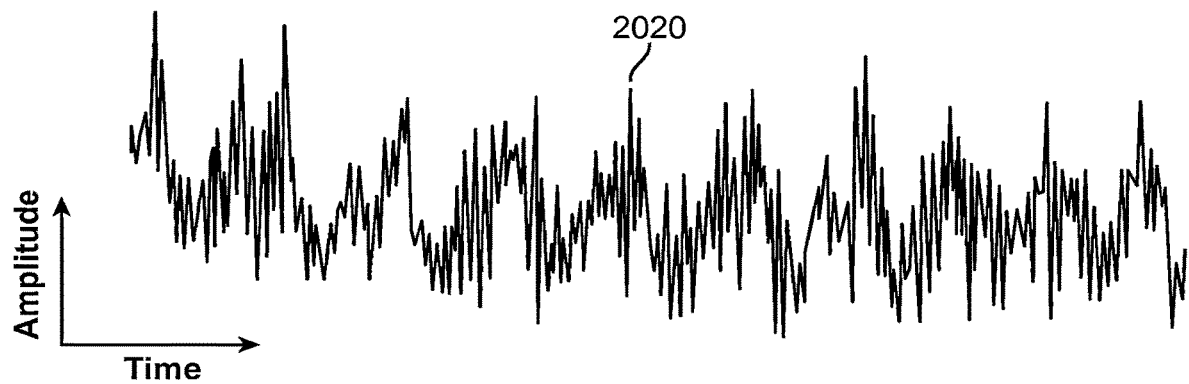
Figure 20C:
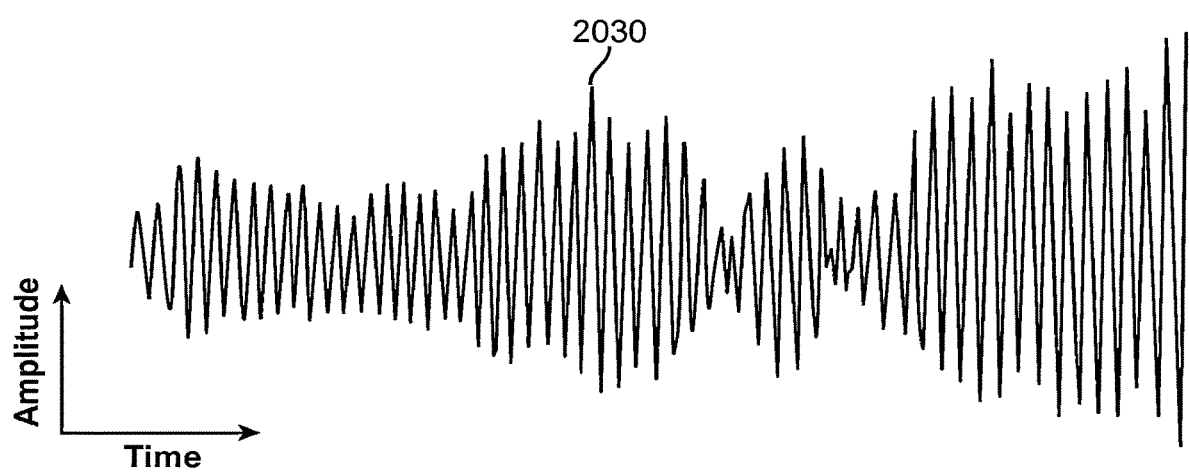
Figure 21A:
FIG. 21A, FIG. 21B, and FIG. 21C each is a graphical representation of a spiking type of activity as may occur in electrographic signals sensed from a patient.
Figure 21B:
Figure 21C:
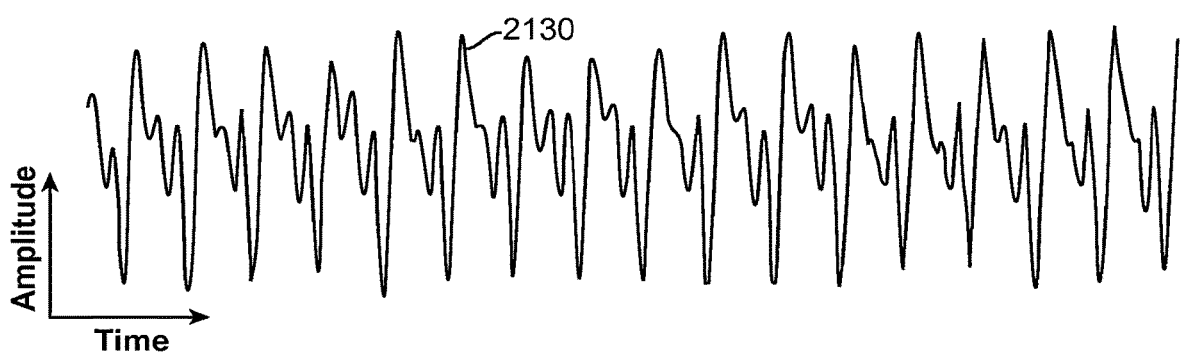

In an example, 92 regions of interest were used to guide the selection of features to differentiate across the two main pattern classes: rhythmic and spike activity. It is important to appreciate that a given region of interest may exhibit a combination of these patterns, or may exhibit very periodic spikes that can be considered rhythmic (due to their almost constant periodicity). Each graph in FIGS. 20A-20C is an example of a signal that exhibits rhythmic activity. Each graph in FIGS. 21A-21C is an example of a signal that exhibits spiking. And each graph in FIGS. 22A-22C is an example of a signal that exhibits a combination of rhythmic activity and spiking.

Once the activity type algorithm has determined an activity type, then a method for automatically deriving a parameter set for that activity type will attempt first to select a detection tool from among the available options for detection tools that correspond to the activity type. If the method for automatically deriving parameter sets cannot find a good option, then the algorithm may select a default detection tool and, at block 850, a default set of values for the relevant operating parameters for the default detection tool. However, if the method for automatically deriving parameter sets can find a good option from among the available options for detection tools that correspond to the activity type found by Algorithm 1, then values will be chosen for the parameters the selected detection tool needs to run or operate.

In FIG. 8A, if the activity type algorithm identified rhythmic activity, then a method for automatically determining parameter sets will first choose a detection tool that is well-suited for detecting rhythmic activity, and then choose parameter values for an instance of such a detection tool that biases the tool to look for the same kind of rhythmic activity as in the user-selected region(s) of interest. If at block 830, Algorithm 1 identified a spike or spikes as the activity type, then a system and method for automatically determining a parameter set for a detection tool will first choose a detection tool that is well-suited for detecting spikes and then choose values for the operating parameters of an instance of that tool that will bias it to look for the same spikes as occur in the user-selected region(s) of interest. If the activity type algorithm identified activity representing a power change in the signal at block 830, then a system and method for automatically determining a parameter set for a detection tool will first choose a detection tool that is designed to detect power changes and then choose operating parameters and parameter values for an instance of that power change detector that will tune it to look for the same sort of power changes whenever they occur in the future signals sensed by the implant if the implant is programmed with that parameter set.

If the activity type algorithm cannot identify a type of activity in the user-selected region(s) of interest, at block 850 the system may establish a detection tool by default. In this case, the system may select a default set of parameters for the tool to use together with default values for each parameter. In one embodiment, the default condition may be a line length detection tool configured with parameters that are configured to detect when a monitored signal exhibits a 50% increase in line length as compared to a recent trend for that signal's line length.

In connection with FIG. 8B and FIG. 8C below, described are systems and methods for automatically deriving a set of operating parameters for a half wave tool biased to look for rhythmic activity (FIG. 8B) and to look for spikes (FIG. 8C).

Also described below are systems and methods for automatically deriving a parameter set for detection tools that can be biased to look for power changes in a region or regions of interest (e.g., a line length detection tool).

The detection type algorithm (Algorithm 1 at block 830 in FIG. 8A) may evaluate the output of the first preliminary computation algorithm (Algorithm A) and determine that a region of interest or regions of interest 520 suggest that the pattern the user seems to be interested in is electrographic activity that constitutes rhythmic activity (as will be described more fully below). In this scenario, the detection type algorithm (Algorithm 1 at block 830 in FIG. 8A) may evaluate the output of the first preliminary computation algorithm (Algorithm A) and determine, first, that a region of interest or regions of interest 520 selected by a user suggest that the pattern the user seems to be interested in is electrographic activity occurring at a relatively high frequency (or in a range of frequencies that are relatively high). In this case, at block 830, the detection type algorithm will specify a half wave detector for rhythmic activity.

Next, at block 855, the system and method for automatically deriving a set of parameters ("Rhythmic Detection" in FIG. 8A) will identify an initial set of values for the parameters necessary for the half wave detector to run. The values selected will be such as to bias the half wave detector to detect rhythmic activity similar to that which is found in the user-selected region(s) of interest 520. FIG. 8B has additional detail on an embodiment for automatically deriving a set of operating parameters for a half wave detection tool configured to look for (or "detect") rhythmic activity.

Another pattern a half wave detector may be configured to detect may correspond to the occurrence of spiking activity in the signal. That is, the detection type algorithm (Algorithm 1 at block 830 in FIG. 8A) may evaluate the output of the first preliminary computation algorithm (Algorithm A) and determine that a region of interest or regions of interest 520 suggest that the pattern the user seems to be interested in is electrographic activity that constitutes one or more spikes (as will be described more fully below). In this case, at block 860, the detection type algorithm will result in specification of a half wave detector for spiking detection. Next, at block 860, the system and method for automatically deriving a parameter set ("Spiking Detection" in FIG. 8A) will identify an initial set of values for the parameters necessary for the half wave detector to run. The values selected will be such as to bias the half wave detector to detect activity similar to that which is found in the user-selected region(s) of interest 520. FIG. 8C has additional detail on an embodiment for a system and method for automatically deriving a parameter set for a half wave detection tool configured to look for or detect spiking.

In still other embodiments, the algorithm for determining whether any or all of the selected regions of interest 520 should be further processed or operated upon before a region of interest 520 is used as the basis for deriving a parameter set and values for the same (i.e., Algorithm A at block 806 in FIG. 8A) may be run after a detection type algorithm has been run. Alternatively, more than one algorithm for determining whether a selected region of interest should be combined with any other region (region of interest or baseline) or otherwise processed or operated upon may be run at different times in the process of automatically deriving parameter values for a detection tool.

Rhythmic Activity/Half Wave Detector

Referring now to FIG. 8B, embodiments will be described of a system and method for automatically deriving a parameter set for a half wave detector where the physiological data at issue comprises electrocorticographic signals and the type of activity in the region(s) of interest has been determined to be rhythmic activity (for example, by an activity type algorithm such as Algorithm A in FIG. 8A).

First, and referring again to FIG. 5, a user selects a region or regions of interest 520 from the time-series recording of an electrographic signal 500 and either the user or the computer selects one or more regions of baseline activity 540. The system and method generates or otherwise obtains a frequency spectrum corresponding to the data encompassed by the user-defined region of interest 520 (region-of-interest frequency spectrum) and a frequency spectrum corresponding to the data encompassed by the region(s) of baseline activity 540 (baseline frequency spectrum).

At block 830 in FIG. 8B, and after any preliminary calculations have been undertaken to determine whether to, for example, combine user-selected regions of interest, the content of the region(s) of interest is evaluated to determine whether the signal in the region of interest can be characterized primarily by one of rhythmic activity, spiking activity, an increase in signal power, or some other feature that may be of interest to the user. (In FIG. 8B, it is assumed that Algorithm 1 determines that the activity type is rhythmic activity.)

In one embodiment, determining that the activity type is rhythmic activity may be accomplished by evaluating the power spectrum of the signal and determining if there is at least one frequency which has significantly greater power than other frequencies. If the region(s) of interest is deemed to represent rhythmic activity, and the system's available options for detecting rhythmic activity include a half wave detector, then the system may determine parameters for an instance of a half wave detector. Various aspects of an embodiment of an algorithm for determining a parameter set for a half wave tool for rhythmic activity are described with reference to the items within the block 855 of FIG. 8B.

At block 840, a peak frequency is determined. In an embodiment, in a simple example where there is one region of interest and one region of baseline activity, the two frequency spectra (that is, the region-of-interest frequency spectrum and the baseline frequency spectrum) are compared to identify a frequency of interest. In some applications, this frequency of interest is a frequency that is present with higher power within in the region of interest as compared to at baseline.

It will be apparent that more than one approach may be used to obtain a frequency spectrum for a given region. In some embodiments, a frequency spectrum may be obtained by using a fast Fourier transform or "FFT". In other embodiments, the frequency spectrum may be obtained using linear predictive coding or "LPC." Linear predictive coding may provide an advantage over more traditional methods of estimating the power spectral density in a signal insofar as LPC may smooth the frequency peaks such that the number of frequency peaks in a sample may be more easily perceived or specified.

Figure 9B:
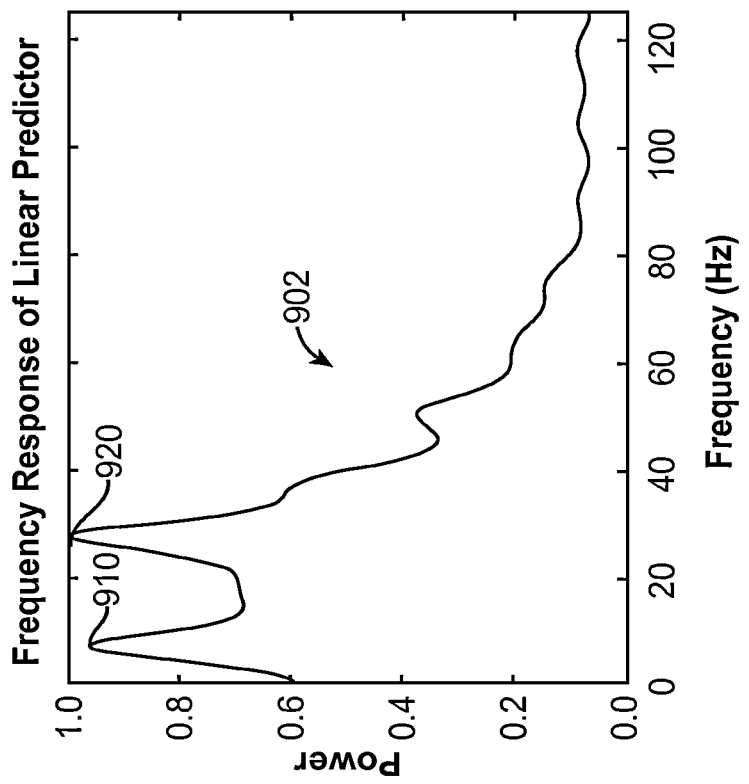
FIG. 9B is a spectrogram corresponding to the frequency content in a region of interest in an electrographic signal according to embodiments using linear predictive coding.
Figure 9A:
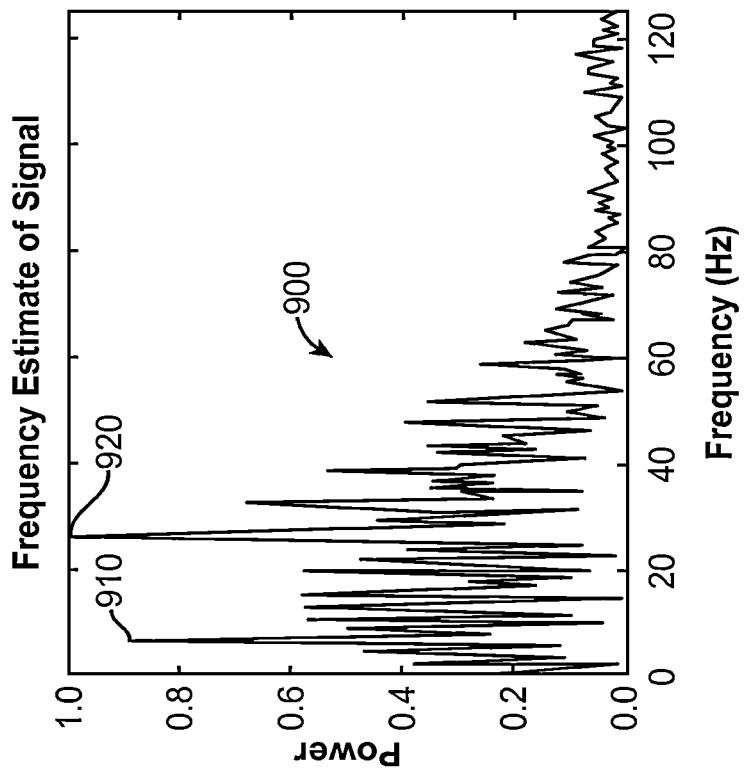
FIG. 9A is a spectrogram corresponding to the frequency content in a region of interest in an electrographic signal according to embodiments using fast Fourier transform averaging.

Frequency spectra for the same sample electrographic signal (e.g., corresponding to a user-selected region of interest 520) are shown in FIGS. 9A and 9B. In these two figures, the x-axis corresponds to frequency in Hz, and the y-axis corresponds to relative power. FIG. 9A is a frequency spectrum 900 obtained by using an FFT approach. FIG. 9B is a frequency spectrum 902 obtained from the same signal by using an LPC approach. If the peak frequencies are deemed to occur at about 10 Hz and 26 Hz, then it can be appreciated by comparing FIG. 9B with FIG. 9A that each of the first peak frequency 910 and the second peak frequency 920 are easier to pick out in the LPC frequency spectrum 902 than they are in the FFT frequency spectrum 900, at least for the reason that the LPC frequency spectrum 902 is much smoother than that of the FFT frequency spectrum 900.

FIGS. 10A and 10B illustrate a comparison of a region of interest and a region of baseline activity. In FIG. 10A, the x-axis corresponds to frequency in Hz, and the y-axis corresponds to relative power. In FIG. 10B, the x-axis corresponds to frequency in Hz, and the y-axis corresponds to a ratio of relative power. In FIG. 10A, the frequency content a region of interest 520 is shown on the same graph with a frequency content of a first region of baseline activity 540 and a frequency content of a second region of baseline activity 540. The dotted trace 1010 corresponds to the frequency content of the region of interest, the trace identified with crosses 1020 corresponds to the frequency content of the first region of baseline activity ("first baseline") and the triangle trace 1030 corresponds to the frequency content of a second region of baseline activity ("second baseline"). FIG. 10B represents a ratio of the region-of-interest frequency content 1010 to the average baseline frequency content (average of 1020 and 1030). In this particular example, a salient frequency may be defined as a frequency that is present in the region of interest 520 but that is not present in either of the first or second regions of baseline activity 540. Thus, in FIG. 10B, it easily can be appreciated that the ratio of power of the region of interest relative to the baseline regions is greatest at about 10 Hz. Specifically, at about the point 1080 on the trace 1060, there is about two times the power in the region of interest than in the average of the first and second baseline regions. In this example then, the salient frequency 1080 is 10 Hz, and the system and method for automatically deriving a parameter set will use 10 Hz as the peak frequency.

It is predictable that a given region of interest 520 selected by a user may be characterized by more than just one salient frequency after the frequency content of the region of interest is analyzed according to embodiments, at least for the reason that the definition of which frequencies are "salient" may vary. The system and method for automatically deriving a parameter set for a detector that depends on a frequency may be customized for different definitions of "salient." In real world implementations of the system and method, the ability to customize the automatic derivation will translate to a user's being able to fine tune the system and method for a particular patient without have to fully appreciate how each individual parameter of the detector relates to how patterns (or other features) of the monitored physiological data are detected. For example, when more than one peak frequency is identified in a user-selected region of interest, the system and method for automatically deriving a parameter set for a half wave detector may choose only one of these frequencies to use as a peak. For example, a salient frequency may be selected as the higher of two or the highest of three or more frequencies. Alternatively, and with reference to block 868 in FIG. 8B, the system may display the plurality of peak (or other "salient") frequencies to the user and prompt the user to select one of them for use in a system and method for automatically deriving a parameter set.

There may be circumstances in which a particular region of interest in a signal (or other sample of a form of physiological data other than an electrographic signal), does not fit well with a particular detector. For example, if after obtaining frequency spectra for a user-selected region of interest and region(s) of background activity, no peak or peaks in frequency are obvious, then a detector that does not require an input related to frequency may be deemed more appropriate. For example, in the RNS SYSTEM described previously, the detection tools a user is able to choose from include a half wave detector, a line length detector, and an area detector. If a system or method for automatically deriving a parameter set cannot find at least one peak frequency in a region of interest (for example, via linear predictive coding or fast Fourier transforms or otherwise), then the system or method may determine that it is more appropriate to use an automatic parameter value derivation method for another type of activity or pattern such as spiking in block 860 or power change in block 846, which may include use of another detection tool, such as the line length tool or the area tool. In the case where an automatic derivation system or method cannot find any detector that seems to fit the characteristics of a given region of interest selected by a user, at block 850, the system or method may resort to a default, which may comprise a particular kind of tool configured in a particular way, or the system or method may communicate to the user that it cannot find a good fit based on the region(s) of interest the user has selected, or the system or method may do both of these things.

It will be apparent that a variety of different methods may be applied to facilitate the robustness and reliability of the set of values that results from the automatic derivation. For example, a method may be configured to evaluate segments of the electrographic signal just prior to and just after a user-selected region of interest. Evaluating segments just prior to and just after the user-selected region of interest could be advantageous if the user has not selected precisely the region containing the signal of interest. Alternatively, or additionally, the method may be configured to divide a particular region of interest into multiple pieces. Evaluating segments within a given region of interest could be advantageous if the signal within the region of interest has more than one feature. For example, the first half of a region of interest may have a feature corresponding to a peak frequency around 10 Hz, and the second half of the region of interest may have spiking activity. (See FIG. 22C for an example of a signal that exhibits a peak frequency in one segment (first half) and spiking in another segment (second half)).

In the case where the analysis of the frequency content of a region of interest 520 (e.g., compared to one or more regions of background activity 540) reveals a salient frequency or where a salient frequency is otherwise identified by the system (e.g., a frequency is selected as a salient one by the computer or a user), then values for three of the parameters of a half wave detector may be automatically derived as described below.

For a given salient frequency, there is a set of possible values for each of the half wave count criterion parameter 194 and the half wave window size parameter 195. Once the system and method for automatically deriving a parameter set for a half wave detector has selected a pair of values for the half wave count criterion parameter 194 and the half wave window size parameter 195, the system and method can select (or a user can be prompted to provide) a value for the minimum half wave width 193. This process is described in more detail below and with reference to block 870 of FIG. 8B.

In a half wave detector such as the half wave detector described in detail above, the half wave count criterion parameter 194 and the half wave window size parameter 195 are related to the minimum frequency that the half wave detector will be tuned to detect as follows:

$$\text{Frequency}_{min} = \frac{(\text{HalfWaveCountCriterion} - 1) \times \frac{1}{2}}{\text{HalfWaveWindowSize}}$$

When a salient frequency 1080 corresponds to the desired minimum frequency for detection, the unknowns in the above equation become the values for the half wave count criterion parameter 194 and the half wave window size parameter 195. Automatically deriving parameter values for a half wave detector according to some embodiments involves sorting the possible values for the half wave count criterion parameter 194 and the half wave window size parameter 195 (for a given salient frequency).

Figure 11A:
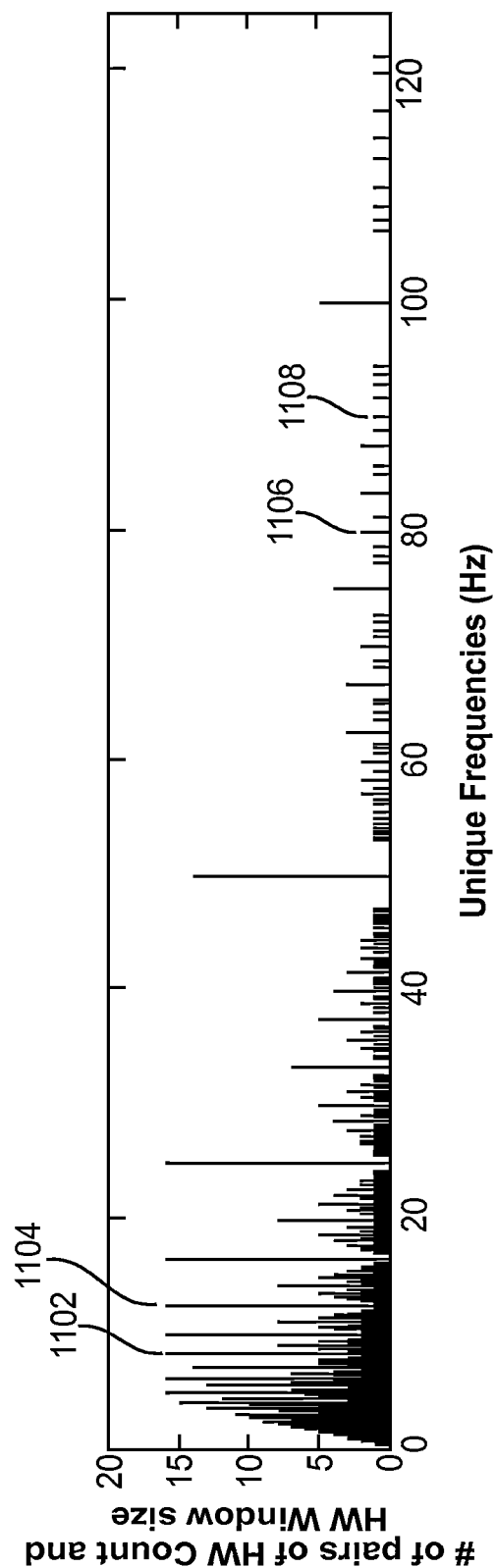
FIG. 11A is a graphical representation of a distribution of data, specifically, a histogram showing the distribution of pairs of possible values of two parameters for a half wave detector related to defining a minimum frequency the half wave detector will detect organized by unique frequencies (on the x-axis), according to embodiments.
Figure 11B:
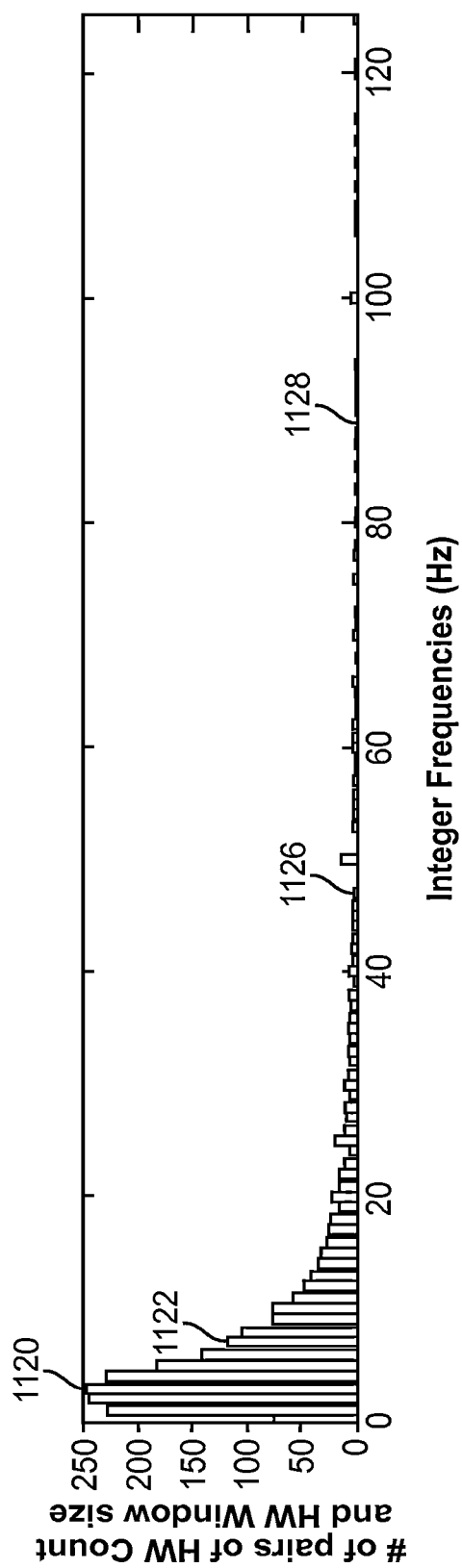
FIG. 11B is a graphical representation of a distribution of data, specifically, a histogram showing the distribution of pairs of possible values of two parameters for a half wave detector related to defining a minimum frequency the half wave detector will detect organized by integer frequencies (on the x-axis), according to embodiments.
Figure 11C:
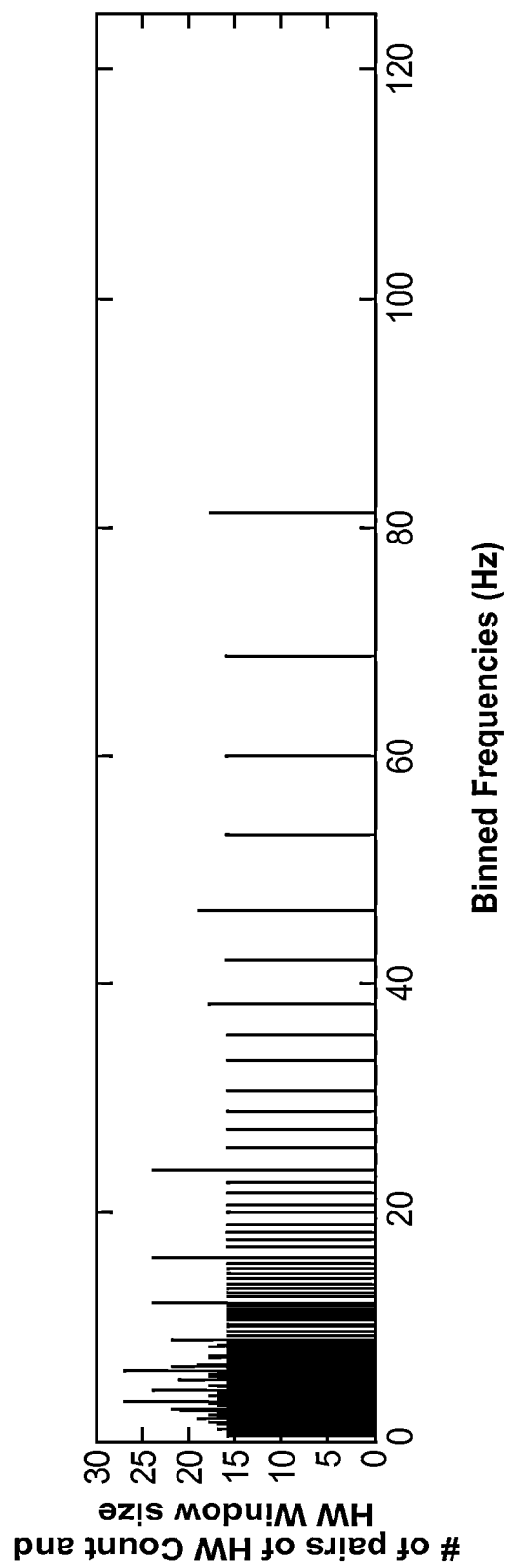
FIG. 11C is a graphical representation of a distribution of data, specifically, a histogram showing the distribution of pairs of possible values of two parameters for a half wave detector related to defining a minimum frequency the half wave detector will detect organized so that the number of pairs in each bin (for a given frequency on the x-axis) will be approximately the same, according to embodiments.

For a given salient frequency, there are a certain number of possible pairs of values for the half wave count criterion parameter and half wave window size parameter that correspond to that frequency. Referring now to FIGS. 11A-11C, three ways of looking at the possible pairs of values for these parameters are described. In each of FIGS. 11A-11C, the y-axis corresponds to the number of pairs of the two parameters that will result in a given frequency (the y-axis in the figures is labeled "Number of Count & HW Window Combinations"). The x-axis corresponds to the frequency (in Hz) to which each number of pairs corresponds.

In FIG. 11A, the x-axis corresponds to unique frequencies (e.g., 9.7 Hz, 10.2 Hz, 11.3 Hz etc.). In FIG. 11B, the x-axis corresponds to integer frequencies only (e.g., 9 Hz, 10 Hz, 11 Hz). In FIG. 11C, the x-axis corresponds to an organization of the possible frequencies based on how many pairs of the half wave count criterion and half wave window size are associated with each frequency range (in FIG. 11C, the x-axis is labeled "Binned Frequencies"). Put another way, FIGS. 11A-11C correspond to histograms where each 'bin' associated with a given frequency represents the number of pairs of possible values for the half wave count criterion and half wave window size for a given frequency range.

With particular reference to FIG. 11A, it can be appreciated that some frequencies, especially in the lower range of the frequencies shown in FIGS. 11A-11C, have over 16 possible pairs of values. Other frequencies, particularly in the higher range of the frequencies shown in FIGS. 11A-11C, have only one or two possible pairs of values. For example, in the bin 1102 at about 8 Hz and in the bin 1104 at about 10.5 Hz in FIG. 11A, it appears that there are sixteen possible pairs for the half wave count criterion/half wave window size combination. At about 80 Hz in the bin 1106 and at about 90 Hz in the bin 1108, it appears that there are only two pairs or one pair, respectively.

In FIG. 11B, the histograms are binned in integer values rather than actual values of a given half wave count criterion/half wave window size combination. For example, if the frequency is 8.2 Hz the half wave count criterion/half wave window size combination would be contained within the 8 Hz bin. As might be expected, the number of possible pairs for each integer value goes up at the lower frequencies and is lower at the higher frequencies. For example, there appear to be about 248 pairs of possible values for the half wave count criterion and the half wave window size in the bin 1120 at about 4 Hz and about 110 pairs in the bin 1122 at about 8 Hz; whereas there appear to be less than ten pairs in each of the bin 1126 at about 48 Hz and the bin 1128 at about 90 Hz.

A more optimal binning of the possible values of the parameter pairs versus frequency may be accomplished by defining a bin according to a total number of pairs. For example, in FIG. 11C, each bin is defined as nominally including sixteen pairs. (A given bin may have a few more or less pairs than sixteen pairs for a given frequency: for example, if there were three pairs of values for the half wave count criterion parameter 194 and the half wave window size parameter 195 that corresponded to a frequency of 12.3 Hz, and fifteen pairs for the half wave count criterion parameter and half wave window size parameter that corresponded to a frequency of 12.5 Hz, then the bin that includes these two frequencies would have a total of eighteen pairs rather than the nominal value of sixteen pairs). In the binning method reflected in FIG. 11C, each bin will correspond to a similar number of pairs. The frequency range for each bin will be associated with a range that covers the lowest frequency yielded by a pair in the bin to the highest frequency yielded by a pair in the bin.

Within each bin of FIG. 11C, the pairs may be organized according to the values for the half wave count criterion 194 (i.e., from lowest to highest) and then by the minimum frequency of detection a pair would yield (i.e., from the lowest to the highest frequency). A reasonable assumption might be made that, with all else being equal, a detector that requires fewer counts in order to decide whether something should be detected is more sensitive than a detector that needs more counts before triggering a "detection." With that assumption, the possible values for the half wave count criterion parameter 194 and the half wave window size parameter 195 in each bin are essentially ordered from most sensitive to least sensitive. Once the pairs are ordered in this way, when a user instructs the system to adjust the sensitivity of the relevant half wave detector (for example, by sliding an indicator in a slider 670), the system and method for automatically deriving a parameter set for that half wave detector can react to the user's command by effectively moving around (e.g., up or down) within a bin in order to try out or choose new pairs of values for the half wave count criterion 194 and the half wave window size parameter 195 (this sensitivity adjustment may be presented to a user in the form of a "less specific/more specific" option as was described with reference to FIG. 6.

For a given salient frequency, according to embodiments, the system and method for automatically deriving a parameter set will select the bin which most closely matches the salient frequency (e.g., if a bin covers a frequency range from 12.3 to 12.5 Hz and the salient frequency is 12.5 Hz, then the algorithm will select that bin). The algorithm may select a single one of the pairs of values for the half wave count criterion parameter and the half wave window size such as single pair in about the middle of the bin. If when a simulation corresponding to a test run of the algorithm is ultimately displayed to the user, the user decides the half wave detector is not configured to detect what the user wants, then by adjusting the sensitivity slider 640 to be more or less specific, the user can try out any of the rest of the pairs of values in that same bin. Alternatively, which pair of values the algorithm initially chooses within a particular bin may be dictated by another automatic computation or computations. In still other embodiments, choices of parameter value pairs after an initial parameter value pair has been selected and tested may be accomplished using automatic computation(s). Importantly, and although what the system and method is doing in the parameter space may not be at all intuitive to the user, the user nonetheless will appreciate that he can expect the behavior of the system to adjust itself in one direction or the other based on his sensitivity adjustments.

Once the system and method for automatically determining a parameter set for the half wave detector has identified the minimum frequency for detection using the salient frequency 1080 by selecting a half wave count criterion 194/half wave window size 195 pair of values, it can determine a value for the minimum half wave width parameter 193. The minimum half wave width corresponds inversely with a maximum half wave frequency HWfreq$_{max}$. In some embodiments, a requirement can apply, for example, that the maximum half wave frequency HWfreq$_{max}$ be N times larger than the minimum half wave frequency with the Nyquist frequency, which is the sampling rate divided by 2, as the maximum possible value. In some real-world examples of sets of values for the parameters of a half wave detector in the RNS SYSTEM, the value for the minimum half wave width may be either 0 ms or 4 ms These values correspond to a maximum half wave frequency of 125 Hz or 62.5 Hz, respectively. This experience suggests that a value of N between 5 and 10 may be appropriate in many cases.

Although in this example the system and method for automatically deriving a parameter set for a half wave detector has been described as determining the values for the relevant parameters in a particular sequence, it will be appreciated that this sequence may be different, for example, depending on what a detector is intended to detect. For example, in an embodiment where a half wave detector is being configured to detect a pattern of rhythmic activity in a monitored electrographic signal, then the system and method for automatically deriving a parameter set for a half wave detector may begin by selecting a value for a half wave count criterion parameter. However, in an embodiment where a half wave detector is being configured to detect the occurrence of spikes in a monitored electrographic signal, then the system and method for automatically deriving a parameter set for a half wave detector may begin by selecting a value for a half wave hysteresis parameter. Thus, it will be appreciated that the parameters relevant to a given detector may be automatically derived in different sequences depending on, for example, the nature and type of activity the detector is intended to detect. Alternatively, or additionally, other computations may be used by the algorithm in between the operations for determining values for the parameters detailed herein. For example, a computation to determine a value for some additional parameter may be inserted between an operation for determining whether a region of interest exhibits a salient frequency and an operation for determining the values for a half wave count criterion parameter/half wave window size parameter pair.

After the user has selected at least one region of interest 520 and the system and method for automatically deriving a parameter set for a half wave detector has identified values that ultimately correspond to a minimum frequency for detection and a maximum frequency, the system and method may determine a value for the half wave hysteresis parameter 191.

In some embodiments, and when the physiological data is an electrographic signal, the value assigned to the half wave hysteresis parameter 191 may correspond to a minimum amplitude that a given half wave (e.g., a transition in the waveform from a positive slope to a negative slope) must meet or exceed before the transition will be defined as a half wave. Referring again to FIGS. 1 and 2, it generally will not be desirable to define every transition in the signal as a half wave. Rather, it may be desirable to discount as mere "perturbations" those transitions that never exceed a certain threshold. In the example of FIG. 1B, each of the half wave

2 120 and the half wave #3 130 were deemed to be mere perturbations and therefore were both accounted for by including them as part of the first half wave 202 of FIG. 2. Similarly, the half wave #5 150 and the half wave #6 160 of FIG. 1B were each deemed to be mere perturbations and therefore were ignored in defining the second half wave 208 in FIG. 2. Since the hysteresis parameter value is in amplitude units according to some embodiments, a particular half wave that only lasts a short time may still be deemed to comprise a half wave if the amplitude threshold is met or exceeded (see, e.g., the sixth half wave 320 of FIG. 3).

Generally, the value of the half wave hysteresis parameter 191 is used by the detection algorithm to allow a half wave detector to ignore small perturbations (which might be attributable to, for example, noise), in a function similar to that of a low pass filter.

In a system and method for automatically deriving a parameter set for a half wave detector according to embodiments, the possible values for the half wave hysteresis parameter 191 may range from 0 to 255 (amplitude units). The system and method may test each of these possible values and then select one for the half wave hysteresis parameter 191 that corresponds to some minimum amplitude that has to be met or exceeded before a transition may be counted as a half wave. For example, all of the possible hysteresis values from 0 to 255 may be tested for a given region of interest 520 to determine what percentage of the total number of transitions identified in that sample are identified as half waves. If the value for the half wave hysteresis parameter 191 is set to a non-zero value, this value will reduce the number of half waves that are identified in the sample.

Once the system and method for automatically deriving a parameter set for a half wave detector has determined the percentage of half waves that exceed the minimum half wave width 193 for each value of the half wave hysteresis parameter 191, the system and method can select one of those hysteresis values to use. For example, a value for the half wave hysteresis parameter 191 may be selected so as to maximize the percentage of half waves that exceed the minimum half wave width 193 while minimizing the hysteresis parameter value 191.

Figure 13:
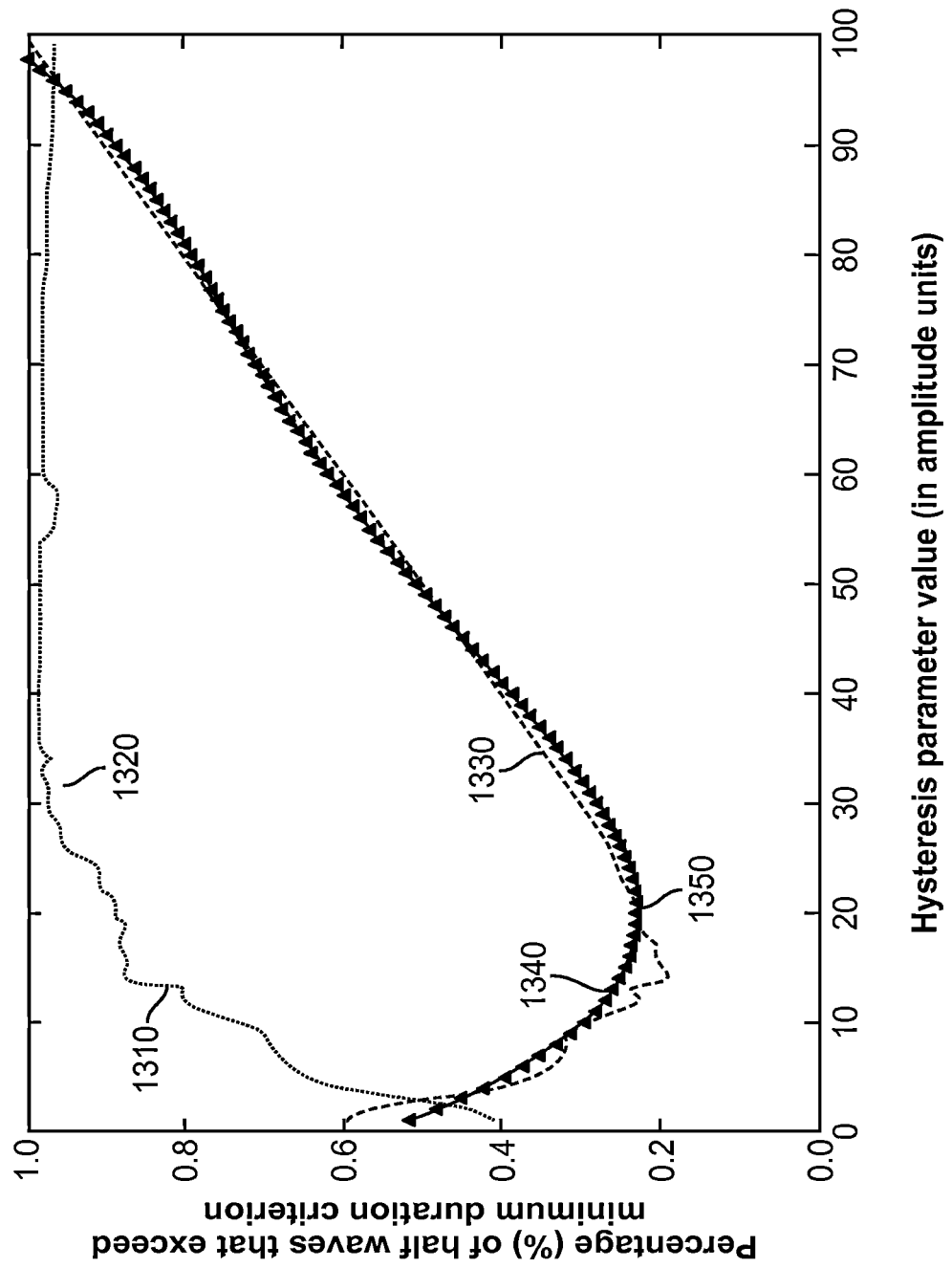
FIG. 13 is a graphical representation of method for selecting a value for a hysteresis parameter for a half wave detector configured to look for rhythmic activity according to embodiments.

Referring now to FIG. 13, in an embodiment, a value for the half wave hysteresis parameter 191 may be selected by identifying the minimum hysteresis parameter value that maximizes the percentage of half waves that exceed a minimum half wave width 193. In FIG. 13, the y-axis represents the percentage of half waves in a sample that exceed a minimum duration (time) criterion for a given value of the half wave hysteresis parameter 191 on the x-axis. The dotted line 1310 in FIG. 13 shows which values of the possible values for the half wave hysteresis parameter 191 correspond to the highest percentage of half waves in the sample. In this example, it appears for a hysteresis value just higher than 30, the percentage of half waves with a duration meeting the minimum duration criterion reaches a maximum and thereafter levels off.

The dashed line 1330 represents the distance of the dotted line 1310 from the point (0,1) on the graph of FIG. 13. The system can be configured to choose a value for the half wave hysteresis parameter 191 that minimizes the distance from the point (0,1) by modeling the distance 1330 by a fourth order polynomial. The result of this modeling is represented by the line drawn with triangles 1340 in FIG. 13. The value selected for the hysteresis parameter 191 can be chosen as the minimum value 1350 on the triangle-line 1340, which appears as though it occurs at about a value of 20.

In some embodiments, the system and method for automatically deriving parameter values for a half wave detector may determine a value for the minimum half wave amplitude parameter 192 using a value for the half wave hysteresis parameter value 191, for example, the hysteresis parameter value selected according to the process described above. Given a selected value for the hysteresis parameter 191, the number of half waves occurring (i.e., the "half wave counts") in a region of interest and in a region or regions of baseline activity may be determined. Once the number of half waves is determined, the half waves can be sorted (e.g., into bins in a histogram) according to amplitude or ranges of amplitude. The number of half waves in each bin can be normalized by dividing the sum in a bin by total number of half waves counted in the relevant sample (e.g., in a sample corresponding to the region of interest or in a sample corresponding to the region(s) of baseline activity).

The results of this process of sorting the number of half waves in each bin for the region of interest and the region(s) of baseline activity may be used to identify an amplitude for which the percentage of half waves in the region of interest (e.g., the normalized half wave counts for the region of interest) is greater than the percentage of half wave counts in the baseline region(s). In this way, the system can determine a starting parameter value for the minimum half wave amplitude parameter. The half wave amplitude parameter can subsequently be adjusted by the user using a sensitivity adjustment such as a signal amplitude slider 640. An advantage of normalizing the half wave count in each bin by the total number of half waves in the sample is that the calculation is then independent of the sample size. For example, if the baseline region were twice as long as the region of interest, the normalized half wave counts could still be compared between the regions.

Figure 14:
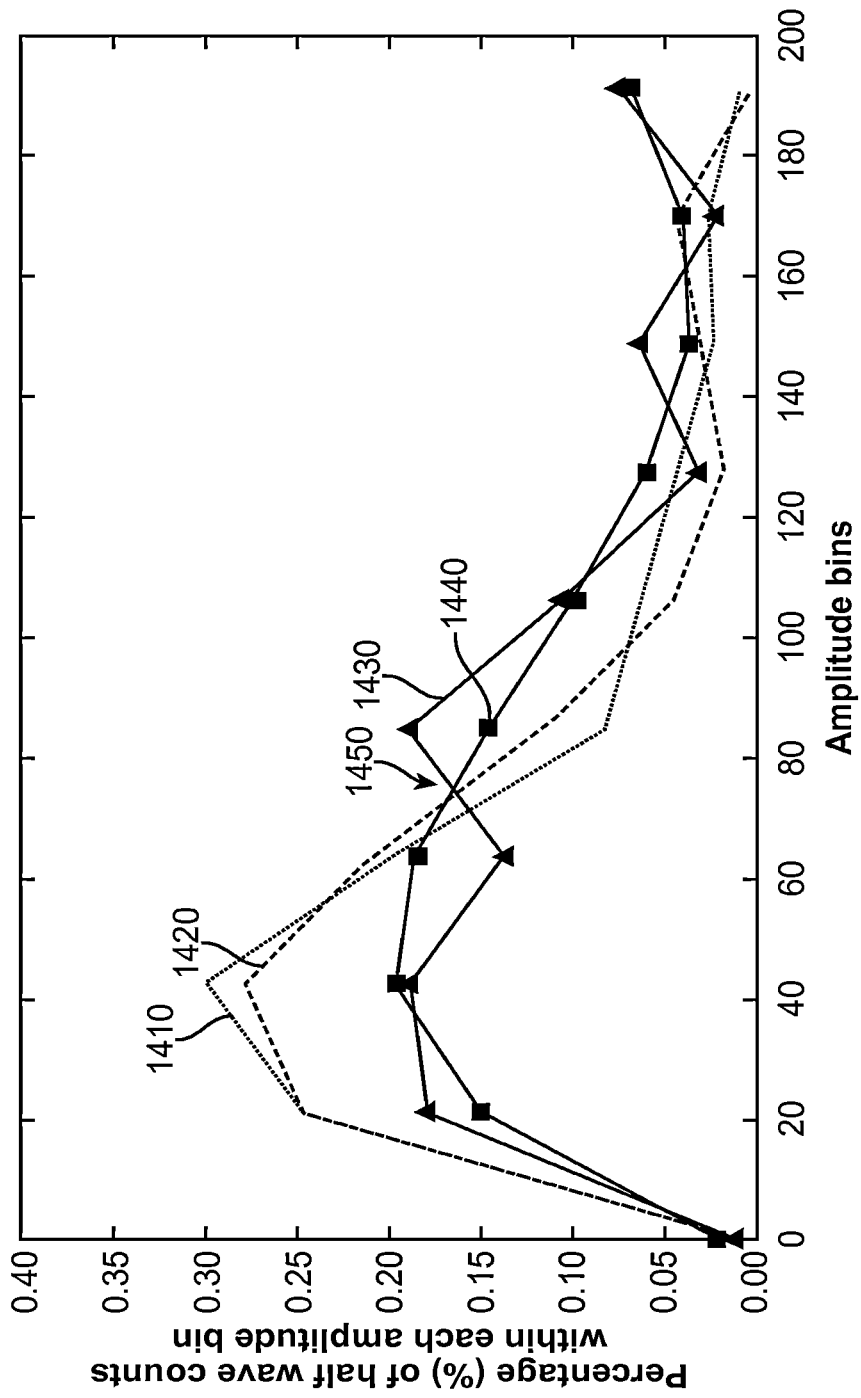
FIG. 14 is a graphical representation of a method for selecting a value for a minimum half wave amplitude parameter for a half wave detector configured to look for rhythmic activity according to embodiments.

Referring now to FIG. 14, four plots are shown which illustrate the method of identifying a point where the normalized half wave counts in a region of interest begins to be greater than the normalized half wave counts in the baseline region(s). In this figure, the x-axis represents bins of amplitude and the y-axis represents the percentage of half wave counts within each amplitude bin. The dotted line 1410 is the normalized half wave counts for the baseline region(s), and the plot shown with the triangles 1430 is the normalized half wave counts for the region of interest. The plots may be modeled using for example a fourth order polynomial in order to smooth the data to better identify the point at which there is a higher percentage of half wave counts in the region of interest relative to the baseline region. The dashed line 1420 and the plot with squares 1440 are the fourth order polynomials of the dotted line 1410 and the plot with triangles 1430, respectively.

In FIG. 14, at about the point 1450 corresponding to about 70 amplitude units, it can be appreciated that the percent of half wave counts in the region of interest 520 begins to be greater than the percent of half wave counts in the region(s) of baseline activity 540. Thus, in this example, the system and method for automatically deriving a set of parameters for a half wave detector may select a value of around 70 (amplitude units) as an initial value for the half wave minimum amplitude parameter 192. In some embodiments, this starting parameter value can subsequently be adjusted with feedback from the user, such as by using a "signal amplitude" slider 640 to detect less or detect more.

The foregoing example of a system and method for automatically deriving a parameter set for a half wave detector describes how values for five of the parameters used in a half wave detector may be automatically established based on a region of interest selected by a user and one or more regions of baseline activity selected by a user or a computer. The parameters for which at least a starting value is selected are the (1) half wave count criterion parameter 194; (2) the half wave window size parameter 195; (3) the minimum half wave width parameter 193; (4) the half wave hysteresis parameter 191; and (5) the minimum half wave amplitude parameter 192. In the particular half wave detector described with reference to FIG. 1, the other parameters include the qualified analysis window count parameter 196 and the detection analysis window size parameter 197 (for establishing an "X of Y criterion for detection). In some implementations of a half wave tool, these two parameters are also sometimes referred to as the "bandpass threshold" and the "detection analysis window size", respectively.

The qualified analysis window count parameter 196 and the detection analysis window size parameter 197 work together in the half wave detector to specify a duration and consistency for a pattern of activity that is represented in the electrographic signal that will trigger the tool to 'detect'. For example, a value of 8 for the qualified analysis window count parameter 196 and a value of 2048 ms for the detection analysis window size parameter 197 translate into a requirement that half waves meeting the criteria established by the five parameters discussed above would have to occur in at least 8 128 ms windows within 2048 ms. A system and method for automatically deriving a parameter set for a half wave detector may select starting values for the qualified analysis window count parameter 196 and the detection analysis window size parameter 197 such that when using the set of detection parameters identified by the algorithm, detection would occur in the region of interest. In other words, simulations can be run with the starting values for the half wave count criterion parameter 194, the half wave window size parameter 195, the minimum half wave width parameter 193, the half wave hysteresis parameter 191, and the minimum half wave amplitude parameter 192, and various combinations of the qualified analysis window count parameter 196 and the detection analysis window size parameter 197 to determine the largest qualified analysis window count parameter 196 value which would result in detection in the selected region of interest.

Spike Activity/Half Wave Detector

Referring now to FIG. 8C, embodiments will be described of a system and method for automatically deriving a parameter set for a half wave detector where the physiological data at issue comprises electrocorticographic signals and the type of activity in the region(s) of interest has been determined to be (for example, by an activity type algorithm such as Algorithm A in FIG. 8A) spiking. Generally, spiking activity in physiological signals (e.g., EEG, ECG, EMG, etc.) may be of clinical significance in many disorders or conditions. Spiking activity in ECOGs may be considered a hallmark of epileptiform activity in epilepsy.

Spiking activity may be characterized by a basic structure associated with each spike that may be referred to as a "spike complex" or "SC". A half wave detector can be configured to look for spiking with similar parameters as a half wave detector for detecting rhythmic activity. For example, in a given region of interest, a spike complex may be defined as the occurrence of two consecutive half waves with opposite slopes (e.g., a positive slope followed by a negative slope), each of which exhibits a higher amplitude than the amplitude of some or most of the other half waves with which the region of interest may be characterized. Some examples of regions containing spiking activity and characterizable by at least one spike complex are shown in FIGS. 12A-12E where the x-axis is in units of time and the y-axis is in units of amplitude.

Figure 12A:
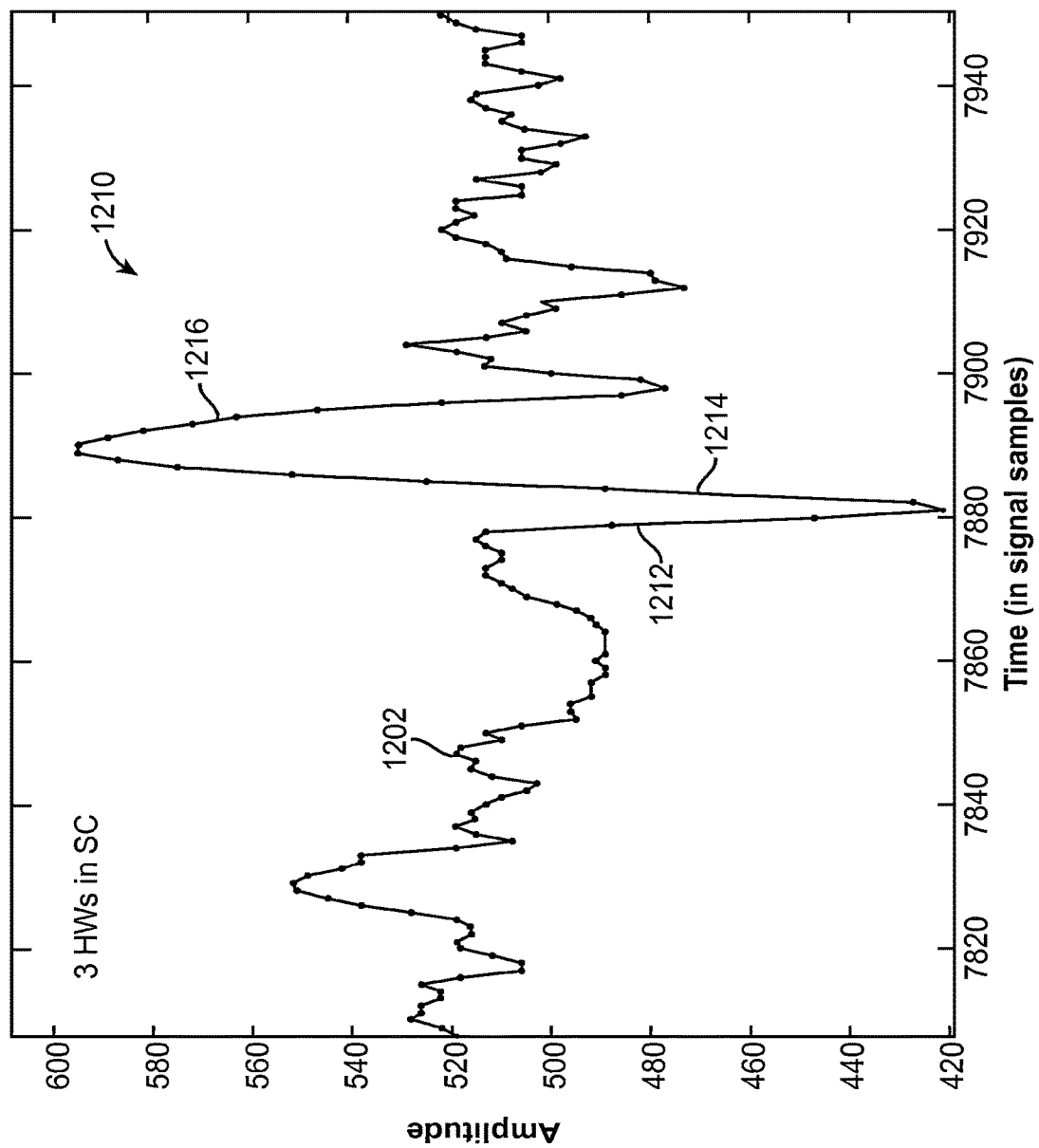
FIG. 12A, FIG. 12B, FIG. 12C, FIG. 12D, and FIG. 12E each is a graphical representation of spiking activity as it may occur in a representation of an electrographic signal as sensed from a patient.

In FIG. 12A, a portion 1202 of an ECOG signal is shown with a spike complex 1210 comprised of three half waves, a first SC half wave 1212 characterized by a positive slope, a second SC half wave 1214 characterized by a negative slope, and a third SC half wave 1216 characterized by a positive slope. It is apparent that the three SC half waves 1212, 1214, and 1216 stand out from the other transitions or half waves in the portion 1202 because each of the SC half waves 1212, 1214, and 1216 have greater amplitude than the other transitions or half waves.

Figure 12B:
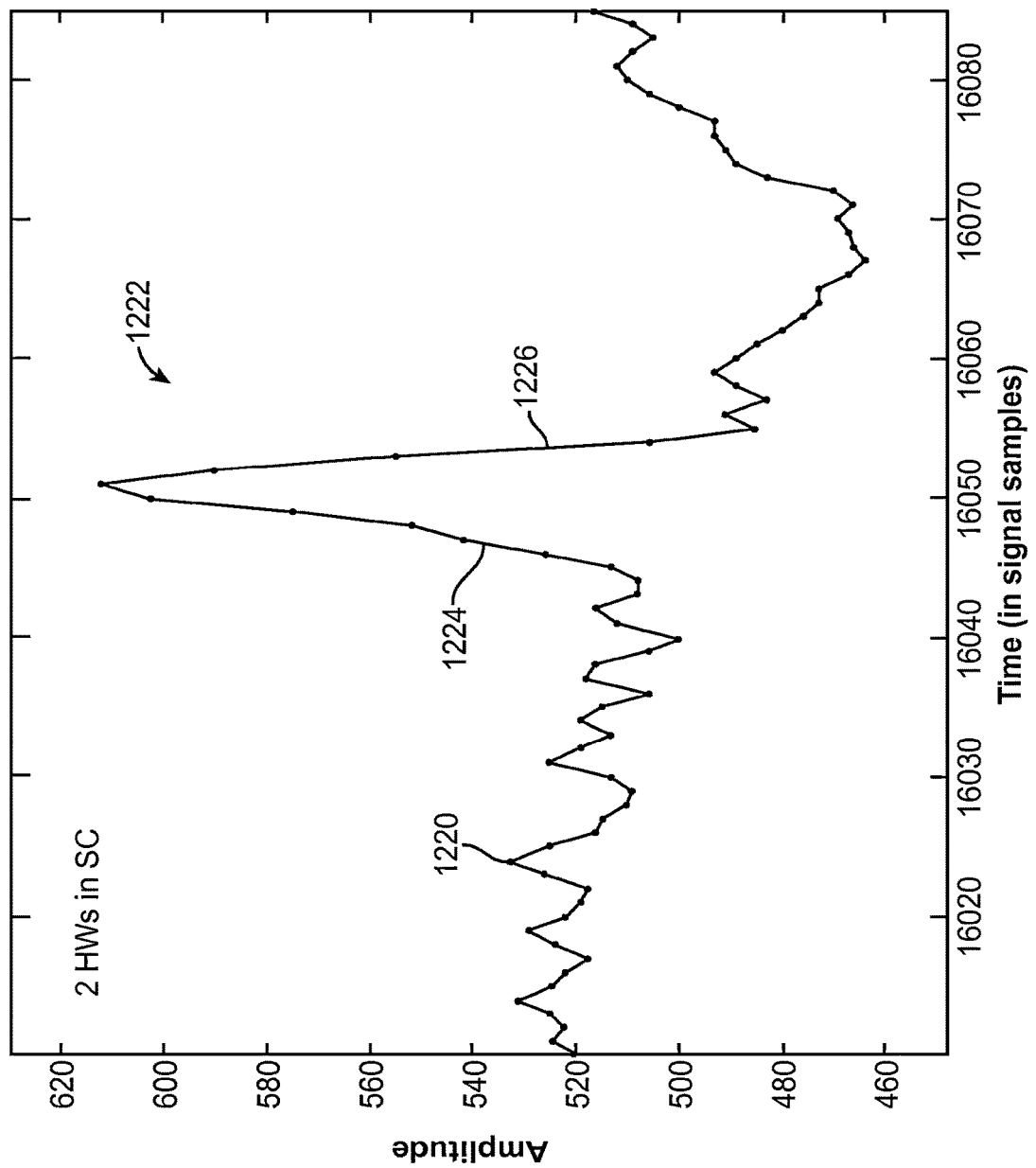
Figure 12C:
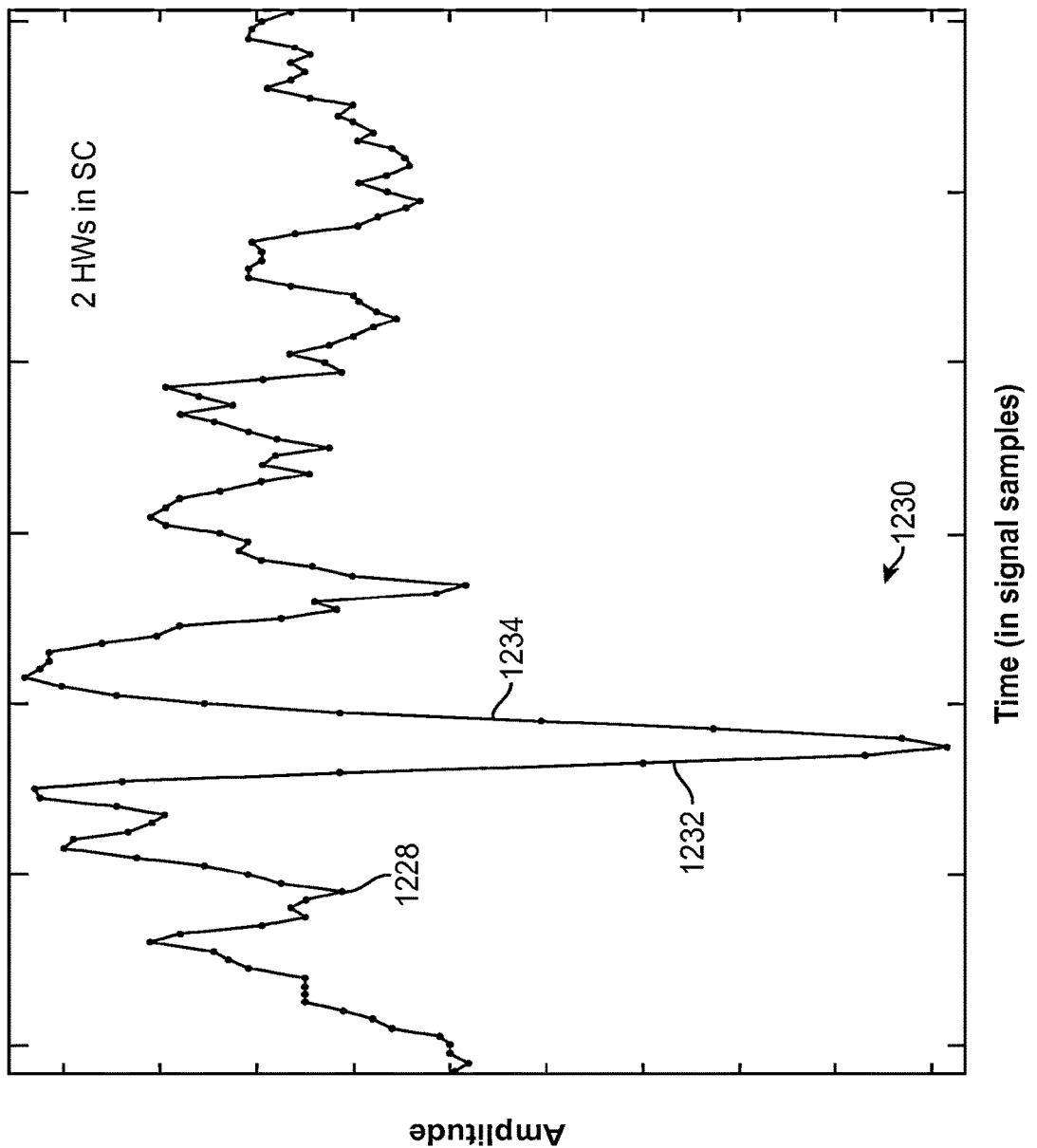

In FIG. 12B, a portion 1220 of an ECOG signal is shown with a spike complex 1222 that is comprised of only two half waves that stand out from the rest, namely, a first SC half wave 1224 with a positive slope and a second SC half wave 1226 with a negative slope. And in FIG. 12C, a portion 1228 of an ECOG signal is shown with a spike complex 1230 that is also comprised of only two half waves, but in this case the spike complex begins with a first half wave 1232 characterized by a negative slope and ends with a second half wave 1234 characterized by a positive slope.

Figure 12D:
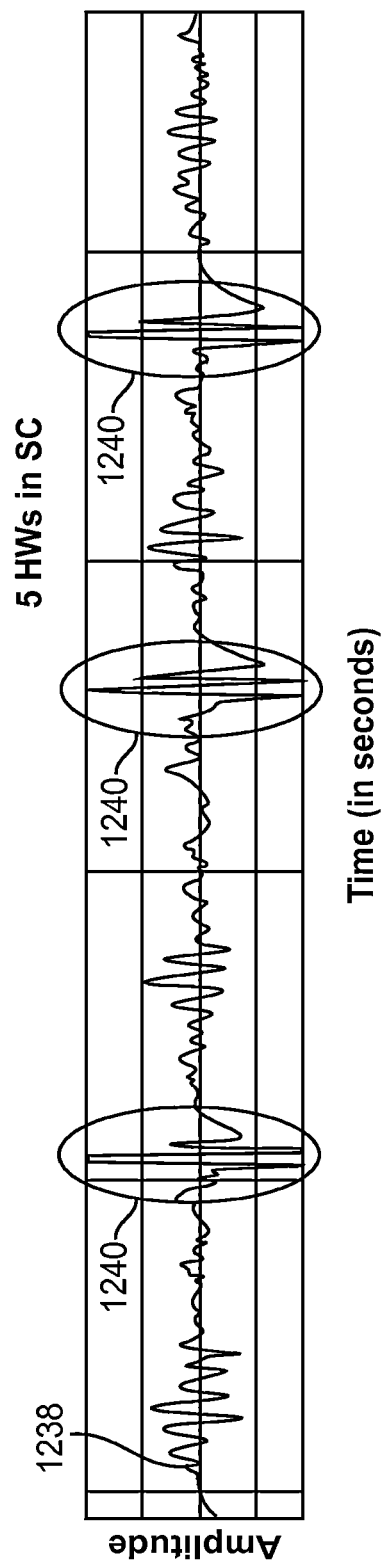
Figure 12E:
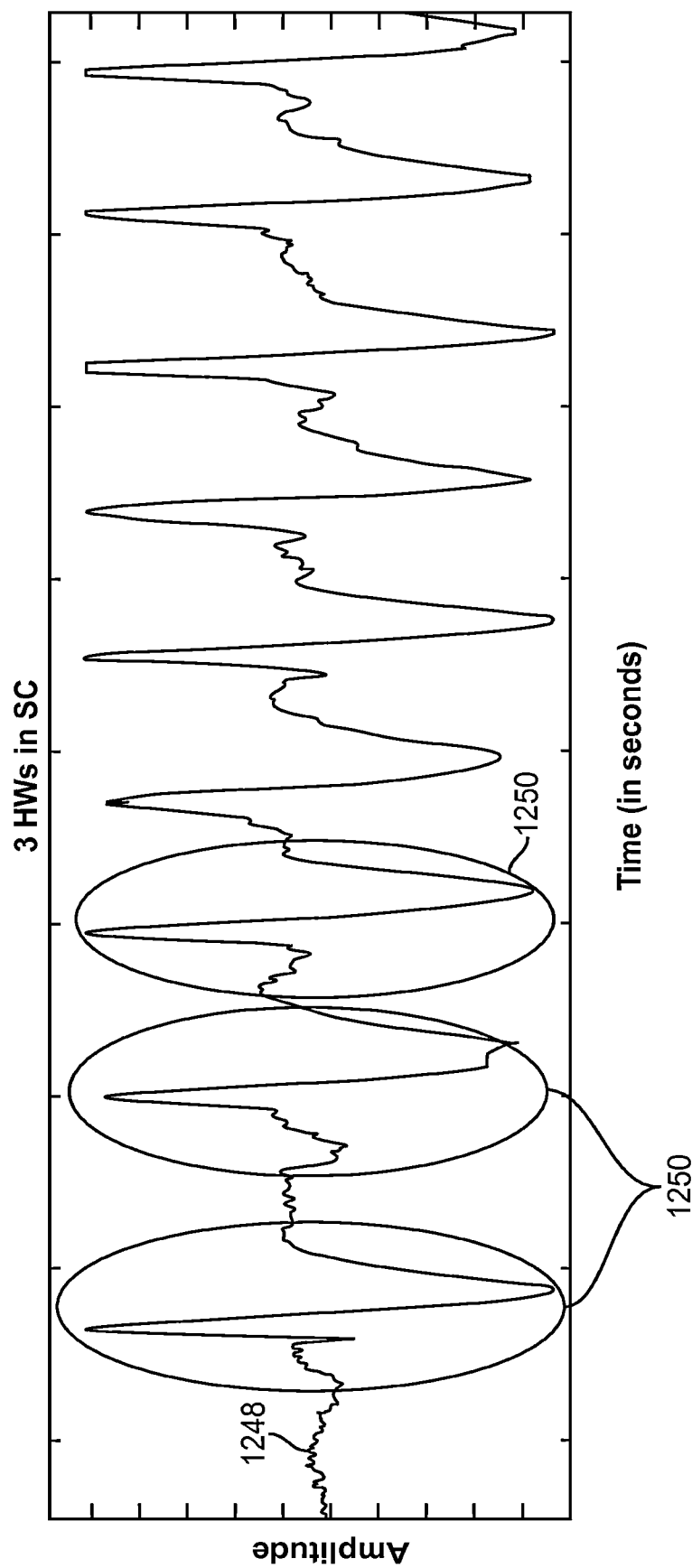

In FIG. 12D, each of the spike complexes 1240 shown in the signal portion 1238 are composed of a set of five half waves that are easily discernible from other activity in the signal portion. In FIG. 12E, each of the spike complexes 1250 in the signal portion 1248 is characterized by three SC half waves.

It should be appreciated that, for a given user-selected region of interest in which spike complexes occur, a system and method for automatically deriving a parameter set for a spike detector may sort the spike complexes using one or more features, such as the number of half waves in a spike complex, the amplitude of the half waves that comprise a spike complex, the duration of a spike complex or the duration of each half wave that makes up a given spike complex, and so on and so forth.

In one embodiment, and with reference now to FIG. 8C, once a user has selected a region or regions of interest (and, optionally, either the user or the computer has selected one or more regions of baseline activity), and at block 830 an activity type algorithm has selected "spiking", then a system and method for automatically deriving a parameter set for a half wave detector configured to look for spikes is invoked at block 860.

The first half wave detector parameter with which the automatic derivation is concerned may be the half wave hysteresis parameter 191. In light of the discussion of this parameter in connection with the description of a half wave detector configured to look for rhythmic activity, it should be appreciated that the half wave hysteresis parameter 191 can be used to disregard half waves in a region of interest that have an amplitude less than the smallest amplitude half wave within a spike complex. Establishing a value for the hysteresis parameter 191 at the outset thus allows the algorithm to eliminate half waves that are too small to be considered part of any spike complex in the region(s) of interest, including but not limited to half waves associated with noise in the signal.

For detecting spiking, a goal for a half wave detector would be to detect the spike complexes that occur in the region(s) of interest. If too high a value for the hysteresis parameter 191 is selected by the automatic derivation system and method, then some half waves that form a part of a spike complex may be excluded by the spike detector. On the other hand, if too low a value for the half wave hysteresis parameter 191 is selected, then too many half waves are likely to be included such that the spike complexes may not be easily discerned from interspike activity including but not limited to signal noise. Accordingly, a value for the half wave hysteresis parameter 191 may correspond to a target that represents a compromise between over-inclusion or under-inclusion of half waves in a given instance of a spike detector. More particularly, such a target may aim to have a high enough number of half waves detected to completely include all of the half waves that make up a spike complex but to not include so many half waves that the spike complexes are obscured.

More particularly, and with reference now to FIG. 18 and to block 861 of FIG. 8C, in an embodiment, a value for the half wave hysteresis parameter 191 may be selected as described below. First, a total number of half waves in the region(s) of interest are counted (based on some predefined sampling rate). Then, the system and method calculates how many of the half waves in that total would remain for each possible value of the hysteresis parameter 191. An objective would be to choose a value for the hysteresis parameter that would include all of the half waves in the spike complex(es) but that is not so low or so high a value that too many or too few half waves are included.

An example in which a value of about 50 for a half wave hysteresis parameter 191 ultimately is selected by a system and method for automatically deriving a parameter set for a half wave detector configured to look for spiking activity will now be described with reference to FIG. 18. In the plot 1800 of FIG. 18, the x-axis represents the possible values for the hysteresis parameter in units of amplitude (i.e., at a hysteresis value of 75, half waves with an amplitude of less than 75 amplitude units will be excluded by the half wave detection algorithm). The y-axis represents the number of half waves that will be counted in a given user-selected region(s) of interest for a given value of the hysteresis parameter. For example, if the value for the half wave hysteresis parameter 191 is set at 25, about 115 half waves in the region(s) of interest will be recognized by the half wave detection algorithm.

Figure 18:
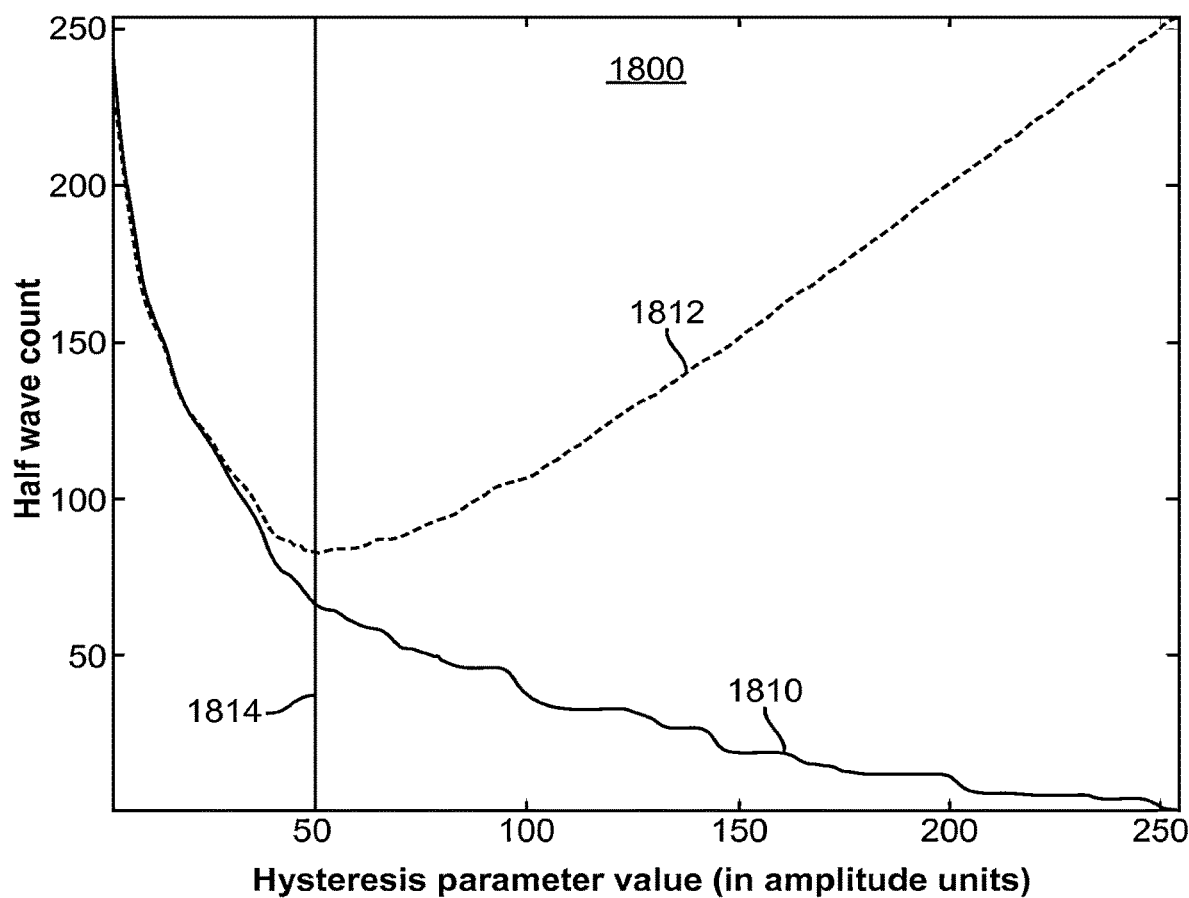
FIG. 18 is a graphical representation of method for selecting a value for a hysteresis parameter for a half wave detector configured to look for spiking according to embodiments.

Generally, it can be appreciated from the shape of the solid line 1810 in FIG. 18 that the half wave count in a region or regions of interest versus the possible hysteresis parameter values may be modeled as an exponential decay. In this particular example, a 5-point moving average was used to smooth the curve. The excursion of the line 1810 shows that the half waves that would be counted by the detection algorithm in a signal that has half wave content similar to that in the region(s) of interest may vary widely for very low values for the hysteresis parameter 191 (e.g., for values of the hysteresis parameter below about 20, somewhere between 140 and 225 half waves in a portion of a sensed signal corresponding to the region(s) of interest would be recognized by the detection tool). And for values of the hysteresis parameter 191 above about 110 units, the half waves that would be counted may be about 25 or less. In the example shown in FIG. 18, hysteresis parameter values between about 25 and 75 are likely to yield the most repeatable and consistent count of half waves.

In order to narrow the hysteresis parameter down to one value, a method for automatically deriving a parameter set for a spiking activity detector may select a value that seems to represent the best compromise between over- and under-inclusion of half waves. Determining such a value may be accomplished, for example, by measuring a Euclidean distance-to-origin for the curve 1810. The Euclidean distance-to-origin corresponding to the points on the curve 1810 is represented by the dashed line 1812 in FIG. 18. The lowest point on the curve 1812 corresponds to the shortest or minimum distance to the origin (i.e., the point 0,0 on the plot 1800 of FIG. 18). The lowest point on the curve 1812 also corresponds to a hysteresis value of about 50. In this particular example, then, a system and method for automatically deriving a parameter set for a spiking activity detector may select 50 as the value for the hysteresis parameter 191.

In some embodiments, the system and method may select a value for the hysteresis parameter 191 based on data in the region of interest for a single patient. In other embodiments, the data on which selection of a value for the hysteresis parameter 191 is based may include data from one or more user-selected regions of interest for a particular patient as well as data from other patients (such as from other patients with a demographic element in common with the patient associated with the user-selected region(s) of interest). In such cases, it may be useful to normalize the x and y axes to the maximum values before calculating the Euclidean distance to the origin.

Figure 19:
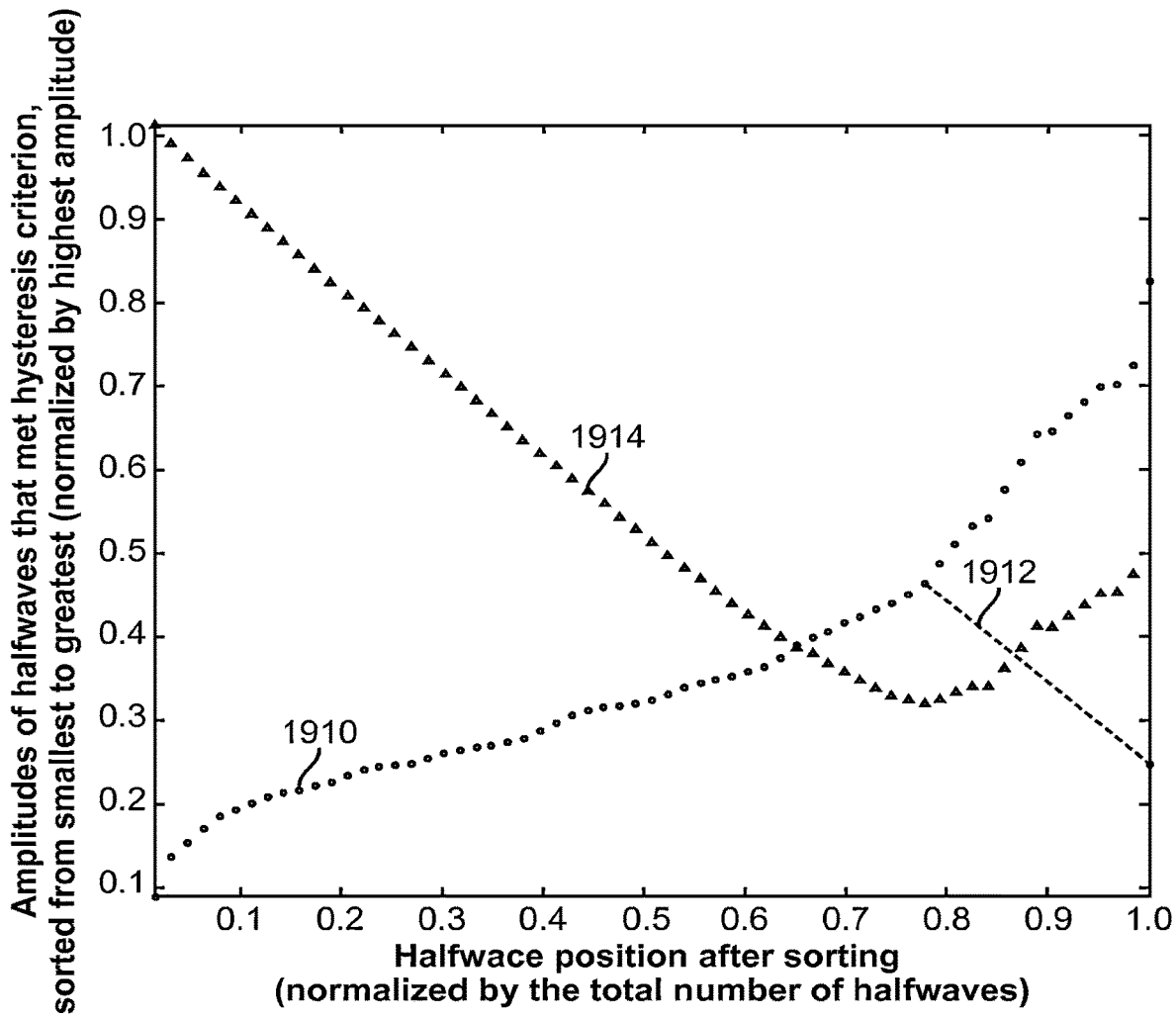
FIG. 19 is a graphical representation of a method for selecting a value for a minimum half wave amplitude parameter for a half wave detector configured to look for spiking according to embodiments.

With reference now to block 862 of FIG. 8C and FIG. 19, after a system and method for automatically deriving a parameter set for a half wave tool configured as a spike detector has selected a value for the hysteresis parameter 191 based on the user-selected region(s) of interest, the half waves that are not excluded by the hysteresis limit are sorted based on amplitude, for example, from smallest to highest amplitude. When a region of interest comprises spike activity, the half wave amplitudes initially tend to grow slowly and then more rapidly for higher amplitudes, such that the half wave rate of growth (slope) in a region of interest containing spike complexes usually starts slow and ends up high. In other words, when the half waves are ordered by amplitude, if there are spike complexes in the signal, there is often an abrupt transition between the low amplitude half waves (which are not associated with the spikes) and the high amplitude half waves (which are associated with spikes). Such a rate of growth is illustrated in FIG. 19. The y-axis corresponds to the half wave amplitude (in FIG. 19, the half wave amplitude values are normalized so that the maximum possible amplitude correspond to "1" and the minimum possible amplitude is close to "0"). The x-axis corresponds to the half wave index when sorted by half waves and normalized so that the maximum possible value is "1" and the smallest possible value is close to "0"). The dotted line 1910 represents the sorted amplitudes corresponding to the half waves that remain in the region(s) of interest after some half waves have been eliminated based on an applied hysteresis (i.e., where the hysteresis parameter has a non-zero value). The sorted amplitudes start out relatively low and trend higher. The dashed line 1912 represents the distance from a point on the curve 1910 to a point at about (1, 0.25) and the triangle line 1914 represents a minimum distance from the point (1, 0.25). An intermediate slope (rate of growth) occurs around the point closer to the corner point (1,0).

In an embodiment of a system and method for automatically deriving a parameter set for a spike detector, a value for a minimum half wave amplitude 192 is selected which corresponds to a point on FIG. 19 corresponding to an amplitude closest to the point (1, percent), where "percent" is a selectable parameter for. In an embodiment, a default value for the percent parameter may be 25%. Thus, in the sorted amplitudes curve 1910, that amplitude which minimizes the distance to the point (1, 0.25) is selected by the system and method as the amplitude threshold, i.e., the value for the minimum half wave amplitude parameter 192.

In another embodiment, a system and method for automatically deriving a parameter set for a spike detector may start out with a value for the minimum half wave amplitude parameter 191 that corresponds to an amplitude closest to the right bottom corner of the graph of FIG. 19, i.e., to the amplitude close to the point (1,0), although this selection may prove to make the detector too sensitive and therefore may require some further adjustment after a simulation or test run on some sample signals to make it less sensitive. The adjustment may be accomplished by a user over a graphical user interface (GUI) using one or more sliders such as described with reference to FIG. 6, above.

Referring now to block 863 of FIG. 8C, the next step for a system and method for automatically determining a parameter set for a spike detector may be to find a value for the minimum half wave width parameter 193 based on the user-selected region(s) of interest. Once the automatic deriving method has arrived at a value for the minimum half wave amplitude parameter 191, then the method can use that value to classify each remaining half wave (i.e., each half wave that survives hysteresis and meets or exceed the minimum amplitude requirement) as either "spike" or "non-spike." More particularly, if a half wave has an amplitude that is greater than or equal to the minimum half wave amplitude, then that half wave will be classified as a "spike" half wave (e.g., as part of a spike complex) and if a half wave has an amplitude that is less than the minimum half wave amplitude, then that half wave will be classified as a "non-spike" half wave. A lower bound for the minimum half wave width parameter 193 is initially determined by identifying the half wave in the group of "spike" half waves that has the shortest duration. After the automatic deriving method has accomplished this, then it is important to assess whether there is overlap between the durations of the half waves in the "spike" class and the durations of the half waves in the "non-spike" class. This can be easily accomplished by comparing the half wave in the "spike" class having the shortest duration (where "D1" is that duration) to the half wave in the "non-spike" class having the longest duration (where "D2" is that duration). If there is no overlap of minimum half wave width values between these two classes, then the half wave in the "non-spike" class with the longest duration becomes the new lower bound for the minimum half wave width parameter. The minimum half wave width then is defined as the value from the discrete parameter space that is greater than and closest to the shortest "spike" half wave minus 10% of the difference (D1–D2), i.e., D1–0.1 (D1–D2). If there is overlap of the minimum half wave width values for the two classes (i.e., spike and non-spike half waves), then the lower bound is set as D1 and the minimum half wave is chosen to be the minimum half wave width value closest and greater than D1.

With reference now to block 864 of FIG. 8C, an embodiment of a system and method for automatically deriving a parameter set for a half wave detector configured to look for spikes will find a value for the half wave window size parameter 195 and the half wave count criterion 194. Using the class assignments for the half wave amplitudes (i.e., "spike" or "non-spike"), the spike complexes are identified by searching for at least two of more consecutive spike-class half waves through the region or regions of interest. An average frequency of the spike complexes can be assessed as:

$$\text{Avg Frequency of } SCs = \frac{\text{Total number of } SCs}{\text{Total time duration of the } ROI} \quad (1)$$

where "SC" means "spike complex" and "ROI" means "region of interest." The duration of each spike complex in a region of interest is determined by the sum of the durations of consecutive spike half waves. A conservative half wave window size is defined as the sum of the longest spike complex, and the average spike complex period is assessed as the inverse of equation (1).

The half wave count criterion 194 is determined as the average number of half waves per spike complex pattern, which is assessed as:

$$\text{count} = \frac{1}{N}\sum_{i=1}^{N} numHW(i) \quad (2)$$

where:
numHW(i)=the total number of spike-half waves that form the ith spike complex
N=total number of spike complexes in the region(s) of interest
i=index varying from 1 to N In an embodiment, the value for the detection analysis window size parameter 197 may be fixed at 2048 ms. It will be appreciated that the value of the detection analysis window size parameter 197 may be modified using faster detection as an objective/guiding criterion. The qualified analysis window count 196 may be selected as the maximum between 1 and the average spike complex frequency. In an embodiment, the value of the detection analysis window size parameter 197 is determined to be twice the value of the qualified analysis window count 196, provided that the resulting value is available in the parameter space. (In other words, if twice the value of the qualified analysis window count is a possible value in the range of values available for the detection analysis window size, then the detection analysis window size will be set at twice the value of the qualified analysis window count.)

Activity Corresponding to a Power Change/Line Length Detector

Referring now to FIG. 8A, at block 846, the algorithm for determining an activity type ("Algorithm 1") has determined that the activity type in the user-selected region(s) of interest corresponds to a change in the power of the signal in the region(s) of interest as compared to the power that otherwise characterizes the signal. In an embodiment, when Algorithm 1 determines that a "power change" detection tool is suggested by a user's selection of a region or regions of interest, the detection tool is a line length detector. Generally, a line length detector establishes a window of time in which to operate and then divides a portion of a signal occurring in that window (e.g., within in a time period corresponding to a user-selected region of interest) into a set of samples where each sample has the same unit size, and then adds up all of the line lengths in the time window. The accumulated line lengths for the samples in the time window are then typically compared to a trend of line lengths relevant to the same signal in which the region of interest occurred, such as a trend of line lengths over a term that is longer than the time window. The trend to which the line length total for a given time window is compared may be a relatively short-term trend or a relatively long-term trend. Again, generally, if the line length in the time window increases relative to the trend, then it may be inferred that the power of the signal is changing so that there is more power in the signal corresponding to the time window than there has been based on the trend. Alternatively, if the line length in the time window decreases relative to the trend, then it may be inferred that a power change in the other direction is occurring.

A user may want to configure a line length detector to detect when the power of a signal increases (or decreases) based on the supposition that the power change may be associated with a physiological change, such as the onset of epileptiform activity. Some configurations for a line length detection tool are described in U.S. Pat. No. 6,810,285 to Pless et al. for "Seizure Sensing and Detection Using an Implantable Device" issued Oct. 26, 2004. U.S. Pat. No. 6,810,285 is hereby incorporated in the entirety by reference. The '285 patent describes implementing line length detectors as instances of a "window analysis unit" in an active implantable medical device configured to detect events in signals sensed from a patient with epilepsy.

In an embodiment, a system and method for automatically deriving a parameter set for a power change detection tool configured as a line length detection may only require input from a user to mark the start of a region of interest in a portion of a signal (e.g., in a portion of a previously-recorded ECOG for a patient). The system and method can use the marked start of the region of interest to automatically determine parameters and values for the same that are biased to detect the same or a more pronounced change in the power of the signal being sensed from the patient (most commonly, an increase in signal power (or frequency) compared to a trend).

Figure 24:
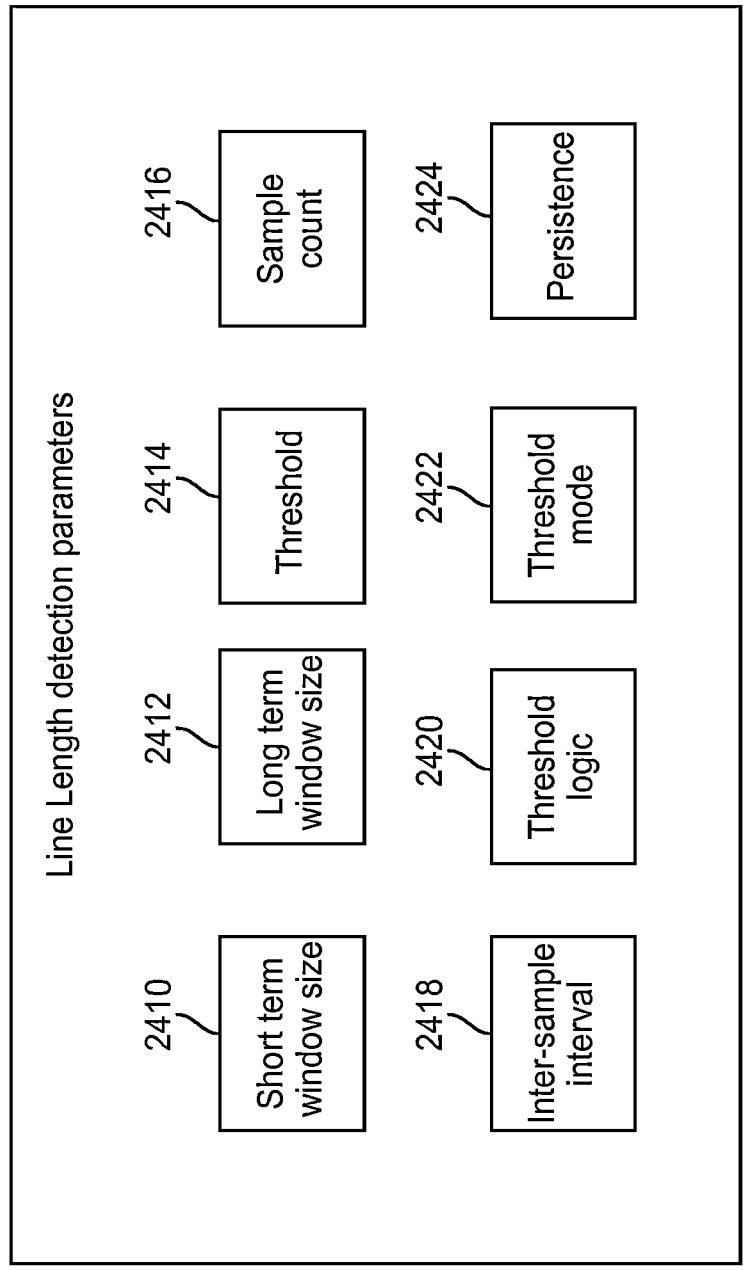
FIG. 24 is a schematic illustration of a set of adjustable detection parameters that may be, among others, associated with a line length detector.

In an embodiment, and referring now to FIG. 24, a line length detection tool is associated with a set of eight parameters the values of which should be set in order for the detection algorithm to operate optimally, and a system and method for automatically deriving a parameter set for this tool derives values for the following: a short term window size parameter 2410, a long term window size parameter 2412, a detection threshold parameter 2414, a sample count parameter 2416, an inter-sample interval parameter 2418, a threshold logic parameter 2420, a threshold mode parameter 2422, and a persistence parameter 2424. These eight parameters may be thought of as being in the "parameter space" for a line length detector.

Long Term Window Size Parameter; Sample Count Parameter; Inter-Sample Interval Parameter; Threshold Logic Parameter; and Persistence Parameter Based on experience with active implantable medical devices configured with line length detectors used in responsive neurostimulators used as a part of a therapy for epilepsy, some commonly used values for some of the line length detector operation parameters are as follows: 4096 ms for each of the inter-sample interval parameter 2418 and the long term window size parameter 2412; 1 s for the persistence parameter 2424; a "non-inverted" setting for the threshold logic parameter 2420; a "percentage" value setting for the threshold mode parameter 2422 (versus for example, a "fixed" value); and a value of 32 for the sample count parameter 2416. When experience such as this is at hand, then a system and method for automatically deriving a parameter set for a line length detector may benefit from initially establishing the parameter values at these values. If after the simulation, a user is not satisfied with the results, the system and method can begin again with different values for the parameters for the tool. Alternatively, the user may be provided with various options for adjusting the sensitivity of various aspects of detection by varying a given parameter within some bounds around the initial value.

Short Term Window Size Parameter

Again, based on experience with active implantable medical devices configured with line length detectors used in responsive neurostimulators used as a part of a therapy for epilepsy, some commonly used values for the short-term window size parameter 2410 are: 2048 ms; 4096 ms, and 1024 ms. In some embodiments, an automatic parameter deriving system and method may be configured to start out with one of these values or with a different value for the short term window size parameter 2410 if, for example, the application is other than epilepsy or the user's experience with a particular patient or set of patients is different. The short term window size parameter 2410 is also used to control the latency of the detector (e.g. to detect a change in signal earlier or later). Subsequent to establishing an initial value for the short term window size parameter 2410, and after the user has been presented with the result of the automatic parameter derivation method (e.g., via a simulation), the user may be provided a "user-friendly" feature on a display or other user/computer interactive interface, such as by dragging an indicator to the right or to the left within a window of a slider labeled to suggest in 'plain English' something that corresponds to adjusting the value of the short term window parameter 2410 (e.g., a slider may be labeled "latency" and have a left-facing arrow at one end of the slider window labeled "detect sooner" and a right-facing arrow at the other end of the slider window labeled "detect later". In other words, by moving an indicator around within a slider window, a user may adjust the latency by varying the short term window size parameter 2410. To achieve earlier detections, the short term window size parameter may be decreased within the parameter space of values available. To increase the latency and detect later, the short term window size parameter may be increased.

Percentage Threshold Parameter

Since the threshold mode parameter 2422 is configured to correspond to a percentage, it is the main parameter that controls the detection in the region of interest in at least this embodiment of a line length detector. The system and method for automatically determining a parameter set for the line length detector will use the short term window parameter 2410 so that the short term window is positioned to start at the first sample of the region of interest and to end so that the last sample of the long term window is the sample just before the region of interest.

When the line length detection algorithm runs, line length values are computed for each of the short term window and the long term window according to:

$$\text{Line length measure} = \frac{1}{L}\sum_{i=1}^{L-1}|y(i)-y(i-1)| \quad (1)$$

Expression (1) corresponds to the line length measure for a window of size L, where the unit for L is the number of samples in the window. As defined in ( ) the percentage threshold is given by:

$$\text{Percentage threshold} = \text{threshold} + \text{Line length measure in long-term window} \quad (2)$$

The maximum threshold available in the parameter space that satisfies the condition in (3) is determined to be the most appropriate threshold to detect the same signal characteristics as are present representing the power change in the region(s) of interest.

$$\text{Line length measure in short-term window} > \text{Percentage threshold} \quad (3)$$

In some embodiments, the user may be provided with an optional sensitivity adjustment, which can be in the form of slider such as the sliders described above with reference to this line length detector and to the half wave detection tools for detecting rhythmic activity and spiking activity. For example, moving an indicator around within a slider window may have the effect of varying the percentage threshold to either increase or decrease the sensitivity of the detection. This allows the user to refine the threshold parameter initially determined by the automatic parameter derivation method by increasing or decreasing its value. Again, the user need not fully appreciate how the parameter value the user is adjusting is used by the automatic parameter derivation method; the sliders or other features used to allow "fine tuning" of the values for the detection tool operating parameters will have labels that relate more closely to the visually discernible features of the signal sample encompassing the region(s) of interest than to how the parameters are actually defined for a particular instance of a detection tool (e.g., "detect more" of this or "detect less" of this versus "increase the value of the short term window" parameter or "decrease the value of the short term window parameter").

Whenever a user uses an optional sensitivity (e.g., latency) adjustment, systems and methods according to embodiments may be configured to immediately update a simulation of what the line length detector with the adjusted threshold parameter is likely to detect, for example, a simulation overlaid on an ECOG the user used to select the start of a region of interest.

It should be appreciated that in some embodiments, values for additional or different parameters may be automatically derived based on a user-selected region of interest, depending on the type of activity evident in the region(s) of interest and the particular detection tool for which the values are being determined. For example, different types of activity may suggest different types of detectors. Alternatively, and as is the case above with respect to rhythmic activity and spiking, parameters for a single type of detector (e.g., a half wave detector) may be derived in a different order or to have different values for one type of activity than for another. Examples of detection tools include but are not limited to: different varieties of half wave detectors and other detectors that operate in the time domain; detectors that operate in the frequency domain, power change detectors other than line length detectors (for example, an area detector); and detectors that are based in whole or in part on a condition of an active implanted medical device, e.g., on a device diagnostic such as the number of times an amplifier processing the physiological data saturates, etc.).

In a simple case, the examples described above use a single region of interest selected by a user, such as the region of interest 520 described with reference to FIG. 5. Referring again to FIG. 8, and in particular, at block 806, more complex examples of a method for automatically deriving parameter values for a detector may involve a user selecting more than one region of interest. As mentioned above, when a user selects more than one region of interest, a system and method according to embodiments may involve one or more preliminary calculations to determine how to treat the plurality of regions of interest.

For example, if a user selects two regions of interest and the regions of interest are quite different, then a system and method according to embodiments may automatically configure the same type of detector with different parameters for each region of interest (i.e., use two instances of the same half wave detector for each region of interest, and automatically derive a set of values for the parameters for the first instance of the half wave detector, and automatically derive a different set of values for the parameters of the second instance of the half wave detector). The methods by which values for the parameters of the two instances of the half wave detector are derived may vary based on the nature and type of activity in each user-selected region of interest.

Alternatively, in the case where a user selects two dissimilar regions of interest, the system and method may ask the user to make a choice as to, for example (1) whether the two regions of interest the user selected should each be assigned its own instance of a half wave detector; (2) whether the regions of interest should be combined; or (3) whether one region of interest should be assigned one type of detector and the other region of interest a different type of detector (e.g., one region of interest may be assigned a first half wave detector and the second region of interest may be assigned a second half wave detector (where the first half wave detector and second half wave detector have different parameters or use a given parameter or its value in different ways), or one region of interest may be assigned a half wave detector and the other may be assigned a different detector (such as a line length detector or an area detector).

On the other hand, if a user selects two regions of interest and the regions of interest are quite similar, then a system and method according to embodiments may undertake one or more preliminary computations to combine the two regions of interest before automatically deriving the parameter values for a half wave detector. Additionally, or alternatively, the system and method may prompt a user to choose whether the user wants to detect activity similar to that which is represented in each of the two regions of interest with one instance of a half wave detector or with two instances of the half wave detector.

When a user selects more than one region of interest at block 802 in FIG. 8, the function of a system and method according to embodiments that includes determining whether the regions of interest should be combined for a single instance of a detector (or for a single type of detector) is represented at block 806. The function of a system and method that includes prompting the user to provide input regarding the number of instances of a single type of detector (e.g., half wave detector) or whether different detectors (e.g., half wave detector, line length detector) ought to be used, is represented at block 812. If more than two regions of interests were selected, and the user specified that more than one detector type should be generated, the regions may still need to be further grouped into detector type. For example, if three regions of interest were selected, the first and second regions of interest may be combined to support one detector and the third region of interest may support a second detector. The function of the system that groups or combines regions of interest is represented at block 822.

An example of a case in which a user may select two dissimilar regions of interest is illustrated with reference to FIGS. 15A-15D in an application where the detector(s) are being used to detect an onset of seizure activity in a patient. FIG. 15A is a time-series representation of an electrographic signal and FIG. 15B is a spectrogram of the signal of FIG. 15A. The x-axis of each graph corresponds to time in seconds. The y-axis of FIG. 15A is in amplitude units. The signal represents seizure activity 1504. There is an "onset" 1510 characterized by highly rhythmic activity (see also the banding 1550 in the spectrogram of FIG. 15B beginning at about $t_{onset1}$ 1506, which is at about 50 seconds). For convenience, this onset period 1510 is referred to here as "Onset Type 1".

FIG. 15C is a time-series representation of another electrographic signal for the same patient and FIG. 15C is a spectrogram of that signal. The signal represents seizure activity 1560 (right-most section of FIG. 15C). There is an onset period 1574 beginning at about time $t_{onset2}$ 1570, which is at about 45 seconds, but this onset (referred to as "Onset Type 2") is not characterized by highly rhythmic activity. In this circumstance, because the user has selected two dissimilar regions of interest, it may be more appropriate to use two different detector types for these regions, such as a half wave detector for Onset Type 1 and a line length detector for Onset Type 2. Alternatively, a first half wave detector with a first set of parameters might be appropriate for detecting Onset Type 1 whenever it occurs in the patient, and a second half wave detector with a different second set of parameters might be appropriate for detecting Onset Type 2. In still another alternative, the same half wave tool might be appropriate for detecting both Onset Type 1 and Onset Type 2, but the values of the parameters used in the detector considered optimal for detecting Onset Type 1 might be different from the values considered optimal for detecting Onset Type 2.

An example of a case in which a user may select two similar regions of interest is illustrated with reference to FIGS. 16A-16D in an application where the detector(s) are being used to detect an onset of seizure activity in a patient. FIG. 16A is a time-series representation of an electrographic signal and FIG. 16B is a spectrogram of the signal of FIG. 16A. The x-axis of each graph corresponds to time in seconds. The y-axis of FIG. 16A is in amplitude units. The signal represents seizure activity 1604 (right-most section of FIG. 16A). There is an "onset" 1610 characterized by low voltage fast activity discernible at about a time $t_{onset1}$ 1606 at about 28 s (see also the dark band 1650 in the spectrogram of FIG. 16B at around 20 Hz at about $t_{onset1}$ 1606). This onset period 1610 is "Onset Type 1" for FIGS. 16A-B.

FIG. 16C is a time-series representation of another electrographic signal from the same patient and FIG. 16C is a spectrogram of that signal. The signal represents seizure activity 1660 (right-most section of FIG. 16C). There is an onset period 1674 beginning at about time $t_{onset2}$ 1670, which is at about 28 seconds, and this Onset Type 2 in FIGS. 16C-16D is similar to that of Onset Type 1 in FIGS. 16A-16B. In this circumstance, because the user has selected two similar regions of interest, it may be appropriate to associate one detector for these regions, such as a half wave detector. Moreover, where two or more regions of interest that are similar are selected by a user, the regions of interest may improve the robustness and accuracy of the system and method. For example, by providing more information about the type of activity the user would like to detect, a system and method for automatically deriving parameter values for the half wave detector may be better at identifying optimal parameter values for the patient.

Figure 17A:
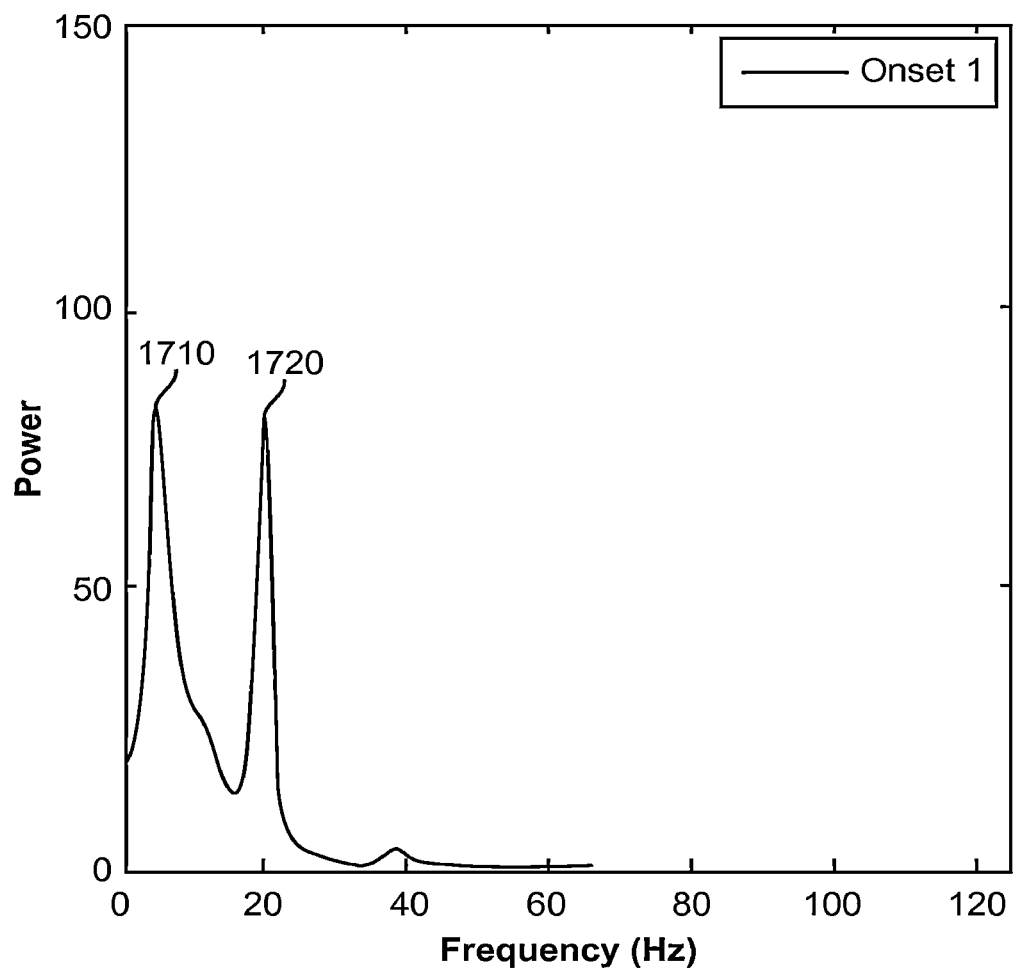
FIG. 17A is a graphical representation of the frequency response (power spectrum) for a first region of interest associated with a first onset period of a seizure.
Figure 17B:
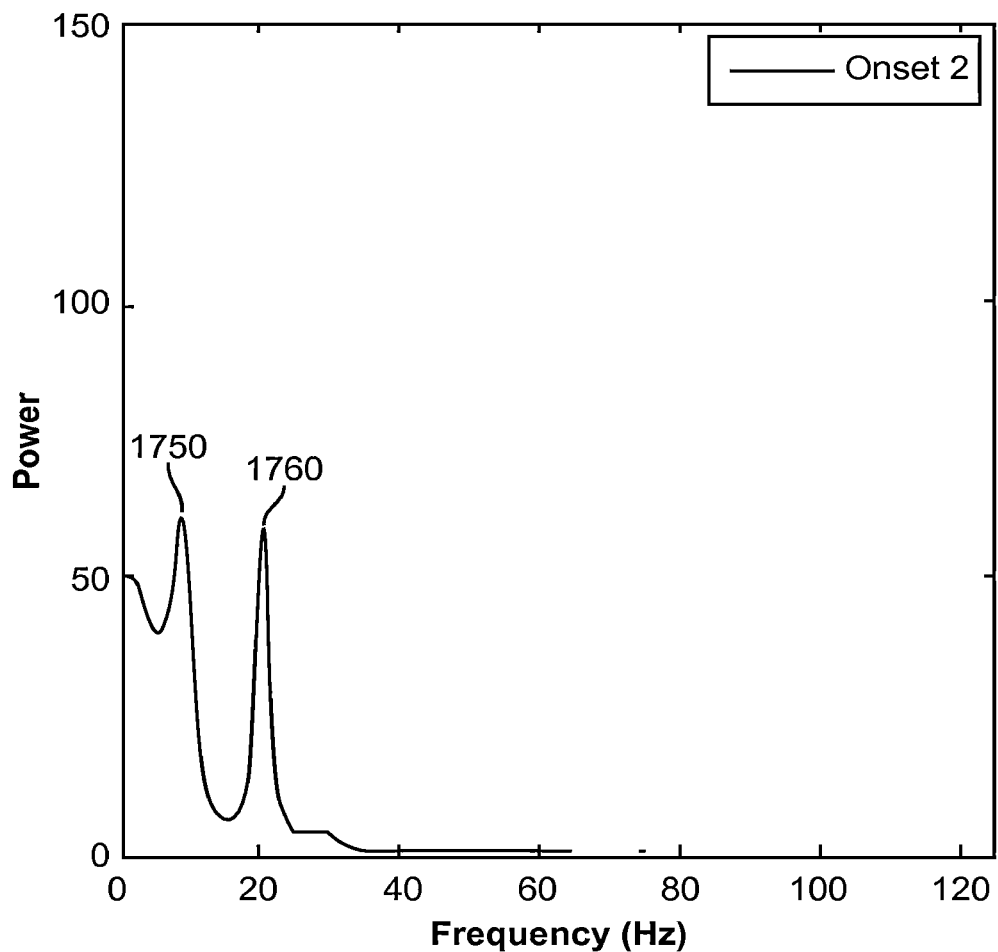
FIG. 17B is a graphical representation of the frequency response (power spectrum) for a first region of interest associated with a second onset period of a seizure.
Figure 17C:
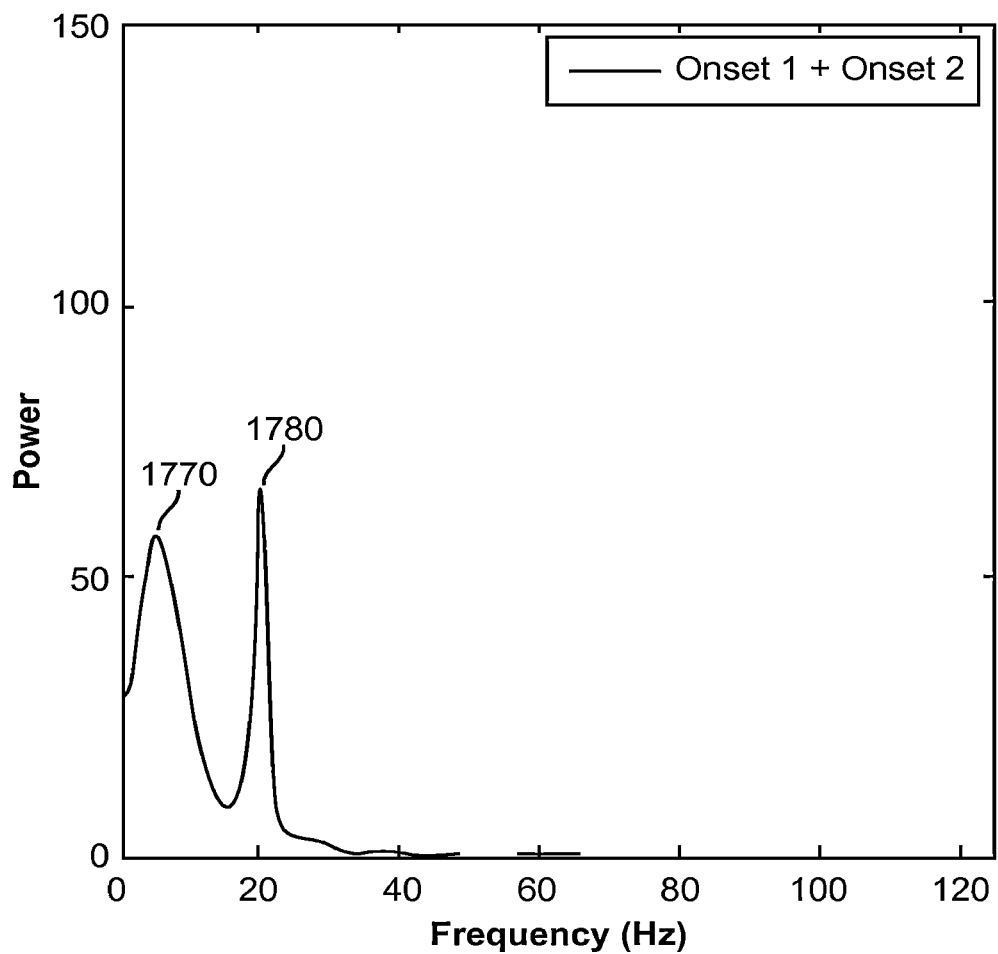
FIG. 17C is a graphical representation of a frequency response (power spectrum) for a combination according to embodiments of the first onset period of FIG. 17A and the second onset period of FIG. 17B.

FIGS. 17A-17C are graphical representations of the frequency response (power spectra) for each of two different regions of interest and for a combination of the two regions of interest. In each of the graphs of FIGS. 17A-17C, the x-axis represents frequency in Hz and the y-axis represents power. At times, it can be useful to combine in a preliminary computation or computations information from more than one user-selected region of interest so that the system and method of automatically deriving a parameter set for a half wave detector can better focus a feature of an electrographic signal which the user is interested in detecting.

For example, in FIGS. 16A-16B, Onset Type 1 corresponds to low voltage fast activity from about 29.3 s to 32.3 s and Onset Type 2 corresponds to low voltage fast activity from about 28.4 s to 31.4 s. Referring to FIG. 17A which corresponds to a first region of interest selected by the user containing Onset Type 1 activity of the type shown in FIGS. 16A-16B, a first peak frequency (or the frequency with the greatest power) is at around 5 Hz (first peak frequency for Onset Type 1 1710). The next peak frequency in FIG. 17A occurs at around 20 Hz (second peak frequency for Onset Type 1 1720). Referring to FIG. 17B which corresponds to a second region of interest selected by the user containing Onset Type 2 activity of the type shown in FIGS. 16C-16D, a first peak frequency is at around 9 Hz (first peak frequency for Onset Type 2 1750), and a second peak frequency occurs at about 20 Hz (second peak frequency for Onset Type 2 1760). When the regions of interest for Onset Type 1 and Onset Type 2 are combined in this example, the graph showing the frequency response is shown in FIG. 17C. It can be appreciated that a first peak frequency occurs at about 5 Hz (first peak frequency for combination of Onset Type 1 and Onset Type 2 1770) and a second peak frequency occurs at about 20 Hz (second peak frequency for combination of Onset Type 1 and Onset Type 2 1780). A computation (or computations) that combines user-selected regions of interest preliminary to automatically deriving values for the parameters of a detector, such as a half wave detector, thus may be useful in identifying one or more common features of a set of regions of interest. In this case, the common feature might be a salient frequency 1080 at 20 Hz because this is a peak frequency that is present in the combination of both of the two regions of interest selected by the user (and also is present in each of the individual regions of interest).

From the foregoing, it can be appreciated that the approach of choosing values for the parameters relevant to a particular detection tool in pairs and/or in a logical sequence encourages results that are more likely to be closely matched to the nature and type of activity a user decides to detect (e.g., by selecting region(s) of interest) than would be systems and methods that rely on assigning values to each relevant parameter randomly or one at a time in a "brute force" approach.

It is anticipated that in some embodiments the system and method for automatically deriving parameter values for a detection tool would be accomplished primarily using external components rather than an implantable component with a limited power supply. In these embodiments, multiple iterations of a method could be undertaken with input from a user (e.g., to select the number of instances of a detector, the types of detectors, and to adjust the sensitivity of a detector (such as with a "pattern duration" or "signal amplitude" slider as described above) without consuming power from the implant). When the user is satisfied with the simulation results, the user can save the set of parameter values derived by the method, locally on an external component and/or in a central database (in the case of the RNS SYSTEM, the detection set may be saved on the physician-user's programmer and/or in the Patient Management Database ("PDMS") which is accessible over a secure website).

In other embodiments, there may be opportunities to implement the system and method for automatically deriving a set of parameters for a detection tool in part using an implantable component in communication with an external component, such as a user interface with a display and user input capability. In still other embodiments, there may be some capability for a system and method according to embodiments for automatically adjusting values initially established by a parameter-set-derivation method based on feedback from the implanted device, a user or the patient. For example, the user may identify a target detection rate and the implanted device may adjust detection parameters (e.g. increasing or decreasing the minimum half wave amplitude parameter 192 to achieve the target detection rate). A "System and Method for Automatically Adjusting Detection Thresholds in a Feedback-Controlled Neurological Event Detector" is described in U.S. Pat. No. 8,131,352 to Greene, issued Mar. 6, 2012. U.S. Pat. No. 8,131,352 is hereby incorporated by reference in the entirety.

Various example embodiments are thus described. All statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein but rather is defined by the appended claims.

What is claimed is:

1. A method of deriving a detection tool that detects for an event in electrographic signals, the detection tool to be implemented in an implantable medical device implanted in a patient, the method comprising:
   a. processing a region of interest in an electrographic signal sensed by the implantable medical device to determine a candidate parameter set that configures a candidate detection tool to detect the event;
   b. configuring the candidate detection tool based on the candidate parameter set;
   c. applying the candidate detection tool to a plurality of available electrographic signals to determine an event detection rate for the candidate detection tool, wherein the plurality of available electrographic signals are signals of other patients with one or more demographics in common with the patient;
   d. comparing the event detection rate to a criterion corresponding to a desired detection rate; and
   e. in response to the criterion being satisfied, implementing the candidate detection tool as the detection tool in the implantable medical device.

2. The method of claim 1, wherein the plurality of available electrographic signals further comprise signals of the patient that are sensed and stored by the implantable medical device.

3. The method of claim 1, wherein the plurality of available electrographic signals further comprise signals of the patient that are sensed in real time by the implantable medical device.

4. The method of claim 1, further comprising:
   in response to the criterion not being satisfied, adjusting a value of one or more of the parameters of the candidate parameter set; and
   repeating steps b, c, d, and e.

5. A method of deriving a detection tool that detects for an event in electrographic signals, the detection tool to be implemented in an implantable medical device implanted in a patient, the method comprising:
   a. processing a region of interest in an electrographic signal sensed by the implantable medical device to determine a candidate parameter set that configures a candidate detection tool to detect the event;
   b. configuring the candidate detection tool based on the candidate parameter set;
   C. applying the candidate detection tool to a plurality of available electrographic signals to determine an event detection rate for the candidate detection tool;
   d. comparing the event detection rate to a criterion corresponding to a desired detection rate; and
   e. in response to the criterion being satisfied, implementing the candidate detection tool as the detection tool in the implantable medical device,
   wherein processing a region of interest in an electrographic signal comprises:
      analyzing the region of interest to determine from among a plurality of different activity types, a determined activity type with which to characterize the region of interest; and
      based on the determined activity type, automatically selecting the candidate detection tool from among a plurality of different types of detection tools.

6. The method of claim 5, wherein the electrographic signal sensed by the implantable medical device comprises an event corresponding to a seizure onset and the region of interest is at or near the seizure onset.

7. The method of claim 5, wherein the plurality of different types of detection tools comprises a half wave detector configured to look for rhythmic activity, a half wave detector configured to look for spiking activity and a line length detector configured to look for a power change.

8. The method of claim 5, wherein the plurality of different activity types comprises rhythmic activity, spiking activity, and a change in power of the electrographic signal compared to a predetermined norm.

9. The method of claim 8, wherein the determined activity type is rhythmic activity, the detection tool is a half wave detector, and the parameter set comprises one or more of a half wave hysteresis parameter, a minimum half wave amplitude parameter, a minimum half wave width parameter, a half wave count criterion parameter, a half wave window size parameter, a qualified analysis window count parameter, and a detection analysis window size parameter.

10. The method of claim 8, wherein the determined activity type is spiking activity, the detection tool is a half wave detector, and the parameter set comprise one or more of a half wave hysteresis parameter, a minimum half wave amplitude parameter, a minimum half wave width parameter, a half wave count criterion parameter, a half wave window size parameter, a qualified analysis window count parameter, and a detection analysis window size parameter.

11. The method of claim 8, wherein the determined activity type is an activity corresponding to a change in power of the electrographic signal compared to a predetermined norm, the detection tool is a line length detector, and the parameter set comprises one or more of a value of a short term window size parameter, a value of a long term window size parameter, a value of a detection threshold parameter, a value of a threshold logic parameter, a value of a threshold mode parameter, a value of a sample count parameter, a value of an inter-sample interval parameter, and a value of a persistence parameter.

12. A system deriving a detection tool that detects for an event in electrographic signals, the detection tool to be implemented in an implantable medical device implanted in a patient, the system comprising:
   a memory; and
   a processor coupled to the memory and configured to:
      a. process a region of interest in an electrographic signal sensed by the implantable medical device to determine a candidate parameter set that configures a candidate detection tool to detect the event;
      b. configure the candidate detection tool based on the candidate parameter set;

c. apply the candidate detection tool to a plurality of electrographic signals to determine an event detection rate for the candidate detection tool, wherein the plurality of available electrographic signals are signals of other patients with one or more demographics in common with the patient;

d. compare the event detection rate to a criterion corresponding to a desired detection rate; and e. in response to the criterion being satisfied, implement the candidate detection tool as the detection tool in the implantable medical device.

13. The system of claim 12, wherein the plurality of available electrographic signals further comprise signals of the patient that are sensed and stored by the implantable medical device.

14. The system of claim 12, wherein the plurality of available electrographic signals further comprise signals of the patient that are sensed in real time by the implantable medical device.

15. The system of claim 12, wherein the processor is further configured to:

in response to the criterion not being satisfied, adjust a value of one or more of the parameters of the candidate parameter set; and repeat steps b, c, d, and e.

16. A system deriving a detection tool that detects for an event in electrographic signals, the detection tool to be implemented in an implantable medical device implanted in a patient, the system comprising:

a memory; and a processor coupled to the memory and configured to:

a. process a region of interest in an electrographic signal sensed by the implantable medical device to determine a candidate parameter set that configures a candidate detection tool to detect the event;

b. configure the candidate detection tool based on the candidate parameter set;

c. apply the candidate detection tool to a plurality of electrographic signals to determine an event detection rate for the candidate detection tool;

d. compare the event detection rate to a criterion corresponding to a desired detection rate; and e. in response to the criterion being satisfied, implement the candidate detection tool as the detection tool in the implantable medical device, wherein the processor processes a region of interest in an electrographic signals by being further configured to:

analyze the region of interest to determine from among a plurality of different activity types, a determined activity type with which to characterize the region of interest; and based on the determined activity type, automatically select the candidate detection tool from among a plurality of different types of detection tools.

17. The system of claim 16, wherein the electrographic signal sensed by the implantable medical device comprises an event corresponding to a seizure onset and the region of interest is at or near the seizure onset.

18. The system of claim 16, wherein the plurality of different types of detection tools comprises a half wave detector configured to look for rhythmic activity, a half wave detector configured to look for spiking activity and a line length detector configured to look for a power change.

19. The system of claim 16, wherein the plurality of different activity types comprises rhythmic activity, spiking activity, and a change in power of the electrographic signal compared to a predetermined norm.

* * * * *